(12) United States Patent
Shah

(10) Patent No.: US 12,718,906 B2
(45) Date of Patent: Aug. 25, 2026

(54) METHODS AND SYSTEMS FOR BARCODE-ASSISTED IMAGE REGISTRATION AND ALIGNMENT

(71) Applicant: 10x Genomics, Inc., Pleasanton, CA (US)

(72) Inventor: Preyas Shah, Milpitas, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1319 days.

(21) Appl. No.: 17/476,400

(22) Filed: Sep. 15, 2021

(65) Prior Publication Data

US 2022/0083832 A1 Mar. 17, 2022

Related U.S. Application Data

(60) Provisional application No. 63/213,447, filed on Jun. 22, 2021, provisional application No. 63/079,007,
(Continued)

(51) Int. Cl.
*G16B 30/10* (2019.01)
*C12N 15/10* (2006.01)
(Continued)

(52) U.S. Cl.
CPC ........... *G16B 30/10* (2019.02); *G06K 7/1473* (2013.01); *G16B 5/20* (2019.02); *G16B 15/00* (2019.02);
(Continued)

(58) Field of Classification Search
None
See application file for complete search history.

(56) References Cited

U.S. PATENT DOCUMENTS 10,457,980 B2 10/2019 Cai et al.
11,021,737 B2 6/2021 Church et al.
(Continued)

FOREIGN PATENT DOCUMENTS

WO WO 2018/026873 2/2018
WO WO 2019/204702 10/2019
(Continued)

OTHER PUBLICATIONS

Moffitt, Jeffrey R., et al. "High-throughput single-cell gene-expression profiling with multiplexed error-robust fluorescence in situ hybridization." Proceedings of the National Academy of Sciences 113.39 (2016): 11046-11051. (Year: 2016).*
(Continued)

*Primary Examiner* — Karlheinz R. Skowronek
*Assistant Examiner* — Mary C Leverett
(74) *Attorney, Agent, or Firm* — MORRISON & FOERSTER LLP

(57) ABSTRACT

Methods and systems for designing large sets of barcodes that ensure robust and efficient error correction capabilities are described. Also described are methods for assigning barcodes to target analytes that minimize optical crowding in in situ detection applications. Furthermore, methods for
(Continued)

performing barcode error correction and for performing barcode-assisted image registration and alignment are also described.

28 Claims, 31 Drawing Sheets
(12 of 31 Drawing Sheet(s) Filed in Color)

Related U.S. Application Data filed on Sep. 16, 2020, provisional application No. 63/079,004, filed on Sep. 16, 2020, provisional application No. 63/079,029, filed on Sep. 16, 2020, provisional application No. 63/078,999, filed on Sep. 16, 2020, provisional application No. 63/079,035, filed on Sep. 16, 2020, provisional application No. 63/079,034, filed on Sep. 16, 2020.

(51) Int. Cl.

| | |
|---|---|
| ***C12N 15/62*** | (2006.01) |
| ***C12Q 1/68*** | (2018.01) |
| ***G06K 7/14*** | (2006.01) |
| ***G16B 5/20*** | (2019.01) |
| ***G16B 15/00*** | (2019.01) |
| ***G16B 25/20*** | (2019.01) |
| ***G16B 30/00*** | (2019.01) |
| ***G16B 30/20*** | (2019.01) |

(52) U.S. Cl.

CPC ............. *G16B 25/20* (2019.02); *G16B 30/20* (2019.02); *C12N 15/1062* (2013.01); *C12N 15/625* (2013.01); *C12Q 1/68* (2013.01); *G16B 30/00* (2019.02)

(56) References Cited

U.S. PATENT DOCUMENTS

| | | | |
|---|---|---|---|
| 11,085,072 | B2 | 8/2021 | Church et al. |
| 11,098,303 | B2 | 8/2021 | Zhuang et al. |
| 2015/0080266 | A1 | 3/2015 | Volkmuth |
| 2018/0033256 | A1 | 2/2018 | Hamidat et al. |
| 2019/0095578 | A1 | 3/2019 | Shum et al. |
| 2019/0264270 | A1 | 8/2019 | Zhuang et al. |
| 2020/0224244 | A1 | 7/2020 | Nilsson et al. |
| 2021/0017587 | A1 | 1/2021 | Cai et al. |
| 2021/0164039 | A1 | 6/2021 | Wang et al. |
| 2022/0084628 | A1 | 3/2022 | Shah |
| 2022/0084629 | A1 | 3/2022 | Shah |

FOREIGN PATENT DOCUMENTS

| | | | |
|---|---|---|---|
| WO | 2020123742 | A1 | 6/2020 |
| WO | 2020240025 | A1 | 12/2020 |
| WO | 2021127019 | A1 | 6/2021 |
| WO | WO 2022/060889 | | 3/2022 |

OTHER PUBLICATIONS

Billings, Seth D., Emad M. Boctor, and Russell H. Taylor. "Iterative most-likely point registration (IMLP): A robust algorithm for computing optimal shape alignment." PloS one 10.3 (2015): e0117688. (Year: 2015).*

Alon et al., "Expansion Sequencing: Spatially Precise In Situ Transcriptomics in Intact Biological Systems", Science (2021) 371(6528); eaax2656 (doi:10.1126/science.aax2656.).

Buschmann et al., "Levenshtein error-correcting barcodes for multiplexed DNA sequencing," BMC Bioinformatics. (2013) 14: 272.

Chen et al., "RNA imaging. Spatially resolved, highly multiplexed RNA profiling in single cells," Science. (2015) 348 (6233): aaa6090. 36 pgs.

Chen et al., "Spatially Resolved, Highly Multiplexed RNA Profiling in Single Cells", Science (2015) 348(6233):412.

Crum et al., "Non-Rigid Image Registration: Theory and Practice", The British Journal of Radiology (2004) 77: S140-S153.

Eng et al., "Transcriptome-scale super-resolved imaging in tissues by RNA seqFISH," Nature. (2019) 568(7751): 235-239.

Holden, M. "A Review of Geometric Transformations for Nonrigid Body Registration", IEEE Transactions on Medical Imaging (2008) 27:111-128.

Ke et al., "In situ sequencing for RNA analysis in preserved tissue and cells," Nat Methods. (2013) 10(9):857-60.

Lee et al., "Highly multiplexed subcellular RNA sequencing in situ", Science. (2014) 343(6177):1360-1363. doi: 10.1126/science.1250212.

Lubeck et al., "Single-cell in situ RNA profiling by sequential hybridization," Nat Methods. (2014) 11(4): 360-361.

Moffitt et al., "RNA Imaging with Multiplexed Error-Robust Fluorescence In Situ Hybridization (MERFISH)," Methods in Enzymology, (2016) 572: 1-49.

Nelder et al., "A Simplex Method for Function Minimization," Computer Journal. (1965) 7(4): 308-313.

Zhu et al., "A Review of Point Set Registration: From Pairwise Registration to Groupwise Registration", (2019) Sensors 19(5): 1191.

Asp et al., "A Spatiotemporal Organ-Wide Gene Expression and Cell Atlas of the Developing Human Heart," Cell (2019) 179(7):1647-1660.

Hamady et al., "Error-Correcting Barcoded Primers for Pyrosequencing Hundreds of Samples in Multiplex," Nature Methods (2008) 5(3):235-237.

MiSeq System User Guide, Part #15027617 H, Illumina, Inc., Mar. 2013 (Year: 2013).

Schober et al, Design of Short Barcodes for Next Generation Sequencing of DNA and RNA, Proceedings of the 2012 IEEE International Workshop on Genomic Signal Processing and Statistics, pp. 31-34, IEEE Xplore, Apr. 2013 (Year: 2013).

* cited by examiner

METHODS AND SYSTEMS FOR BARCODE-ASSISTED IMAGE REGISTRATION AND ALIGNMENT

CROSS-REFERENCE TO RELATED APPLICATIONS

This application claims the priority benefit of United States Provisional Patent Application Ser. No. 63/078,999, filed Sep. 16, 2020; 63/079,004, filed Sep. 16, 2020; 63/079,007, filed Sep. 16, 2020; 63/079,029, filed Sep. 16, 2020; 63/079,034, filed Sep. 16, 2020; 63/079,035, filed Sep. 16, 2020; and 63/213,447, filed Jun. 22, 2021, the contents of each of which are incorporated herein by reference in their entirety.

FIELD OF THE DISCLOSURE

The present disclosure relates generally to methods and systems for molecular barcoding, and more specifically to methods and systems for designing barcodes (e.g., nucleic acid barcode sequences) that facilitate the identification of target analytes (e.g., for in situ detection applications) and enable efficient barcode error detection and correction for a variety of assay applications and formats including, but not limited to, in situ detection, spatial arrays, bead arrays, etc.

BACKGROUND OF THE DISCLOSURE

Molecular barcoding techniques are widely used in a variety of biomolecule detection and nucleic acid sequencing-based applications. Barcodes (e.g., nucleic acid sequences) are molecules that form unique labels or identifiers that convey, or are capable of conveying, information about, e.g., the presence of an analyte molecule in a sample, the number of individual analyte molecules of a given type present in a sample, the location of a cell or bead in a sample or on a support surface, the sample of origin in a multiplexed sample analysis technique, etc. In some instances, barcodes (e.g., nucleic acid barcode sequences) may be identified and decoded directly (e.g., by nucleic acid sequencing). In some instances, barcodes (e.g., nucleic acid barcode sequences) may be identified and decoded indirectly (e.g., by detecting the hybridization of a series of one or more barcode probes to one or more nucleic acid barcode sequences, where each barcode probe comprises an oligonucleotide sequence that is complementary to all or a portion of the one or more nucleic acid barcode sequences).

Decoding methods used in decoding barcoded nucleic acid molecules or other targets (e.g., peptides, proteins, cells, etc.) in a biological sample can be prone to introducing errors in the detected barcode sequences due to "noisy" decoding processes. By way of analogy, consider a mobile phone communication system. In the mobile phone communication system, a base station may encode messages W into a binary signal X, and transmit the signal X over some distance (i.e., the communication channel) to a destination phone. The phone receives the encoded messages as Y, and decodes them into $\hat{W}$, which is ideally identical to the messages W that were originally sent. However, $\hat{W}$ is often corrupted by the communication channel as the channel is noisy and introduces errors that flip individual bits in the binary signal X This scenario is similar to that encountered with decoding methods in that the decoding process (i.e., the "communication channel") may introduce errors which can be modeled by the conditional probability $P(Y|X)$, i.e., the probability that a decoded barcode sequence Y comprising an error will be determined (or, in the mobile phone analogy, that an encoded message Y comprising an error will be received) given the knowledge that designed barcode sequence X was the input for the decoding process (or, in the mobile phone analogy, that binary signal X has been sent over the communication channel). In the context of decoding methods for nucleic acid barcode sequences, errors such as substitution errors in the detected sequences corrupt the encoded signal and give rise to erroneous decoded barcode sequences.

The decoding module for the mobile phone is typically a hardware circuit that performs algorithmic steps of error correction by picking the candidate message W that best explains the original signal. Accordingly, the decoding method should be tuned to the error model for the communication channel to improve performance. Also, the error model should be well-characterized to reduce the number of false-positive corrections.

Decoding methods used in decoding nucleic acid barcodes are subject to similar errors. Depending on the specific application, potential sources of error include, but are not limited to, amplification errors occurring during nucleic acid amplification, substitution-type base-calling errors in nucleic acid sequencing, non-specific and/or mismatched hybridization of barcode probes to nucleic acid barcode sequences, incomplete reagent clearing (e.g., of barcode probes) between decoding cycles, etc. In addition, error model characterization in imaging-based decoding methods is exceptionally challenging due to additional complications such as autofluorescence and optical crowding.

For some applications, e.g., in situ detection, other potential sources of error can make imaging-based decoding of nucleic acid barcode sequences more challenging as well. For example, to successfully decode a barcoded gene or gene transcript location (e.g., the location of a barcoded gene sequence or corresponding mRNA molecule in a tissue sample), three-dimensional registration between the images of a plurality of image stacks corresponding to different fields-of-view and different decoding cycles is required. Tissue deformation between imaging and decoding cycles may arise from reagent exchange, etc., and can cause registration errors that create barcode decoding errors.

Thus, there remains a need for improved barcode design methods that enable more efficient error detection and correction, and improved decoding methods that enable more accurate recovery of barcoded information.

SUMMARY OF THE DISCLOSURE

Disclosed herein are methods and systems for improved barcode design that enable more efficient error detection and correction of decoded barcodes. Also disclosed are methods and systems for improved decoding of barcode sequences that enable more accurate recovery of barcoded information.

Disclosed herein are computer-implemented methods for adjusting image registration comprising: obtaining an image for each decoding cycle of a plurality of decoding cycles to obtain a series of images; registering one or more images of the series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences, or segments thereof; decoding a plurality of target oligonucleotide sequences based on which decoding cycle and for which locations in one or more images of the series of images the one or more barcode probe sequences of the plurality are detected to obtain a plurality of decoded target oligonucleotide sequences; identifying a subset of the plurality of decoded target oligonucleotide sequences; and adjusting the registration of the one or more images of the series of images to align the locations of the subset of decoded target oligonucleotide sequences.

In some embodiments, the target oligonucleotide sequences comprise target analyte sequences. In some embodiments, the target analyte sequences comprise messenger ribonucleic acid (mRNA) sequences. In some embodiments, the target oligonucleotide sequences comprise target barcode sequences associated with target analytes. In some embodiments, the computer-implemented method further comprises applying an error correction method to the plurality of decoded target oligonucleotide sequences prior to identifying the subset of decoded target oligonucleotide sequences. In some embodiments, the error correction method comprises an iterative adjustment of the registration of the one or more images of the series of images to correct errors in one or more decoded target oligonucleotide sequences of the subset of decoded target oligonucleotide sequences. In some embodiments, the iterative adjustment is repeated until an improvement in a number of corrected target oligonucleotide sequences in the subset from one iteration to the next is less than a specified threshold. In some embodiments, the error correction method comprises replacement of one or more of the plurality of decoded target oligonucleotide sequences with a known target oligonucleotide sequence that is within a specified pairwise edit distance of the decoded target oligonucleotide sequence. In some embodiments, the specified pairwise edit distance comprises a specified pairwise Hamming distance, a specified pairwise Levenshtein distance, or a specified pairwise longest common subsequence (LCS) distance. In some embodiments, the specified pairwise edit distance comprises a specified pairwise Hamming distance of less than two times a specified error correction capability. In some embodiments, the error correction method comprises replacement of one or more of the plurality of decoded target oligonucleotide sequences with a known target oligonucleotide sequence that has a maximum likelihood as computed from a probability distribution that provides probabilities for detecting a given barcode probe sequence at a given location in a given decoding cycle. In some embodiments, the error correction method comprises replacement of one or more of the plurality of decoded target oligonucleotide sequences with a known target oligonucleotide sequence that is within a specified pairwise edit distance of the decoded target oligonucleotide sequence, and that has a maximum likelihood as computed from a probability distribution that provides probabilities for detecting a given barcode probe sequence at a given location in a given decoding cycle. In some embodiments, the specified pairwise edit distance comprises a specified pairwise Hamming distance, a specified pairwise Levenshtein distance, or a specified pairwise longest common subsequence (LCS) distance. In some embodiments, the specified pairwise edit distance comprises a specified pairwise Hamming distance of less than two times a specified error correction capability. In some embodiments, adjusting the registration of one or more images further comprises using detected locations for one or more fiducials in addition to the subset of decoded target oligonucleotide sequences.

Also disclosed herein are computer-implemented methods for aligning and stitching image tiles comprising: obtaining a plurality of image tiles, wherein each image tile of the plurality corresponds to a different field-of-view of a sample that indicates the locations of a plurality decoded target oligonucleotide sequences; identifying a subset of the decoded target oligonucleotide sequences that are present in an overlapping region of a first image tile of the plurality of image tiles and a second image tile of the plurality of image tiles that is adjacent to the first image tile; determining a spatial transformation between the first image tile and the second image tile based on locations of the subset of decoded target oligonucleotide sequences in the first image tile and locations of the subset of decoded target oligonucleotide sequences in the second image tile; applying the spatial transformation to the second image tile; and stitching the transformed second image tile and the first image tile to generate a composite image.

In some embodiments, the target oligonucleotide sequences comprise target analyte sequences. In some embodiments, the target analyte sequences comprise messenger ribonucleic acid (mRNA) sequences. In some embodiments, the target oligonucleotide sequences comprise target barcode sequences associated with target analytes. In some embodiments, the images tiles of the plurality of image tiles are generated by a process comprising: obtaining an image for each decoding cycle of a plurality of decoding cycles to obtain a series of images for a given field-of-view; registering one or more images of the series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences present in the given field-of-view based on which decoding cycle and for which locations in one or more images of the series of images the one or more barcode probe sequences of the plurality are detected to obtain a plurality of decoded target oligonucleotide sequences; identifying a subset of the plurality of decoded target oligonucleotide sequences; and adjusting the registration of the one or more images of the series of images for the field-of-view to align the locations of the subset of decoded target oligonucleotide sequences. In some embodiments, the computer-implemented method further comprises applying an error correction method to the plurality of decoded target oligonucleotide sequences prior to adjusting the registration of one or more images of the series of images for each field-of-view. In some embodiments, the error correction method comprises an iterative adjustment of the registration of one or more images of the series of images for each field-of-view to correct errors in one or more of the subset of decoded target oligonucleotide sequences. In some embodiments, the iterative adjustment is repeated until an improvement in a number of corrected target oligonucleotide sequences in the subset from one iteration to the next is less than a specified threshold. In some embodiments, the error correction method comprises replacement of one or more of the plurality of decoded target oligonucleotide sequences with a known target oligonucleotide sequence that is within a specified pairwise edit distance of the decoded target oligonucleotide sequence. In some embodiments, the specified pairwise edit distance comprises a specified pairwise Hamming distance, a specified pairwise Levenshtein distance, or a specified pairwise longest common subsequence (LCS) distance. In some embodiments, the specified pairwise edit distance comprises a specified pairwise Hamming distance of less than two times a specified error correction capability. In some embodiments, the error correction method comprises replacement of one or more of the plurality of decoded target oligonucleotide sequences with a known target oligonucleotide sequence that has a maximum likelihood as computed from a probability distribution that provides probabilities for detecting a given barcode probe sequence at a given location in a given decoding cycle. In some embodiments, the error correction method comprises replacement of one or more of the plurality of decoded target oligonucleotide sequences with a known target oligonucleotide sequence that that is within a specified pairwise edit distance of the decoded target oligonucleotide sequence, and that has a maximum likelihood as computed from a probability distribution that provides probabilities for detecting a given barcode probe sequence at a given location in a given decoding cycle. In some embodiments, the specified pairwise edit distance comprises a specified pairwise Hamming distance, a specified pairwise Levenshtein distance, or a specified pairwise longest common subsequence (LCS) distance. In some embodiments, the specified pairwise edit distance comprises a specified pairwise Hamming distance of less than two times a specified error correction capability. In some embodiments, the spatial transformation comprises a two-dimensional spatial transformation. In some embodiments, the spatial transformation comprises a three-dimensional spatial transformation. In some embodiments, the spatial transformation is a rigid transformation comprising a rotation, translation, or any combination thereof. In some embodiments, the rigid transformation is determined using an iterative random sample consensus (RANSAC) method. In some embodiments, the rigid transformation is determined using a point set registration method. In some embodiments, the point set registration method comprises a pairwise point set registration method. In some embodiments, the point set registration method comprises a coherent point drift (CPD) method. In some embodiments, the spatial transformation is a non-rigid transformation comprising a scale change, a shear, stretching in one or more dimensions, or any combination thereof. In some embodiments, the non-rigid transformation is determined using a radial basis function, B-spline method, wavelet method, free form deformation (FFD) model, or any combination thereof.

Disclosed herein are systems comprising: one or more processors; memory operably coupled to the one or more processors; and one or more programs stored in the memory that, when executed by the one or more processors, cause the system to execute a method comprising: obtaining an image for each decoding cycle of a plurality of decoding cycles to obtain a series of images; registering one or more images of the series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences based on which decoding cycle and for which locations in one or more images of the series of images the one or more barcode probe sequences of the plurality are detected to obtain a plurality of decoded target oligonucleotide sequences; identifying a subset of the plurality of decoded target oligonucleotide sequences; and adjusting the registration of the one or more images of the series of images to align the locations of the subset of decoded target oligonucleotide sequences.

Also disclosed herein are systems comprising: one or more processors; memory operably coupled to the one or more processors; and one or more programs stored in the memory that, when executed by the one or more processors, cause the system to execute a method comprising: obtaining a plurality of image tiles, wherein each image tile of the plurality corresponds to a different field-of-view of a sample that indicates the locations of a plurality decoded target oligonucleotide sequences; identifying a subset of the decoded target oligonucleotide sequences that are present in an overlapping region of a first image tile of the plurality of image tiles and a second image tile of the plurality of image tiles that is adjacent to the first image tile; determining a spatial transformation between the first image tile and the second image tile based on locations of the subset of decoded target oligonucleotide sequences in the first image tile and locations of the subset of decoded target oligonucleotide sequences in the second image tile; applying the spatial transformation to the second image tile; and stitching the transformed second image tile and the first image tile to generate a composite image.

Disclosed herein are non-transitory computer-readable storage media storing one or more programs, the one or more programs comprising instructions which, when executed by one or more processors of a computing platform, cause the computing platform to perform a method comprising: obtaining an image for each decoding cycle of a plurality of decoding cycles to obtain a series of images; registering one or more images of the series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences based on which decoding cycle and for which locations in one or more images of the series of images the one or more barcode probe sequences of the plurality are detected to obtain a plurality of decoded target oligonucleotide sequences; identifying a subset of the plurality of decoded target oligonucleotide sequences; and adjusting the registration of the one or more images of the series of images to align the locations of the subset of decoded target oligonucleotide sequences.

Also disclosed herein are non-transitory computer-readable storage media storing one or more programs, the one or more programs comprising instructions which, when executed by one or more processors of a computing platform, cause the computing platform to perform a method comprising: obtaining a plurality of image tiles, wherein each image tile of the plurality corresponds to a different field-of-view of a sample that indicates the locations of a plurality decoded target oligonucleotide sequences; identifying a subset of the decoded target oligonucleotide sequences that are present in an overlapping region of a first image tile of the plurality of image tiles and a second image tile of the plurality of image tiles that is adjacent to the first image tile; determining a spatial transformation between the first image tile and the second image tile based on locations of the subset of decoded target oligonucleotide sequences in the first image tile and locations of the subset of decoded target oligonucleotide sequences in the second image tile; applying the spatial transformation to the second image tile; and stitching the transformed second image tile and the first image tile to generate a composite image.

Disclosed herein are computer-implemented methods for error correction of decoded target barcode sequences comprising: obtaining an image for each decoding cycle of a plurality of decoding cycles to obtain a series of images;

detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences based on which decoding cycle and for which locations in one or more images of the series of images the one or more respective barcode probe sequences of the plurality are detected to obtain a plurality of decoded target oligonucleotide sequences; and correcting one or more of the decoded target oligonucleotide sequences of the plurality by replacement with a known target oligonucleotide sequence, or proxy thereof, that has a maximum likelihood as computed from a probability distribution that provides probabilities for detecting a given barcode probe sequence at a given location in a given decoding cycle.

In some embodiments, the computer-implemented method further comprises detecting the presence of one or more target analytes in a sample based on the one or more corrected target oligonucleotide sequences. In some embodiments, the target oligonucleotide sequences comprise target analyte sequences. In some embodiments, the target analyte sequences comprise messenger ribonucleic acid (mRNA) sequences. In some embodiments, the target oligonucleotide sequences comprise target barcode sequences associated with target analytes. In some embodiments, the target barcode sequences comprise sequences of individual nucleotides. In some embodiments, the target barcode sequences comprise a plurality of segments, and each segment comprises a plurality of nucleotides. In some embodiments, the target barcode sequences function as proxies for target analyte sequences. In some embodiments, the target barcode sequences comprise from 2 to 10 segments. In some embodiments, each segment comprises from 2 to 20 nucleotides. In some embodiments, the correcting step further comprises replacement of the one or more decoded target oligonucleotide sequences with a known target oligonucleotide sequence from a subset of known target oligonucleotide sequences, or proxies thereof, that are within a specified pairwise edit distance of the decoded target oligonucleotide sequence, and wherein the maximum likelihood is computed from the probability distribution for the subset of known target oligonucleotide sequences. In some embodiments, the specified pairwise edit distance comprises a specified pairwise Hamming distance, a specified pairwise Levenshtein distance, or a specified pairwise longest common subsequence (LCS) distance. In some embodiments, the specified pairwise edit distance comprises a specified pairwise Hamming distance of at most two times a specified error correction capability. In some embodiments, the specified error correction capability comprises correction of 1, 2, 3, 4, or 5 substitution errors. In some embodiments, the correcting step further comprises an iterative calculation of maximum likelihood for the probability distribution to identify a candidate target oligonucleotide sequence for use in correction, and wherein the probability distribution is updated in each iteration based on the candidate target oligonucleotide sequence barcode. In some embodiments, the iterative calculation is complete when: (i) a predetermined number of iterations has been reached, (ii) the probability distribution remains substantially unchanged from one iteration to the next, or (iii) a number of corrected target oligonucleotide sequences remains substantially unchanged from one iteration to the next. In some embodiments, the probability distribution is stored as a probability table in computer memory. In some embodiments, the probability distribution is provided by probabilistic model. In some embodiments, the probabilistic model comprises a machine learning model. In some embodiments, the machine learning model comprises a random forest or neural network model. In some embodiments, a number of decoding cycles in the plurality of decoding cycles is equal to a number of segments in the target oligonucleotide sequences. In some embodiments, the target oligonucleotide sequences and barcode probe sequences comprise nucleic acid sequences. In some embodiments, the plurality of target oligonucleotide sequences is a plurality of target barcode sequences that comprises a specified total number of unique nucleic acid barcode sequences, and wherein each unique nucleic acid barcode sequence, or segment thereof, of the plurality is selected to have: a specified maximum nucleotide length; a specified minimum pairwise edit distance relative to other unique nucleic acid barcode sequences, or segments thereof, of the plurality; and at least one additional characteristic selected from a list consisting of: a specified total nucleotide length, a specified number of segments, a specified segment length, a specified upper limit on guanine-cytosine (GC) content, a specified maximum length for homopolymer subsequences, and a specified dilution factor for at least one segment. In some embodiments, the specified pairwise edit distance comprises a specified minimum pairwise Hamming distance, a specified minimum pairwise Levenshtein distance, or a specified minimum pairwise longest common subsequence (LCS) distance. In some embodiments, the specified pairwise edit distance comprises a specified minimum pairwise Hamming distance of at least two times a specified error correction capability. In some embodiments, the specified error correction capability comprises correction of 1, 2, 3, 4, or 5 substitution errors. In some embodiments, the at least one additional characteristic comprises a specified minimum number of segments of at least two. In some embodiments, the at least one additional characteristic comprises a specified minimum segment length of at least two nucleotides. In some embodiments, the at least one additional characteristic comprises a specified upper limit on guanine-cytosine (GC) content of about 50%. In some embodiments, the at least one additional characteristic comprises a specified maximum length for homopolymer subsequences of 7 nucleotides. In some embodiments, at least one segment of at least one target barcode sequence of the plurality encodes for an “OFF” state that is not visualized in at least one decoding cycle. In some embodiments, the at least one additional property comprises a specified decoding dilution factor of at least 10% for the least one segment. In some embodiments, the plurality of target barcode sequences exclude nucleic acid barcode sequences from a first designated list, or include nucleic acid barcode sequences from a second designated list. In some embodiments, each target barcode sequence of the plurality is rank-ordered according to an average pairwise edit distance from all other target acid barcode sequences of the plurality, and assigned to a corresponding target gene transcript of the same rank from a list of corresponding genes rank-ordered by relative expression level. In some embodiments, the average pairwise edit distance is an average pairwise Hamming distance, an average pairwise Levenshtein distance, or an average pairwise longest common subsequence (LCS) distance. In some embodiments, the rank-ordered unique nucleic acid barcode sequences are assigned to corresponding rank-ordered target gene transcripts such that optical crowding is reduced during a decoding process used to decode the unique nucleic acid barcode sequences. In some embodiments, the specified total number of unique nucleic acid barcode sequences is at least 1,000. In some embodiments, the specified total number of unique nucleic acid barcode sequences is at least 10,000. In some embodiments, the specified total number of unique nucleic acid barcode sequences is at least 100,000. In some embodiments, the specified total number of unique nucleic acid barcode sequences is at least 1,000,000. In some embodiments, the unique nucleic acid barcode sequences of the plurality have been incorporated into a set of target-specific probe molecules. In some embodiments, each unique nucleic acid barcode sequence is attached to a different feature of a spatial array. In some embodiments, each unique nucleic acid barcode sequence is attached to a different bead of a bead array.

Also disclosed herein are systems comprising: one or more processors; memory operably coupled to the one or more processors; and one or more programs stored in the memory that, when executed by the one or more processors, cause the system to execute a method comprising: obtaining an image for each decoding cycle of a plurality of decoding cycles to obtain a series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences based on which decoding cycle and for which locations in one or more images of the series of images the one or more respective barcode probe sequences of the plurality are detected to obtain a plurality of decoded target oligonucleotide sequences; and correcting one or more of the decoded target oligonucleotide sequences of the plurality by replacement with a known target oligonucleotide sequence, or proxy thereof, that has a maximum likelihood as computed from a probability distribution that provides probabilities for detecting a given barcode probe sequence at a given location in a given decoding cycle.

Disclosed herein are non-transitory computer-readable storage medium storing one or more programs, the one or more programs comprising instructions which, when executed by one or more processors of a computing platform, cause the computing platform to perform a method comprising: obtaining an image for each decoding cycle of a plurality of decoding cycles to obtain a series of images; detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof; decoding a plurality of target oligonucleotide sequences based on which decoding cycle and for which locations in one or more images of the series of images the one or more respective barcode probe sequences of the plurality are detected to obtain a plurality of decoded target oligonucleotide sequences; and correcting one or more of the decoded target oligonucleotide sequences of the plurality by replacement with a known target oligonucleotide sequence, or proxy thereof, that has a maximum likelihood as computed from a probability distribution that provides probabilities for detecting a given barcode probe sequence at a given location in a given decoding cycle.

Disclosed herein are arrays comprising a plurality of unique nucleic acid barcode sequences, wherein a unique nucleic acid barcode sequence, or segment thereof, of the plurality of unique nucleic acid barcode sequences has: a specified minimum pairwise edit distance of 3 relative to other unique nucleic acid barcode sequences, or segments thereof, of the array; and at least one additional characteristic selected from a list consisting of: a total length of at least 10 nucleotides, a minimum of two segments, a segment length of at least 2 nucleotides, a guanine-cytosine (GC) content of less than 50%, a maximum length for homopolymer subsequences of 7 nucleotides, and a dilution factor of at least 10% for at least one segment.

In some embodiments, the array is a spatial array and different unique nucleic acid barcode sequences are attached to different features of the spatial array. In some embodiments, the array is a bead array, and different unique nucleic acid barcode sequences are attached to different beads of the bead array. In some embodiments, a unique nucleic acid barcode sequence comprises a sequence of individual nucleotides. In some embodiments, a unique nucleic acid barcode sequence comprises a plurality of segments, and each segment comprises a plurality of nucleotides. In some embodiments, a unique nucleic acid barcode sequence comprises at most 20 segments. In some embodiments, each segment comprises at most 20 nucleotides. In some embodiments, the specified minimum pairwise edit distance comprises a specified minimum pairwise Hamming distance, a specified minimum pairwise Levenshtein distance, or a specified minimum pairwise longest common subsequence (LCS) distance. In some embodiments, the specified minimum pairwise edit distance comprises a specified minimum pairwise Hamming distance of at least two times an error correction capability, and wherein the error correction capability has a value of at least one. In some embodiments, the at least one additional characteristic comprises a guanine-cytosine (GC) content of less than about 10%. In some embodiments, the at least one additional characteristic comprises a maximum length for homopolymer subsequences of 3 nucleotides. In some embodiments, at least one segment of at least one barcode encodes for an "OFF" state that is not visualized during a decoding process used to detect and decode the nucleic acid barcode sequences. In some embodiments, the at least one additional characteristic comprises compatibility with a specified decoding dilution factor of at least 50%. In some embodiments, the unique nucleic acid barcode sequences of the array exclude nucleic acid barcode sequences from a first designated list, or include nucleic acid barcode sequences from a second designated list. In some embodiments, the array comprises at least 1,000 unique nucleic acid barcode sequences. In some embodiments, the array comprises at least 10,000 unique nucleic acid barcode sequences. In some embodiments, the array comprises at least 100,000 unique nucleic acid barcode sequences. In some embodiments, the array comprises at least 1,000,000 unique nucleic acid barcode sequences.

Also disclosed herein are compositions comprising a plurality of target-specific probe molecules, wherein a target-specific probe molecule of the plurality comprises a unique nucleic acid barcode sequence selected from a plurality of unique nucleic acid barcode sequences.

In some embodiments, the plurality of unique nucleic acid barcode sequences comprises at least 1,000 unique nucleic acid barcode sequences, and wherein a unique nucleic acid barcode sequence, or segment thereof, of the at least 1,000 unique nucleic acid barcode sequences has: a specified minimum pairwise edit distance of 3 relative to other unique nucleic acid barcode sequences, or segments thereof, of the array; and at least one additional characteristic selected from a list consisting of: a total length of at least 10 nucleotides, a minimum of two segments, a segment length of at least 2 nucleotides, a guanine-cytosine (GC) content of less than 50%, a maximum length for homopolymer subsequences of 7 nucleotides, and a dilution factor of at least 10% for at least one segment. In some embodiments, a target-specific probe molecule of the plurality further comprises a target recognition element, a unique molecular identifier, a primer binding site, a linker region, one or more detectable tags, or any combination thereof. In some embodiments, the unique nucleic acid barcode sequences of the plurality of unique nucleic acid barcode sequences are rank-ordered according to an average pairwise edit distance from all other unique nucleic acid barcode sequences of the plurality, and assigned to a corresponding target gene transcript of the same rank from a list of corresponding genes rank-ordered by relative expression level. In some embodiments, the unique nucleic acid barcode sequences of the plurality of unique nucleic acid barcode sequences are organized as a plurality of barcode tuples each comprising two unique nucleic acid barcode sequences and a pairwise edit distance between them, wherein the target gene transcripts are organized as a plurality of gene tuples each comprising two target gene transcripts and a mean expression level for their corresponding genes, and wherein the nucleic acid barcode sequences of a barcode tuple comprising the largest pairwise edit distance are assigned to the target gene transcripts of a gene tuple comprising the largest mean expression level. In some embodiments, the average pairwise edit distance is an average pairwise Hamming distance, an average pairwise Levenshtein distance, or an average pairwise longest common subsequence (LCS) distance. In some embodiments, the rank-ordered unique nucleic acid barcode sequences are assigned to corresponding rank-ordered target gene transcripts such that optical crowding is reduced during a decoding process used to decode the unique nucleic acid barcode sequences.

Disclosed herein are methods for generating barcode sequences comprising: providing a plurality of candidate barcode sequences; receiving a set of design criteria that specify a total number of unique designed barcode sequences, a maximum length for the designed barcode sequences, and a minimum pairwise edit distance for each designed barcode, or segment thereof, relative to other designed barcode sequences, or segments thereof; and applying the set of design criteria, using one or more processors and a metric tree data structure, to select a set of designed barcode sequences from the plurality of candidate barcode sequences, wherein the set of designed barcode sequences comprises the specified total number of unique barcode sequences, and wherein a unique designed barcode sequence, or segment thereof, of the set has: the specified maximum nucleotide length; and the specified minimum pairwise edit distance relative to other designed barcode sequences, or segments thereof, of the set.

In some embodiments, the designed barcode sequences comprise nucleic acid barcode sequences. In some embodiments, a unique designed barcode sequence of the set further exhibits at least one additional characteristic selected from a list consisting of: a specified minimum number of segments, a specified minimum segment length, a specified upper limit on guanine-cytosine (GC) content, a specified maximum length for homopolymer subsequences, and a specified dilution factor for at least one segment. In some embodiments, the specified minimum pairwise edit distance comprises a specified minimum pairwise Hamming distance, a specified minimum pairwise Levenshtein distance, or a specified minimum pairwise longest common subsequence (LCS) distance. In some embodiments, the specified pairwise edit distance comprises a specified minimum pairwise Hamming distance of at least two times a specified error correction capability. In some embodiments, the at least one additional characteristic comprises a specified minimum number of segments of at least two. In some embodiments, the at least one additional characteristic comprises a specified minimum segment length of at least two nucleotides. In some embodiments, the at least one additional characteristic comprises a specified upper limit on guanine-cytosine (GC) content of 50%. In some embodiments, the at least one additional characteristic comprises a specified maximum length for homopolymer subsequences of 7 nucleotides. In some embodiments, the at least one additional characteristic comprises a specified dilution factor of at least 10% for at least one segment. In some embodiments, the unique designed barcode sequences of the set exclude barcode sequences from a first designated list, or include barcode sequences from a second designated list. In some embodiments, each designed barcode sequence is rank-ordered according to an average pairwise edit distance from all other designed barcode sequences of the set, and assigned to a corresponding target gene transcript of the same rank from a list of corresponding genes rank-ordered by relative expression level. In some embodiments, the average pairwise edit distance is an average pairwise Hamming distance, an average pairwise Levenshtein distance, or an average pairwise longest common subsequence (LCS) distance. In some embodiments, the rank-ordered designed barcode sequences are assigned to corresponding rank-ordered target gene transcripts such that optical crowding is reduced during a decoding process used to decode the designed barcode sequences. In some embodiments, the specified total number of designed barcode sequences is at least 1,000. In some embodiments, the metric tree data structure comprises an M-tree data structure, a vp-tree data structure, a cover tree data structure, an MVP tree data structure, or a BK-tree data structure. In some embodiments, the designed barcode sequences are of even length, and wherein the specified pairwise edit distance relative to other designed barcode sequences of the set is determined by a determination of a pairwise edit distance for at least one of two equal halves of each designed barcode sequence. In some embodiments, the method further comprises generating a set of barcode probes configured to detect the designed barcode sequences, or segments thereof, for use in decoding the set of designed barcode sequences. In some embodiments, the method further comprises incorporating each unique designed barcode sequence of the set into a target-specific probe molecule of a set of target-specific probe molecules. In some embodiments, the method further comprises controlling a synthesis process used to manufacture the set of designed barcode sequences. In some embodiments, the method further comprises attaching each unique designed barcode sequence to a different feature of a spatial array. In some embodiments, the method further comprises attaching each unique designed barcode sequence to a different bead of a bead array.

Disclosed herein are arrays manufactured by attaching a unique nucleic acid barcode sequence to each array element of a plurality of array elements, wherein the unique nucleic acid barcode sequences are selected from a set of candidate nucleic acid barcode sequences based on the criteria that: each selected nucleic acid barcode sequence has a specified maximum nucleotide length; and each selected nucleic acid barcode sequence, or segment thereof, has a specified minimum pairwise edit distance from every other selected nucleic acid barcode sequence, or segments thereof.

In some embodiments, the array is a spatial array, the array elements comprise array features, and different unique nucleic acid barcode sequences are attached to different array features of the spatial array. In some embodiments, the array is a bead array, the array elements comprise beads, and different unique nucleic acid barcode sequences are attached to different beads of the bead array.

Also disclosed herein are system comprising: one or more processors; memory operably coupled to the one or more processors and comprising a metric tree data structure; and one or more programs stored in the memory that, when executed by the one or more processors, cause the system to execute a method comprising: providing a plurality of candidate barcode sequences; receiving a set of design criteria that specify a total number of unique designed barcode sequences, a maximum length for the designed barcode sequences, and a minimum pairwise edit distance for each designed barcode, or segment thereof, relative to other designed barcode sequences, or segments thereof; and applying the set of design criteria, using one or more processors and a metric tree data structure, to select a set of designed barcode sequences from the plurality of candidate barcode sequences, wherein the set of designed barcode sequences comprises the specified total number of unique barcode sequences, and wherein a unique designed barcode sequence of the set, or segment thereof, has: the specified maximum nucleotide length; and the specified minimum pairwise edit distance relative to other designed barcode sequences, or segments thereof, of the set.

Disclosed herein are non-transitory computer-readable storage media storing one or more programs, the one or more programs comprising instructions which, when executed by one or more processors of a computing platform, cause the computing platform to perform a method comprising: providing a plurality of candidate barcode sequences; receiving a set of design criteria that specify a total number of unique designed barcode sequences, a maximum length for the designed barcode sequences, and a minimum pairwise edit distance for each designed barcode, or segment thereof, relative to other designed barcode sequences, or segments thereof; and applying the set of design criteria, using one or more processors and a metric tree data structure, to select a set of designed barcode sequences from the plurality of candidate barcode sequences, wherein the set of designed barcode sequences comprises the specified total number of unique barcode sequences, and wherein a unique designed barcode sequence of the set, or segment thereof, has: the specified maximum nucleotide length; and the specified minimum pairwise edit distance relative to other designed barcode sequences, or segments thereof, of the set.

In some embodiments, the methods and systems described herein are operable to generate a set of designed barcodes (e.g., a set of nucleic acid barcode sequences) that satisfy a specific set of design criteria for ensuring efficient decoding and error correction capabilities. For example, in one embodiment, a system includes a processor and storage module. The storage module is operable to store a list of candidate barcodes, and the processor is operable to apply selection criteria (or filters) to the list of candidate barcodes to generate (and store in the storage module) a set of designed barcodes used to barcode a plurality of target molecules or target entities (e.g., gene sequences, gene transcripts, peptides, proteins, cells, etc.), a plurality of locations (e.g., features in a spatial array, beads in a bead array, etc.), a plurality of samples (e.g., sample 1, sample 2, sample 3, etc., in a multiplexed assay method), etc. In some embodiments, the processor is further operable to determine a length of the designed barcode sequences (e.g., an optimal length or a length required to achieve a desired level of barcode diversity), and to select barcodes from the list of candidate barcodes that have the determined length. In some embodiments, the processor is further operable to select a subset of barcodes from the list of candidate barcodes that have the determined length and/or that comprise a specified number of unique barcode sequences. In some embodiments, the processor is further operable to select a subset of barcodes from the list of candidate barcodes that have the determined length, that comprise a specified number of unique barcode sequences, and/or that exhibit a specified pairwise edit distance based on a string metric (e.g., a minimum pairwise Hamming distance of more than two times a specified error correction factor).

In some embodiments, the methods and systems described herein are further operable to assign barcodes from a set of designed barcodes to, e.g., a set of target molecules, locations, or samples, to direct the synthesis of a set of designed barcodes or barcoded reagents, and/or to direct the deposition and/or attachment of barcodes to, e.g., locations in a spatial array or beads in a bead array. For example, in some embodiments, the system further comprises a barcoding module operable to assign barcodes from a set of designed barcodes (e.g., the subset of candidate barcodes that meet a specific set of design criteria) to a set of target molecules, locations, or samples, to direct the synthesis of a set of designed barcodes or barcoded reagents (e.g., by interfacing with an automated oligonucleotide or peptide synthesizer), and/or to direct the deposition and/or attachment of barcodes to, e.g., beads in a bead array or locations in a spatial array or beads in a bead array (e.g., by interfacing to an automated microarray spotting instrument).

In some embodiments, the methods and systems described herein are further operable to generate a decoding process that is matched to the set of designed barcodes. For example, in some embodiments, the system further comprises a decoding module operable to, for example, associate a color channel in an imaging system with a labeled barcode probe sequence used to detect and decode a barcode sequence, or segment thereof (e.g., to detect one or more nucleotides (corresponding to letters) that collectively constitute a segment (corresponding to a code word) of a complete nucleic acid barcode sequence), and to generate a series of decoding cycles for detecting and decoding a plurality of barcode sequences, where each decoding cycle comprises the use of a plurality of barcode probe sequences to detect a plurality of nucleic acid barcode segments.

In some embodiments, the methods and systems described herein are operable to provide for error correction of detected and decoded barcode sequences using one or more of the error correction methods described. For example, in one embodiment, the system further comprises an error correction module operable to identify and correct errors in the detected and decoded barcode sequences by replacing one or more of the detected and decoded barcode sequences with a corresponding designed barcode that has a closest Hamming distance to a given detected and decoded barcode sequence.

In another embodiment, the system further comprises an error correction module operable to identify and correct errors in the detected and decoded barcode sequences by replacing one or more of the detected and decoded barcode sequences with a corresponding designed barcode sequence that has a maximum likelihood as computed from the log likelihood (or negative log likelihood) of a probabilistic model that is stored in the storage module and provides probabilities for detecting a given barcode sequence, or segment (code word) thereof (e.g., using a complementary barcode probe) at a given location in a given decoding cycle based on a set of detected signals (e.g., fluorescence signals).

In yet another embodiment, the system further comprises an error correction module operable to identify and correct errors in the detected and decoded barcode sequences by replacing one or more of the detected and decoded barcode sequences with a corresponding designed barcode sequence that: (i) is within a predetermined pairwise edit distance (e.g., a predetermined pairwise Hamming distance) from the detected and decoded barcode sequence (determined, for example, by rank-ordering the set of designed barcode sequences according to their pairwise edit distance from the detected and decoded barcode sequence), and (ii) has a maximum likelihood as computed from the log likelihood (or negative log likelihood) of a probabilistic model that is stored in the storage module and provides probabilities for detecting a given barcode sequence, or segment (code word) thereof (e.g., using a complementary barcode probe) at a given location in a given decoding cycle based on a set of detected signals (e.g., fluorescence signals).

In some embodiments, the methods and systems described herein are operable to provide for iterative error correction of detected and decoded barcode sequences and/or for determining the accuracy of a decoding method. For example, in one embodiment, the system further comprises an error correction module operable to, for each detected and decoded barcode sequence and until convergence, repeatedly: correct the detected and decoded barcode sequence with one of the stored designed barcodes that has a maximum likelihood as computed from the log likelihood (or negative log likelihood) of a probabilistic model that is stored in the storage module and provides probabilities for detecting a given barcode sequence, or segment (code word) thereof (e.g., using a complementary barcode probe) at a given location in a given decoding cycle based on a set of detected signals (e.g., fluorescence signals); and update the probabilistic model in the storage module using the corrected barcode sequence. In some embodiments, the error correction module is further operable to, after convergence, correct each previously corrected barcode sequence with one of the designed barcodes that has a maximum likelihood as computed from the log likelihood (or negative log likelihood) of the updated probabilistic model. Convergence of the iterative error correction process may comprise, e.g., at least one of: (i) reaching a predetermined number of repetitions, (ii) reaching a number of repetitions where the probabilistic model remains substantially unchanged from one repetition to the next, or (iii) reaching a repetition for which the number of corrected barcode sequences remains substantially unchanged from a previous repetition.

In another embodiment, the system further comprises an error correction module operable to, for each detected and decoded barcode sequence and until convergence, repeatedly: provide probabilities for correcting the detected and decoded barcode sequence with any one of the stored designed barcodes that (i) has a maximum likelihood as computed from the log likelihood (or negative log likelihood) of a probabilistic model that is stored in the storage module and provides probabilities for detecting a given barcode sequence, or segment (code word) thereof (e.g., using a complementary barcode probe) at a given location in a given decoding cycle based on a set of detected signals (e.g., fluorescence signals); and update the probabilistic model in the storage module using the corrected barcode sequence. In some embodiments, the error correction module is further operable to, after convergence, correct each previously corrected barcode sequence with one of the designed barcodes that: (ii) is within a predetermined pairwise edit distance (e.g., a predetermined pairwise Hamming distance) of the previously corrected barcode sequence, and (iii) has a maximum likelihood as computed from the log likelihood (or negative log likelihood) of the updated probabilistic model. Convergence of the iterative error correction process may comprise, e.g., at least one of: (i) reaching a predetermined number of repetitions, (ii) reaching a number of repetitions where the probabilistic model remains substantially unchanged from one repetition to the next, or (iii) reaching a repetition for which the number of corrected barcode sequences remains substantially unchanged from a previous repetition.

In yet another embodiment, the system further comprises an error correction module operable to, for each detected and decoded barcode sequence and until convergence, repeatedly: provide probabilities for correcting the detected and decoded barcode sequence with any one of the stored designed barcodes that: (i) is within a predetermined pairwise edit distance (e.g., a predetermined pairwise Hamming distance) from the detected and decoded barcode sequence (determined, for example, by rank-ordering the set of designed barcode sequences according to their pairwise edit distance from the detected and decoded barcode sequence), and (ii) has a maximum likelihood as computed for a set of nearest neighbor designed barcodes from a log likelihood (or negative log likelihood) of a probabilistic model that is stored in the storage module and provides probabilities for detecting a given barcode sequence, or segment (code word) thereof (e.g., using a complementary barcode probe) at a given location in a given decoding cycle based on a set of detected signals (e.g., fluorescence signals); and update the probabilistic model in the storage module using the corrected barcode sequence. In some embodiments, the error correction module is further operable to, after convergence, correct each previously corrected barcode sequence with one of the designed barcodes that: (iii) is within a predetermined pairwise edit distance (e.g., a predetermined pairwise Hamming distance) of the previously corrected barcode sequence, and (iv) has a maximum likelihood as computed for the set of nearest neighbor designed barcodes from the log likelihood (or negative log likelihood) of the updated probabilistic model. Convergence of the iterative error correction process may comprise, e.g., at least one of: (i) reaching a predetermined number of repetitions, (ii) reaching a number of repetitions where the probabilistic model remains substantially unchanged from one repetition to the next, or (iii) reaching a repetition for which the number of corrected barcode sequences remains substantially unchanged from a previous repetition.

In some embodiments, the methods and systems described herein are operable to provide for barcoding gene sequences or transcripts thereof (or other analytes in a biological sample) in a manner that reduces the number of false positive barcode corrections and minimizes optical crowding when using imaging-based decoding methods to decode barcodes associated with both highly expressed genes and lower expressed genes in a biological sample. In one embodiment, for example, a system includes a processor and a storage module. The storage module is operable to store a list of candidate barcodes, and the processor is operable to apply selection criteria (or filters) to the list of candidate barcodes to generate the set of designed barcodes used to barcode a plurality of, e.g., gene transcripts. The designed barcodes (or designed barcode pool) may be used to create a plurality of barcode probes with each barcode probe being configured to target one of a plurality of gene transcripts in a sample. The system may also include a barcoding module operable to (i) rank the designed barcodes according to pairwise edit distances (e.g., pairwise Hamming distances) between the designed barcodes, (ii) rank the genes for which transcripts are to be barcoded according to the expression levels of the genes in a sample, (iii) assign each corresponding gene transcript to one of the designed barcodes according to the same rank-ordering, and/or (iv) direct the encoding of probe molecules designed to hybridize to the gene transcripts with their assigned barcode.

In another embodiment, the system comprises a barcoding module operable to generate tuples of the designed barcodes. Each tuple of designed barcodes comprises an edit distance (e.g., a Hamming distance) between the two barcodes used to form the tuple. The barcoding module is also operable to generate tuples of gene sequences or gene transcripts to be encoded with the barcodes, where each tuple of gene sequences or transcripts includes a mean expression level for the genes in the tuple. The barcoding module identifies a first of the tuples of genes having a largest mean expression level, assigns the identified first tuple of genes to a first of the tuples of barcodes having a largest edit distance (e.g., Hamming distance), and directs encoding of one of the gene sequences or transcripts of the first tuple with one of the designed barcodes of the assigned tuple of barcodes and the encoding of the other gene sequence or transcript with the other of the designed barcodes of the assigned tuple of barcodes.

In some embodiments, a first barcode of the first tuple of designed barcodes has a larger average edit distance (e.g., a larger average Hamming distance) to the remaining barcodes of the plurality of the designed barcodes than a second barcode of the first tuple of designed barcodes, and a first gene sequence or transcript of the first tuple of genes corresponds to a gene that has a larger expression level than a second gene of the first tuple of genes. The first gene sequence or transcript of the first tuple of genes may be assigned to the first barcode of the first tuple of designed barcodes, and the second gene sequence or transcript of the first tuple of genes may be assigned to the second barcode of the first tuple of designed barcodes. In some embodiments, the barcoding module is further operable to, in identifying the first tuple of genes and assigning designed barcodes to the identified first tuple of genes, determine that the first tuple of barcodes has no barcodes assigned to any of the tuples of genes.

While the methods and systems described herein are generally directed to the barcoding of gene sequences or gene transcripts, these methods and systems may also be advantageously used to assign barcodes to other analytes, such as proteins, accessible chromatin, other genomic DNA sequences, etc.

In some embodiments, the methods and systems described herein are operable to align images generated over a plurality of decoding cycles based on the detected locations of barcode segments (code words) and barcode sequences in the images. For example, in one embodiment, a system includes a processor and a storage module. The storage module is operable to store a list of candidate barcodes, and the processor is operable to apply selection criteria (or filters) to the list of candidate barcodes to generate the set of designed barcodes used to barcode a plurality of target molecules or target entities, a plurality of locations, a plurality of samples, etc., as described above. In some embodiments, the system includes a decoding module operable to generate a series of decoding cycles for detecting and decoding a plurality of barcode sequences, as described above. In some embodiments, the system also includes an error correction module operable to identify and correct errors in the detected and decoded barcode sequences, and to identify one or more of the corrected barcode sequences that have a predetermined quality score or degree of correction. In some embodiments, the system also includes an imaging module operable to generate an image for each decoding cycle, to register the images from the decoding cycles to each other based on locations of (i) the identified one or more of the corrected barcode sequences that meet the predetermined quality score or degree of confidence in the images, (ii) one or more corrected barcodes that match one or more predefined barcode sequences, (iii) one or more randomly selected corrected barcode sequences, and/or (iv) the entire set of corrected barcode sequences, and to align the images based on the registration.

In some embodiments, the methods and systems described herein are operable to stitch together adjacent image tiles to create a composite image of imaged barcoded target analytes (or other barcoded entities) in a sample that has a larger field-of-view. For example, in one embodiment, a system includes a processor and a storage module. The storage module is operable to store a list of candidate barcodes, and the processor is operable to apply selection criteria (or filters) to the list of candidate barcodes to generate the set of designed barcodes used to barcode a plurality of target molecules or target entities, a plurality of locations, a plurality of samples, etc., as described above. In some embodiments, the system includes a decoding module operable to generate a series of decoding cycles for detecting and decoding a plurality of barcode sequences, as described above. In some embodiments, the system also includes an error correction module operable to identify and correct errors in the detected and decoded barcode sequences, and to identify one or more of the detected and decoded barcode sequences that have a predetermined degree of correction, as described above. In some embodiments, the system also includes an imaging module operable to generate an image tile for each decoding cycle; identify at least a subset of the detected and decoded barcode sequences in one image tile that corresponds to detected and decoded barcode sequences in an overlapping region of another image tile; and stitch the image tiles together based on the identified subset of the detected and decoded barcode sequences.

The various embodiments disclosed herein may be implemented in a variety of ways as a matter of design choice. For example, some embodiments herein are implemented in hardware whereas other embodiments may include processes that are operable to implement and/or operate the hardware. Other exemplary embodiments, including software and firmware, are described below.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments are now described, by way of example only, and with reference to the accompanying drawings. The same reference number represents the same element or the same type of element on all drawings.

DETAILED DESCRIPTION

Figure 1:
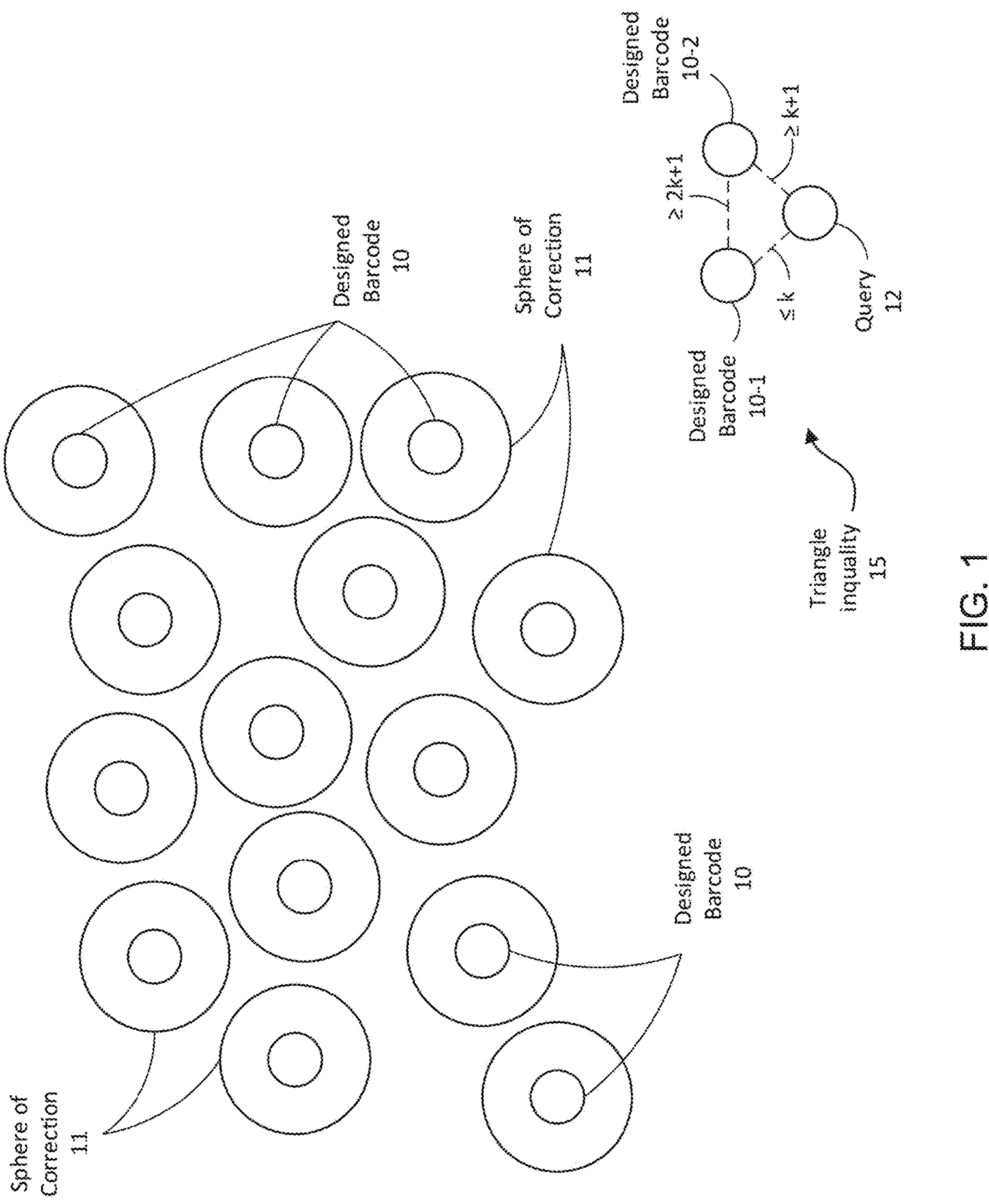
FIG. 1 is a block diagram of an exemplary designed barcode space with spheres of correction.

The figures and the following description illustrate specific exemplary embodiments. It will thus be appreciated that those skilled in the art will be able to devise various arrangements that, although not explicitly described or shown herein, embody the principles of the embodiments. Furthermore, any examples described herein are intended to aid in understanding the principles of the embodiments and are to be construed as being without limitation to such specifically recited examples and conditions. As a result, this disclosure is not limited to the specific embodiments or examples described below.

In many genomic applications, barcodes are used to label certain target nucleotide sequences, e.g., target gene sequences or transcripts corresponding to target gene sequences. Genomic information may then be associated with those targets. For example, in single cell applications, single cells may be partitioned such that each partition receives a single cell and a barcoded bead. Nucleic acid molecules released from the single cell upon lysis can be captured by barcoded probes attached to the bead, transcribed and amplified, and pooled such that genomic data derived via next-generation sequencing (NGS) can be associated with the single cell in a given partition and analyzed statistically. In spatial genomics enabled by, for example, barcoded bead arrays, the barcodes encode the positions of beads in the array after the beads have been distributed randomly on the array. Optical decoding of these beads reveals a spatial barcode at each bead position in the array. The decoding process may, however, be noisy. Thus, the decoded barcodes detected by optical readout may often require error correction. In in-situ transcriptomics approaches (and other in-situ omics applications), genes or gene transcripts (and/or other target analytes, such as peptides, proteins, cells, etc.) are targeted and labeled with nucleic acid barcode sequences that can also be optically decoded. The mechanism of attaching a barcode to a target analyte varies based on the platform, but the barcodes attached to these target analytes are the messages (e.g., from the mobile phone analogy) that are to be detected by the decoding process.

Terminology

Specific terminology is used throughout this disclosure to explain various aspects of the methods, systems, and compositions that are described. Unless otherwise defined, other technical terms used herein have the same meaning as commonly understood by one of ordinary skill in the art in the field to which this disclosure belongs.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, un-recited additives, components, integers, elements or method steps.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

As used herein, the term "specified" may indicated a value or number input by a user, or a value or number determined by an algorithm, e.g., a barcode design algorithm, a barcode error correction algorithm, an image registration algorithm, or an image tile stitching algorithm.

Barcodes & Decoding:

A "barcode" is a label, or identifier, that conveys or is capable of conveying information (e.g., information about an analyte in a sample, a cell, a bead, a location, a sample, and/or a capture probe). As used herein, the term "barcode" may refer either to a chemical/physical barcode molecule (e.g., a nucleic acid barcode molecule) or to its representation in a computer-readable, digital format (e.g., as a string of characters representing the sequence of bases in a nucleic acid barcode molecule).

As used herein, the phrase "barcode diversity" refers to the total number of unique barcode sequences that may be represented by a given set of barcodes.

As used herein, a "chemical barcode" (or "chemical barcode sequence") is a physical molecule that forms a label or identifier as described above. In some instances, a chemical barcode can be part of an analyte, can be independent of an analyte, can be attached to an analyte, or can be attached to or part of a probe that targets the analyte. In some instances, a particular barcode can be unique relative to other barcodes.

Chemical barcodes can have a variety of different formats. For example, chemical barcodes can include polynucleotide barcodes, random nucleic acid and/or amino acid sequences, and synthetic nucleic acid and/or amino acid sequences. A chemical barcode can be attached to an analyte, or to another moiety or structure, in a reversible or irreversible manner. A chemical barcode can be added to, for example, a fragment of a deoxyribonucleic acid (DNA) or ribonucleic acid (RNA) sample before or during sequencing of the sample. In some instances, chemical barcodes can allow for identification and/or quantification of individual sequencing-reads in sequencing-based methods (e.g., a barcode can be or can include a unique molecular identifier or "UMI"). Chemical barcodes can be used to detect and spatially-resolve molecular components found in biological samples, for example, at single-cell resolution (e.g., a chemical barcode can be, or can include, a molecular barcode, a spatial barcode, a unique molecular identifier (UMI), etc.).

In some instances, chemical barcodes may comprise a series of two or more segments or sub-barcodes (e.g., corresponding to "letters" or "code words" in a decoded barcode), each of which may comprise one or more of the subunits or building blocks used to synthesize the chemical barcode molecules. For example, a nucleic acid barcode molecule may comprise two or more barcode segments, each of which comprises one or more nucleotides. In some instances, a chemical barcode may comprise at least 1, 2, 3, 4, 5, 6, 7, 8, 9, 10, or more than 10 segments. In some instances, each segment of a chemical barcode molecule may comprise at least 1, 2, 3, 4, 5, 6, 7, 8, 9, 10, 12, 14, 16, 18, 20, or more than 20 subunits or building blocks. For example, each segment of a nucleic acid barcode molecule may comprise at least 1, 2, 3, 4, 5, 6, 7, 8, 9, 10, 12, 14, 16, 18, 20, or more than 20 nucleotides. In some instances, two or more of the segments of a chemical barcode may be separated by non-barcode segments, i.e., the segments of a chemical barcode molecule need not be contiguous.

Examples of chemical barcodes and their applications include, but are not limited to, target barcodes (e.g., chemical barcode molecules that form unique labels or identifiers associated with target analyte molecules), cell barcodes (e.g., chemical barcode molecules that form unique labels or identifiers associated with individual cells), spatial barcodes (e.g., chemical barcode molecules that form unique labels or identifiers associated with specific locations (e.g., locations in a spatial array, a bead array, etc.)), and sample barcodes (e.g., chemical barcode molecules that form unique labels or identifiers associated with individual samples (e.g., for multiplexing purposes).

As used herein, a “digital barcode” (or “digital barcode sequence”) is a representation of a corresponding chemical barcode (or target analyte sequence) in a computer-readable, digital format as described above. A digital barcode may comprise one or more “letters” (e.g., 1, 2, 3, 4, 5, 6, 7, 8, 9, 10, 12, 14, 16, 18, 20, or more than 20 letters) or one or more “code words” (e.g., 1, 2, 3, 4, 5, 6, 7, 8, 9, 10, or more than 10 code words), where a “code word” comprises, e.g., 1, 2, 3, 4, 5, 6, 7, 8, 9, 10, 12, 14, 16, 18, 20, or more than 20 letters. In some instances, the sequence of letters or code words in a digital barcode sequence may correspond directly with the sequence of building blocks (e.g., nucleotides) in a chemical barcode. In some instances, the sequence of letters or code words in a digital barcode sequence may not correspond directly with the sequence of building blocks in a chemical barcode, but rather may comprise, e.g., arbitrary code words that each correspond to a segment of a chemical barcode. For example, in some instances, the disclosed methods for decoding and error correction may be applied directly to detecting target analyte sequences (e.g., mRNA sequences) as opposed to detecting target barcodes, and the barcode probes used to detect the target analyte sequences may correspond to letters or code words that have been assigned to specific target analyte sequences but that do not directly correspond to the target analyte sequences.

As used herein a “designed barcode” (or “designed barcode sequence”) is a chemical barcode (or its digital equivalent; in some instances a designed barcode may comprise a series of code words that can be assigned to gene transcripts and subsequently decoded into a decoded barcode) that meets a specified set of design criteria as required for a specific application. In some instances, a set of designed barcodes may comprise at least 2, at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least 10', at least $10^8$, at least $10^9$, or more than $10^9$ unique barcodes. In some instances, a set of designed barcodes may comprise any number of designed barcodes within the range of values in this paragraph, e.g., 1,225 unique barcodes or $2.38\times10^6$ unique barcodes. As noted above for barcodes in general, in some instances designed barcodes may comprise two or more segments (corresponding to two or more code words in a decode barcode). In those cases, the specified set of design criteria may be applied to the designed barcodes as a whole, or to one or more segments (or positions) within the designed barcodes.

As used herein, a “decoding process” is a process comprising a plurality of decoding cycles in which different sets of barcode probes are contacted with target analytes (e.g., mRNA sequences) or target barcodes (e.g., barcodes associated with target analytes) present in a sample or on an array, and used to detect the target sequences or associated target barcodes, or segments thereof. In some instances, the decoding process comprises acquiring one or more images (e.g., fluorescence images) for each decoding cycle. Decoded barcode sequences are then inferred based on a set of physical signals (e.g., fluorescence signals) detected in each decoding cycle of a decoding process. In some instances, the set of physical signals (e.g., fluorescence signals) detected in a series of decoding cycles for a given target barcode (or target analyte sequence) may be considered a “signal signature” for the target barcode (or target analyte sequence). In some instances, a decoding process may comprise, e.g., 1, 2, 3, 4, 5, 6, 7, 8, 9, 10, or more than 10 decoding cycles. In some instances, each decoding cycle may comprise contacting a plurality of target sequences or target barcodes with 1, 2, 3, 4, 5, 6, 7, 8, 9, 10, or more than 10 barcode probes (e.g., fluorescently-labeled barcode probes) that are configured to hybridize or bind to specific target sequences or target barcodes, or segments thereof. In some instances, a decoding process may comprise performing a series of in situ barcode probe hybridization steps and acquiring images (e.g., fluorescence images) at each step. Systems and methods for performing multiplexed fluorescence in situ hybridization and imaging are described in, for example, WO 2021/127019 A1; U.S. Pat. No. 11,021,737; and PCT/EP2020/065090 (WO2020240025A1), each of which is incorporated herein by reference in its entirety.

As used herein, a “decoded barcode” (or “decoded barcode sequence”) is a digital barcode sequence generated via a decoding process that ideally matches a designed barcode sequence, but that may include errors arising from noise in the synthesis process used to create chemical barcodes and/or noise in the decoding process itself. As noted above, in some instances, the disclosed methods for decoding and error correction may be applied directly to detecting target analyte sequences (e.g., mRNA sequences0 as opposed to detecting target barcodes, and the barcode probes used to detect the target analyte sequences may correspond to letters or code words that have been assigned to specific target analyte sequences but that do not directly correspond to the target analyte sequences. In these instances, a decoded barcode (i.e., a series of letters or code words) may serve as a proxy for the target analyte sequence.

As used herein, a “corrected barcode” (or “corrected barcode sequence”) is a digital barcode sequence derived from a decoded barcode sequence by applying one or more error correction methods.

Probes:

A “probe” is a molecule designed to recognize (and bind or hybridize to) another molecule, e.g., a target analyte, another probe molecule, etc. As used herein, the term “probe” may refer either to a chemical/physical probe molecule (e.g., a nucleic acid probe molecule) or to its representation in a computer-readable, digital format (e.g., as a string of characters representing the sequence of bases in a nucleic acid probe molecule).

In some instances, a chemical probe molecule may comprise (i) a target recognition element (e.g., an antibody capable of recognizing and binding to a target peptide, protein, or small molecule; an oligonucleotide sequence that is complementary to a target gene sequence or gene transcript; or a poly-T oligonucleotide sequence that is complementary to the poly-A tails on messenger RNA molecules), (ii) a barcode element (e.g., a molecular barcode, a cell barcode, a spatial barcode, and/or a unique molecular identifier (UMI)), (iii) an amplification and/or sequencing primer binding site, (iv) one or more linker regions, (v) one or more detectable tags (e.g., fluorophores), or any combination thereof. In some instances, each component of a chemical probe molecule may comprise at least 1, 2, 3, 4, 5, 6, 7, 8, 9, 10, 12, 14, 16, 18, 20, or more than 20 subunits or building blocks. For example, in some instances, each component of a nucleic acid probe molecule may comprise at least 1, 2, 3, 4, 5, 6, 7, 8, 9, 10, 12, 14, 16, 18, 20, or more than 20 nucleotides.

In some instances, chemical probes may bind or hybridize directly to their target. In some instances, chemical probes may bind or hybridize indirectly to their target. For example, in some instances, a secondary probe may bind or hybridize to a primary probe, where the primary probe binds or hybridizes directly to the target analyte. In some instances, a tertiary probe may bind or hybridize to a secondary probe, where the secondary probe binds or hybridizes to a primary probe, and where the primary probe binds or hybridizes directly to the target analyte.

Examples of "probes" and their applications include, but are not limited to, capture probes (e.g., molecules designed to recognize and bind or hybridize to another molecule (e.g., a target analyte) and separate it from a sample or mixture; capture probes often attached to magnetic beads, a spatial array support surface, etc.), detection probes: physical molecules used to recognize and bind/hybridize to another molecule, e.g., a target analyte or a portion of a capture probe; typically labeled with a fluorophore or other detectable tag As used herein, a "barcode probe" (or "barcode probe sequence") is a chemical probe molecule (or its digital equivalent) designed to recognize (and bind or hybridize to) a chemical barcode sequence (or segments thereof). In some instances, a barcode probe may be used to detect and decode a barcode, e.g., a nucleic acid barcode. In some instances, a barcode probe may bind or hybridize directly to a target barcode. In some instances, a barcode probe may bind or hybridize indirectly to a target barcode (e.g., by binding or hybridizing to a another probe molecules which itself is bound or hybridized to the target barcode).

Nucleic Acid Molecules and Nucleotides:

The terms "nucleic acid" (or "nucleic acid molecule") and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

String Metrics and Edit Distances:

As used herein, a "string metric" is a numerical value that measures a distance between two strings (e.g., text strings) in a metric space that satisfies the triangle inequality constraint, and that may be used for string matching or comparison.

As used herein, an "edit distance" is a numerical value that quantifies how different two strings (e.g., text strings) are from one another by counting the minimum number of editing operations required to transform one string into the other. Examples of edit distance metrics include, but are not limited to, Hamming distance, Levenshtein distance, longest common subsequence (LCS) distance, and the like. For example, the Levenshtein distance between two strings is the minimum number of single-character edits (e.g., insertions, deletions, or substitutions) required to transform one string into the other. The longest common subsequence (LCS) distance is the edit distance for which the only allowed edit operations are insertions and deletions, each of which is assigned a unit cost. The Hamming distance between two strings of equal length (i.e., substitutions are the only edit operations allowed) is the number of positions in the two strings at which the corresponding symbols are different.

The section headings used herein are for organizational purposes only and are not to be construed as limiting the subject matter described.

Barcode Design

For many biomolecule detection or nucleic acid sequencing applications, a set of 1 . . . D unique items of information (e.g., target entities (or messages in the context of the mobile phone analogy) which may comprise, e.g., positions in bead arrays, gene sequences or transcripts for in situ transcriptomics, or the identities of target analytes present in a sample, etc.) are labeled in a 1:1 manner with unique barcodes drawn from a set of chemical barcodes X of length L via some encoding function which, in many cases, may comprise a random assignment of barcodes to the target entities. One problem with conventional barcoding schemes is that barcode designs are not intimately tied with the decoding process used to detect and decode the barcodes. That is, a noisy decoding process used to detect and decode the barcodes may introduce errors such that a set of one or more decoded barcodes Y are read out instead of one or more barcodes of the set of chemical barcodes X Often, a noise decoding process may introduce errors that conventional decoding processes may not be able to correct.

To illustrate, consider the following example. The diversity D of target entities (e.g., messages) that can be encoded (and subsequently decoded) by a set of barcodes of length L comprised of letters drawn from an alphabet A of size N (e.g., the four "letters" are $\mathcal{A}$={A, T, G, C} in naturally-occurring DNA sequences) is $N^L$ (i.e., the number of unique barcodes that are possible). If the target diversity is D, then in information theory terms, the transfer rate is $R=D/N^L$. The Shannon capacity of the noisy channel (e.g., the decoding process) is $C=\sup_{\mathbb{P}(X)} I(X;Y)$, a mathematically well-defined property that is fully determined by the probabilistic error model $\mathbb{P}(Y|X)$. This quantitatively captures the maximum information about X that can be learned from Y. Shannon's theorem predicts that near perfect error correcting codes (e.g., with no false-positive corrections) exist if the transfer rate R is less than the capacity C of the channel. Thus, if the capacity C is small due to large error rates and/or a noisy channel, larger redundancies (e.g., a larger L representing longer barcodes) may be used to encode the same target diversity and thereby lower the transfer rate. So, target diversity D may be represented as $D=\mathcal{O}(CN^L)$. The capacity C is estimated using experiment data and a deep understanding of the error model that governs the communication channel (or decoding process). In general, it can be difficult to obtain exact values for real world decoding processes. But, error correction methods used in conjunction with efficient barcoding schemes (e.g., using barcodes of small L), can produce false-positive correction rates that are tolerably small.

Many coding schemes, such as parity check codes and Hamming codes, are designed for the binary case where the alphabet A={0, 1}. These codes may provide relatively good theoretical guarantees for error correction capability where the error model for transmission is analytically well understood and where capacity is mathematically known (e.g., such as for Gaussian communication channels). Some of these coding schemes may be implemented in the encoding and/or decoding schemes for biological barcoding processes. For example, in some embodiments, barcodes may comprise DNA sequences synthesized by ligation of two sequence segments (e.g., each segment being 8 bases in length). Together, they form a chemical barcode that is 16 bases in length. In this regard, the set of sequences for segment A may be designed such that the minimum pairwise Hamming distances ($H_D$) between sequences is $H_D \geq 2$, while the set of sequences for segment B may be chosen arbitrarily such that the minimum pairwise $H_D$ over the full 16 bases is at least 2, as guaranteed by the segment A design. The total diversity (i.e., the number of unique barcode sequences) of the chemical barcode set for genomics applications is often in the low millions. For some genomics applications, e.g., when sequencing is used for the barcode readout process, the error model for barcode readout is essentially a predominant short read sequencer error model (e.g., typically dominated by substitution errors where one nucleotide base is substituted for another). Modern commercial nucleic acid sequencers can attain 99.9% single base accuracy and sequencing, which means the substitution error rate is 0.1%. The number of substitution errors that may occur are distributed binomially (e.g., under an uncorrelated model) from ~Binom(n=16, p=0.001). Accordingly in this scenario the majority of sequenced barcodes have no errors.

Instead of using the binary alphabet A={0,1} of electronic communications, assume there is an alphabet of size N. The problem of barcode design is about generating D unique barcodes of length L from an alphabet of size N such that the barcode design affords relatively good error correction guarantees over the range of expected error rates. If the decoding processes are noisy (e.g., noisier than nucleic acid sequencing), the barcodes should be longer to afford better correction while attaining the same diversity. The question of how one can chemically embed such barcodes made up of letters other than the A, T, G, C for naturally occurring DNA sequences is addressed below and can be application specific.

First, there are several ways to evaluate a distance $d(X_1, X_2)$ between two strings $X_1$, $X_2$ (e.g., barcodes). For a distance to qualify as a "string metric", the distance should: (i) satisfy the triangle inequality of $d(X_1, X_2) \leq d(X_1, X_3)+d(X_3, X_2)$; (ii) be symmetric such that $d(X_1, X_2)=d(X_2, X_1)$; and (iii) satisfy a non-negativity constraint with $d(X_1, X_2)=0$ if $X_1=X_2$. One class of distance metrics are known as edit distances, which allow for three kinds of edit operations on letters of one string (or sequence) to transform it into the other string (or sequence) (e.g., via substitution, insertion, or deletion of a single letter). Each operation is penalized and the edit distance between the two strings is equal to a minimum total penalty of transforming one string to another using these permitted operations. To use the edit distance as a string metric, the insertion and deletion penalty should be the same so as to satisfy the symmetry condition. This assumes the decoding processes do not introduce translocation errors. Table 1 illustrates the details of the edit distance ($E_D$) and special cases of the edit distance, e.g., the Hamming distance ($H_D$), the longest common subsequence distance ($LCS_D$), and the Levenshtein distance ($Lev_D$) that may be calculated for a designed barcode set via dynamic programming.

TABLE 1

Edit distance characteristics

| $d/(X_1, X_2)$ | $p_{ins}$ | $p_{del}$ | $p_{sub}$ | bounds |
|---|---|---|---|---|
| Edit ($E_D$) | $p_0$ | $p_0$ | $p_1$ | $\lvert\lvert X_1\rvert - \lvert X_2\rvert\rvert p_0 \leq d(X_1, X_2) \leq \lvert\lvert X_1\rvert - \lvert X_2\rvert\rvert p_0 + \min(\lvert X_1\rvert, \lvert X_2\rvert)p_1$ |
| Hamming ($H_D$) | ∞ | ∞ | 1 | $d(X_1, X_2) \leq \lvert X_1\rvert = \lvert X_2\rvert$ |
| LCS ($LCS_D$) | 1 | 1 | ∞ | $d(X_1, X_2) \leq \lvert X_1\rvert + \lvert X_2\rvert$<br>$d(X_1, X_2) \leq H_D(\lvert X_1\rvert, \lvert X_2\rvert)$ |
| Levenshtein ($Lev_D$) | 1 | 1 | 1 | $d(X_1, X_2) \leq \lvert X_1\rvert + \lvert X_2\rvert$<br>$d(X_1, X_2) \leq H_D(\lvert X_1\rvert, \lvert X_2\rvert)$<br>$d(X_1, X_2) \leq LCS_D(\lvert X_1\rvert, \lvert X_2\rvert)$<br>$d(X_1, X_2) \geq \lvert\lvert X_1\rvert - \lvert X_2\rvert\rvert$ |

In Table 1, $p_{ins}$, $p_{del}$, and $p_{sub}$ are the error penalties for insertion, deletion, or substitution of a single letter, respectively, and the bounds column indicates the corresponding pairwise relationships between two strings $X_1$ and $X_2$ and properties for the Edit distance ($E_D$), Hamming distance ($H_D$), longest common subsequence distance ($LCS_D$), and Levenshtein distance ($Lev_D$). The Levenshtein distance allows deletion, insertion and substitution. The longest common subsequence distance allows insertion and deletion, but not substitution (i.e., substitution comprises an "infinite" penalty). The Hamming distance allows only substitution, and hence only applies to strings (or sequences) of the same length.

FIG. 1 illustrates a set of designed barcodes 10 that have been designed to enable efficient error correction and their corresponding spheres of correction 11 in edit space. The space filling barcodes 10 may be designed to correct an error penalty of up to k when the minimum pairwise edit distance is greater than 2k. For example, due to the triangle inequality satisfied by edit distances, these barcodes may unambiguously be corrected for up to k errors when a query barcode (or decoded barcode) is closer than k to at most one design barcode 10 in edit distance space. For Hamming distances $H_D$, correctable errors are limited to substitution errors, while for edit distances more generally, correctable errors may include substitutions, insertions, and deletions.

As an example, consider a barcode of length L (while some barcodes may be designed with a fixed length L, barcode design and decoding embodiments described herein are extensible to the general case). By definition, a barcode of length L is a sequence of L letters drawn from alphabet A. A barcode with no design constraints could be any of $N^L$ different sequences. In some instances, sets of letters $\hat{\mathcal{A}}_1 \ldots \hat{\mathcal{A}}_L \subset \hat{\mathcal{A}}$ may be established such that the letter in position i may be drawn from the letter set $A_i$. Thus, the full barcode sequence is given by $X \in \hat{\mathcal{A}}_1 \times \ldots \times \hat{\mathcal{A}}_L$. In the nucleic acid sequencing case, $\hat{\mathcal{A}}_i = \mathcal{A} = \{A, T, G, C\}$ with the decoding step for each position being able to sample all four letters (e.g., a type of "dense decoding" as will be explained in greater detail below).

Now, generate the maximum number of discrete barcode strings that can be drawn from $\hat{\mathcal{A}}_1 \times \ldots \times \hat{\mathcal{A}}_L$. Then, select the subset of those barcodes such that the minimum pairwise distance between any two barcodes of the subset is >2k, where k is the maximum number of errors that can be corrected. FIG. 1 illustrates each selected (i.e., designed) barcode as having a sphere of radius k which is not overlapping with any other designed barcode. An observed barcode Y (e.g., a decoded barcode) can be queried against the designed barcode set X to determine relatively close matches. In particular, error correction for the queried (or decoded) barcodes may comprise finding the nearest designed barcodes X1, X2 (10-1, 10-2) and confirming that, if a query barcode Y (12) is closer than a distance k to the barcode X1 (10-1), for example, the barcode Y should be further than k from the other barcode X2 (10-2), as guaranteed by triangle inequality for metric distances. Then, the barcode X1 (10-1) is assigned as the correction for the decoded barcode Y. This method allows for correction of decoded barcodes comprising an error penalty of up to k errors.

Hamming distances and/or Levenshtein distances (where penalties are integer valued, e.g., "1") allow for a natural interpretation for error correction, with minimum pairwise barcode distances of 2k+1 allowing correction of up to k errors. However, the process of decoding may still result in a decoded barcode Y that is more than a distance k from all of the designed barcodes, e.g., a decoded barcode Y that falls in the empty space between the spheres of correction 11 and which the decoding process may leave as uncorrected. In some instances, pairwise edit distances may be calculated for designed barcodes as a whole. In some instances, pairwise edit distances may be calculated for one or more segments (corresponding to one or more code words) for the designed barcodes. In some instances, a set of designed barcode sequences may be generated to satisfy a specified error correction capability. For example, in some instances, the designed barcodes may be required to have a minimum pairwise edit distance such that they guarantee an error correction capability of correction at least 1, at least 2, at least 3, at least 4, at least 5, at least 6, at least 7, at least 8, at least 9, or at least 10 decoded barcode errors, e.g., substitution, insertion, and/or deletion errors. In some instances, the error correction methods disclosed herein may be applied to correcting barcode errors in decoded barcodes as a whole. In some instances, the error correction methods disclosed herein may be applied to correcting barcode errors at one or more positions (i.e., in one or more code words) that make up the decoded barcodes.

A general algorithm for barcode design and correction for the general edit distances is now presented. First, start with a list of acceptable candidate barcode sequences $\hat{\mathcal{A}}_1 \times \ldots \times \hat{\mathcal{A}}_L$ comprising L letters, where the letter at each position is drawn from the corresponding letter sets $A_1, A_2, \ldots, A_L$. Select a candidate barcode sequence lexicographically from the list and include it in the final set of designed barcodes if it is greater than the distance 2k with respect to all of the other barcodes collected. As part of the selection process, filters can also be added to, for example, include or exclude barcodes from a specified list of predetermined barcodes, exclude barcodes with long consecutive runs of identical letters (e.g., homopolymer sequences of more than 3, 4, 5, 6, 7, 8, 9, or 10 nucleotides in length) or barcodes comprising more or less than a specified GC content (e.g., if the letters comprise A, T, G, C and the decoding process comprises sequencing). For example, in some instances, the barcodes may be selected that exhibit more or less than 10%, 20%, 30%, 40%, 50%, 60%, 70%, or 80% GC content. The selection process is repeated and barcodes are added to the final designed barcode collection until the starting list has been iterated through to the end.

The process deterministically generates a maximal designed barcode set because, by construction, no other barcode sequence from the original list of candidate barcode sequences should be added when the process terminates. The barcodes 10 can then be subsampled to the desired diversity (e.g., a specified total number of unique barcode sequences) at the cost of yielding to the space filling property. The final set of designed barcodes 10 may also be seeded in advance with barcode sequences that are deemed desired and/or necessary. Alternatively or additionally, some barcode sequences may be excluded from the final set of designed barcodes 10 if desired and/or necessary. This process ensures that the new barcode sequences being added to the final set are compatible with the specified pairwise distance criteria. The designed set X of the barcodes 10 may allow for the correction of decoded barcode sequences up to the error penalty k, as previously discussed.

In some instances, a metric tree data structure may be used to store a list of designed barcodes. Metric tree data structures are data structures specifically configured to index data in a metric space (i.e., a data set and a corresponding "metric" or function that defines a distance between any two members of the set). Metric tree data structures utilize properties of metric spaces such as the triangle inequality to make access to the data more efficient, and thus may confer advantages in addressing the computational challenges inherent in generating very large sets of designed barcodes that meet a specified set of design criteria. Examples of metric tree data structures include, but are not limited to, M-tree data structures, vp-tree data structures, cover tree data structures, MVP tree data structures, or BK-tree data structures.

"BKTrees" may be used as data structures to store a resulting list of designed barcodes. BKTrees are metric tree data structures that allow use of efficient algorithms for searching nearest neighbors within a defined distance radius from a new designed barcode 10, and may provide a sufficiently "cheap" insertion of new barcodes 10 that satisfy a specified distance criteria into the tree. More specifically, BKTrees have a construction that scales as $\mathcal{O}$ (D log D), a search performance that scales as $\mathcal{O}$ (log D), and an insertion performance that scales as $\mathcal{O}$ (log D). Thus, the following algorithm (Algorithm 1), which inserts a designed barcode 10 into the BKTree only if a set Z of nearest neighbor candidate barcodes residing within a distance 2k is the empty set, may be used in barcode design:

| Algorithm 1: Barcode Design |
|---|
| Result: Set of barcode sequences $\chi$<br>Initialize a BKTree storing the final design sequences $\chi$. Tree may be empty or contain seed sequences $\chi_0$;<br>foreach barcode X drawn lexicographically from $\mathcal{A}_l \times \ldots \times \mathcal{A}_L$ do<br>\| if X passes all "pre" filters then<br>\| \| Find $\mathcal{Z}$ = neighbors of X within distance 2k in $\chi$;<br>\| \| if $\mathcal{Z}$ is empty then<br>\| \| \| Insert X into the BKTree containing $\chi$;<br>\| \| end<br>\| end<br>end<br>Drop any barcodes in $\chi$ that do not pass some "post" filters. |

Iterating lexicographically may introduce an exponential time complexity ($\mathcal{O}((\max_i|\hat{\mathcal{A}}_i|)^L)$). For example, for each designed barcode 10, there may be an $\mathcal{O}$ (log D) number of comparisons required during the search for neighbors, with each comparison requiring a distance computation of $\mathcal{O}$ ($L^2$) in the general edit distance case, and $\mathcal{O}$ (L) in the Hamming distance case. Thus, complexity may be exponential and become quickly unwieldy for a large L and a small k. To alleviate this, a mathematical property of string metric distances may be used: if two barcodes of equal and even length $X_{ab}$, $X_{cd}$ can be split in the middle to generate four equal length pieces $X_a$, $X_b$, $X_c$, $X_d$, then $$\max(d(X_a,X_c),d(X_b,X_d))\leq d(X_{ab},X_{cd})\leq d(X_a,X_c)+d(X_b,X_d).$$

This means that if $X_a, X_b \in \chi_1$, which is designed with the minimum pairwise distance of $2k_1$, and $X_c, X_d \in \chi_2$, which is designed with the minimum pairwise distance of $2k_2$, then $d(X_{ab}, X_{cd}) \geq \max(2k_1, 2k_2)$. More specifically, if $k_1=k_2=k$, then a smaller set of designed barcodes $\chi_1$ may be used to construct a larger set of designed barcodes as $\chi=\chi_1\times\chi_1$ with the same distance property as the smaller set.

While an exponentially large set of designed barcode sequences X can still be constructed (e.g., from initially iterating through an exponentially large set of designed barcodes 10), the final diversity of the set of designed barcodes may still be exponential with respect to the length L but is still constricted by the desired sphere of correction. Mathematically (in particular for the Hamming distance metric), the maximum designed barcode diversity may be given by $D \sim \mathcal{O}(N^{L-k})$.

When the readout process is "noisy", the decoding process may be designed to correct for a larger k. To ensure sufficient target diversity, the length L of the designed barcode 10 may be increased. This trade-off may be performed on an application by application basis. It should also be noted that the concatenation presented by $\max(d(X_a, X_c), d(X_b, X_d)) \leq d(X_{ab}, X_{cd}) \leq d(X_a, X_c)+d(X_b, X_d)$ is also consistent with the diversity equation in that, if $\chi_1$ has a diversity of $\mathcal{O}(N^{L-k})$, then doubly long barcodes in $\chi=\chi_1\times\chi_1$ have diversity $\mathcal{O}(N^{2L-k})$.

The equation of $D \sim \mathcal{O}(N^{L-k})$ is generally valid when there are no pre-filters used in Algorithm 1. The prefilters are essentially constraints on the kind of designed barcode sequences to allow. If the prefilters are relatively "strong", the diversity scaling for the set of designed barcodes should change. One common prefilter for designed barcodes used in decoding applications regards dilution. Dilution is a constraint that, for each position within the designed barcodes, a portion of the various letters is not identical but rather skewed towards one letter. So, dilution is the case where the proportion of each letter is deviated from N (the alphabet size) on average, and in particular one of the letters has diluted its proportion to $F_{dilution}$ (i.e., a dilution factor), while the remaining letters have proportions of $$\left(\frac{1-F_{dilution}}{N-1}\right).$$

Such a constraint may be implemented in algorithm 1 by eliminating any designed barcodes X drawn from the starter set that do not have the correct proportion of the diluted letter over the L positions. This reduces the number of letters available at each position by increasing the entropy as follows:

$$\begin{aligned}\mathcal{H}(F_{dilution}, N) &= \sum_i -p\log p \\ &= -F_{dilution}\log F_{dilution} - (1-F_{dilution})\log\left(\frac{1-F_{dilution}}{N-1}\right) \\ &= \mathcal{H}_0(F_{dilution}) + (1-F_{dilution})\mathcal{H}_1(N-1)\end{aligned}$$

where $\mathcal{H}_0$ is the binary entropy and $\mathcal{H}_1$ is the entropy of equally proportional states. When $F_{dilution}=1/N$ and all letters are equally likely, the $\mathcal{H}(F_{dilution}, N)$ equation reduces to $\mathcal{H}(F_{dilution}, N)=\mathcal{H}_1(N)$. The number of effective letters available at each position may then be given by:

$\hat{N}=\exp(\mathcal{H}_0(F_{dilution})+(1-F_{dilution})\mathcal{H}_1(N-1))$, and the diversity equation $D \sim \mathcal{O}(N^{L-k})$ may be stated for $\hat{N}$.

Nearest neighbor correction for decoded barcodes comprising errors may be implemented by starting with the designed barcode set $\chi$ which satisfies a condition that the minimum pairwise distances are greater than 2k. For the query (decoded) barcode Y, there should be at most one designed barcode 10 within a distance k if the distance is a metric. Then, that designed barcode 10 is assigned as the correction for decoded barcode Y. If the error is more than k, the correction is incorrect, leading to a false positive. If there is no designed barcode 10 from the designed barcode set $\chi$ within the distance radius k, then the query (decoded) barcode Y remains uncorrected. This may be performed for every decoded barcode sequence in $\mathcal{Y}$ to obtain a set of corrected barcode sequences $\mathcal{Y}'$, exemplarily implemented as follows in Algorithm 2:

| Algorithm 2: Nearest Neighbor Barcode Correction |
|---|
| Result: Set of corrected barcode sequences $\mathcal{Y}'$<br>Initialize empty set of final corrected sequences $\mathcal{Y}'$; |

-continued

Algorithm 2: Nearest Neighbor Barcode Correction

```
Initialize a BKTree storing the available design sequences X;
foreach barcode Y drawn from 𝒴 do
|     Find Y' = neighbor of Y within distance k in X;
|     if neighbor found then
|     |      Insert Y' into 𝒴';
|     else
|     |      Insert Y into 𝒴';
|     end
end
```

With minimum pairwise edit distances of greater than 2k, barcode errors may be corrected with a penalty of ≤k as guaranteed by the triangle inequality. However, a version of the barcode design process presented in Algorithm 1 may still be implemented when the distance may not be a true metric quantity. That would still provide a holistic way to design barcodes, but the resulting set may not have these error correction guarantees. Even if ≤k corrections can be performed (e.g., in the case of integer penalties), up to 2k errors can be detected. Designing barcodes with minimum pairwise Hamming distances of 2 is degenerate in that only a single error can be detected without prior information to correct it.

Decoding Processes and Modules

Decoding processes are methods used to detect and decode a set of barcodes used in, for example, in situ detection, spatial array applications, bead array applications, etc. Decoding modules are generally instruments and platforms configured to readout barcode sequences (e.g., nucleic acid barcode sequences) using optical microscopy-based imaging, electronic ion sensing, and/or other modalities of sensing. By virtue of knowing where a signal is being generated, a spatial location may be associated for each decoded feature and may have applications in many spatial genomics platforms. The following example assumes that imaging-based optical decoding has been enabled in a flat "flow cell" format that supports the molecules of interest to be decoded. Generally, all nucleic acid sequencers are special cases of decoding modules by this definition. However, nucleic acid sequencers are designed to work with arbitrary nucleic acid sequences where there is no control over string metric distance between nucleic acid sequence strings.

As discussed above, abstractly defined barcode sequences may take values in a starter set $\hat{\mathcal{A}}_1 \times \ldots \times \hat{\mathcal{A}}_L$, where $\hat{\mathcal{A}}_i \subseteq \hat{\mathcal{A}}$ and $\hat{\mathcal{A}}$ is a set of N generic alphabet letters. For example, consider an abstract barcode sequence DCNK∈{D, C}×{C, N, D}×{N}×{K, D, C, N}, with the alphabet $\hat{\mathcal{A}}$={D, C, N, K}. How does "DCNK" correspond to the actual DNA sequence over $\mathcal{A}$={A, T, G, C}? And, how does "DCNK" get decoded?

First, as noted above, the term "barcode" may refer to a chemical barcode or to its representation in a computer-readable, digital format. Chemical barcodes generally refer to the physical molecules (e.g., DNA molecules) that form the unique label associated with a target molecule (e.g., as in in situ applications) or a location (as with bead arrays). A set of "designed barcodes" is a set of chemical barcodes (or their digital equivalent) that meets a specified set of design criteria (e.g., a specified minimum pairwise edit distance) as required for a specific application. Decoded barcodes generally refer to a set of digital barcode sequences produced via a decoding process that ideally match that the set of designed barcodes, but that may include one or more erroneous decoded barcode sequences arising from, e.g., a noisy decoding process. Both chemical (designed) and decoded barcodes can be represented in the language of generalized barcodes as described herein. The decoding process generally involves deciphering the decoded barcode at the locations of one or more physical features by monitoring the interactions between a set of fluorophore-labeled barcode probes and the designed barcodes present at the locations of the one or more physical features.

In the case of, for example, nucleic acid barcode sequences (e.g., DNA barcode sequences) the DNA sequences comprising the designed chemical barcodes may be organized as combinatorial structures each consisting of L parts (or segments), such that the DNA sequence of the $i^{th}$ part of the structure can be uniquely labeled with a letter from $\hat{\mathcal{A}}_i$ to provide the decoded barcode corresponding to it. By construction, the combinatorial structure in the chemical barcode is represented in the cross product {D, C}×{C, N, D}×{N}×{K, D, C, N}. A special "OFF" letter included for some "sparse" decoding applications (explained in greater detail below) may change the interpretation of the combinatorial barcode structure, but the abstract description still applies.

Thus, to decode such a combinatorial structure, the number of decoding cycles may be established as the length of the barcode (e.g., four in the case of DCNK). Then, for each decoding cycle 1≤i≤L, the letters $\hat{\mathcal{A}}_i$ can be detected across M channels of sensing (e.g., different color channels in a fluorescence imaging system). Now, assume that in this example there are three color channels available for imaging. The cycle i may involve biochemistry steps where a pool of fluorescently-labeled barcode probes are introduced that are complementary to the $|\hat{\mathcal{A}}_i|$ different DNA sequences that the $i^{th}$ segment can have across all of the designed barcodes being used. These barcode probes target the $i^{th}$ segment of each barcode via hybridization, ligation, or other targeting chemistry. The number of fluorophores available is M (i.e., one for each channel of detection). Accordingly, for decoding cycle number 4, a decoding module should be configured to detect four states labeled as $\hat{\mathcal{A}}_4${K, D, C, N} across three channels of imaging.

In order to enable encoding of, e.g., the four states labeled as $\hat{\mathcal{A}}_4$={K, D, C, N} across three channels of imaging, the $|\hat{\mathcal{A}}_i|$ complementary barcode probes used in each decoding cycle are conjugated with a unique stoichiometric combination of M fluorophores such that $|\hat{\mathcal{A}}_i|$ states can be detected. This stoichiometric conjugation chemistry may be referred to as an "M-color-$|\hat{\mathcal{A}}_i|$-state chemistry. For example, in a three-color, four-state chemistry (3C4S) that is operable to detect four states for the four letters K, D, C, N, the stoichiometric ratios of K: [1, 0, 0], D: [0, 1, 0], C: [0, 0, 1], N: [0, 1, 1] may exist. If the three-dimensional signal intensity vector (e.g., the three-dimensional fluorescence signal intensity vector) for each barcoded spatial feature is plotted, this scheme would result in four clusters aligned with the four directions encoded by the four stoichiometric numbers. Other valid sets of ratios could be used as well, such as K: [1, 1, 0], D: [0, 1, 1], C: [1, 0, 1], N: [0, 0, 0], assuming they are practically implementable. Similarly, the ratios of K [1, 0, 0], D: [0, 1, 0], C: [0, 0, 1], N: [0, 2, 2] may work as long as twice the concentration of the $2^{nd}$ and $3^{rd}$ dyes can be conjugated to the barcode probes for the $4^{th}$ state and the resulting differences in signal intensities are detectable. These barcode letters are generally associated one-to-one with the states encoded for in the barcode chemistry.

Figure 2:
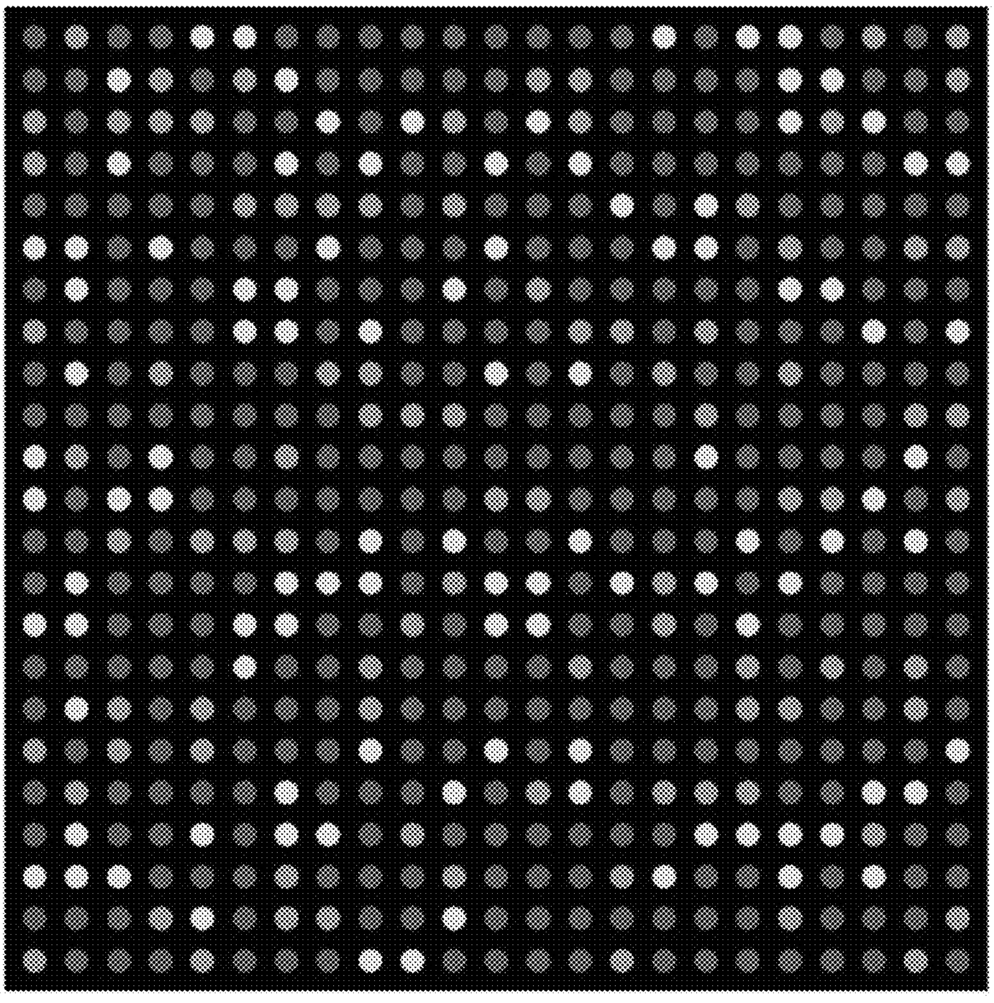
FIG. 2 is an exemplary image of a flowcell of barcoded molecules generated during a decoding cycle.

At the end of cycle i, a decoded letter (or code word) is assigned to the $i^{th}$ segment of the barcode at each spatial feature. The $i^{th}$ part of each barcode molecule is thus successfully decoded. FIG. 2 illustrates one non-limiting example of three channel imaging of decoding cycle number 4 where the letters K, D, C, N are all detected along stoichiometry vectors K: [1, 0, 0], D: [0, 1, 0], C: [0, 0, 1], N: [0, 1, 1] in a three-color/four-state chemistry (3C4S) chemistry. The color channels are red, green, blue, with N being detected in equal proportion in both green and blue channels and being false colored in yellow.

In some instances, the decoding chemistry (e.g., the barcode probes) for any of the decoding cycles may be designed such that not all barcode molecules associated with the targeted molecules (e.g., gene transcripts) are visible in the image. Decoding schemes designed to ensure that a subset of the barcoded targets are invisible in a cycle i can generally be configured in two ways. The first approach involves using barcode probe(s) to detect the $i^{th}$ part of the barcode(s) meant to be invisible in that decoding cycle that have no fluorophore attached. The second approach involves using a pool of barcode probes to detect the $i^{th}$ part of the barcodes that does not include barcode probe(s) for detecting the $i^{th}$ part of the barcode(s) meant to be invisible in that decoding cycle.

Although some fraction of the chemical (designed) barcodes may be invisible in a particular decoding cycle, the signal intensity (or lack thereof) detected for those barcodes can still be extracted from their known locations in images for other decoding cycles where they are visible (after registration). There generally has to be at least one such decoding cycle in which any given chemical barcode is visible, otherwise they are invisible in each cycle and thus not decodable. The signal distribution for such "invisible" barcodes in a given decoding cycle is close to a background signal, as illustrated for the "G" in FIG. 3.

In some instances, a letter $\eta$ may be introduced to the barcode alphabet to capture the fact that the feature with $\eta$ in the barcode sequence is detected in the "OFF" state. Designed barcodes (and the barcode probes used for decoding them) can then be designed with an augmented alphabet of $\mathcal{A}'=\mathcal{A}\cup\{\eta\}$ consisting of "ON" letters (e.g., visible letters) and the OFF letter. Generally, $\mathcal{A}'_i=\mathcal{A}_i\cup\{\eta\}$ are used in the decoding cycle i for all $1\leq i\leq L$. Of course, degenerate sequences consisting of only $\eta$'s may be excluded and filters may still be applied.

An example of a typical filter used in combination with a barcode alphabet comprising an OFF letter is the dilution filter described above. The OFF state may be diluted, for example, to account for a large fraction of the target analytes in applications such as in situ transcriptomics. This may help to alleviate or avoid optical crowding issues where it becomes difficult to identify individual features either visually or algorithmically because their density in space exceeds the resolution limits of the imaging system. If detection of the OFF state is configured via the second approach described above, the $i^{th}$ part of those barcode sequences is simply dropped from the chemical (designed) barcode as it is not probed. Thus, an expanded decoded barcode exists whose corresponding chemical (designed) barcode matches a sequence of ON letters within the expanded decoded barcode. For example, $A\eta BT\eta\in\{A, B, \eta\}\times\{B, D, \eta\}\times\{A, B, \eta\}\times\{A, T, \eta\}\times\{B, T, \eta\}$ is the expanded decoded barcode for the designed barcode structure ABT. With the first approach for detection of the OFF state described above, the chemical (designed) barcode and the decoded barcode sequences have the same structure.

Even though the designed chemical barcode may be more compact, the inferred barcode sequence from the point of view of decoding is the decoded barcode sequence, as errors in the decoding process consist of misidentification of the letters in the augmented cycle-specific alphabets $\mathcal{A}'_i$ used in detecting and constructing the decoded barcodes.

In some instances, e.g., for noisy decoding processes, the decoding chemistry may introduce errors (e.g., one letter or state of a designed barcode may be confused with another) in the decoded barcodes, thus giving rise to the need for error correction. Thus, for accurate decoding, barcodes should be designed to comply with, e.g., a specified minimum pairwise edit distance (e.g., a specified minimum pairwise Hamming distance). Commercial nucleic acid sequencers (special cases of decoding modules) have a relatively high accuracy of sequencing as their errors are predominantly substitution errors which occur at less than a rate of 0.1%. The sources of noise in nucleic acid sequencers can include, for example, thermal noise, sensor noise in the optics, the kinetics of various binding reactions, the DNA sequence specificity of probe molecules and their binding to complementary targets, etc.

As described herein, barcode design is intimately tied with and simultaneously lends itself to decoding cycle design and error correction, which in turn is tied to available hardware and practical considerations. Typically, chemical barcodes and their associated decoding cycle schemes may be designed based on, e.g., the available hardware and chemistry (e.g., comprising M detection channels), the target diversity D, and desired barcode correction guarantees (e.g., targets for acceptable false positive rate "FPR" and true positive rate "TPR") under a reasonably quantified substitution error rate that is spatially uncorrelated from cycle to cycle in the decoding process.

With barcodes designed in, for example, the Hamming distance space, the order in which the decoding cycles are performed may not particularly matter as the order would permute all of the barcodes in generally the same way without affecting their Hamming distances from each other. In some instances, a single decoding chemistry cycle may be performed first where all of the locations comprising barcoded target molecules of interest are fluorescently lit up. This may simplify computation for the subsequent decoding cycles as the locations of spatial features of interest may already be known.

Figure 3:
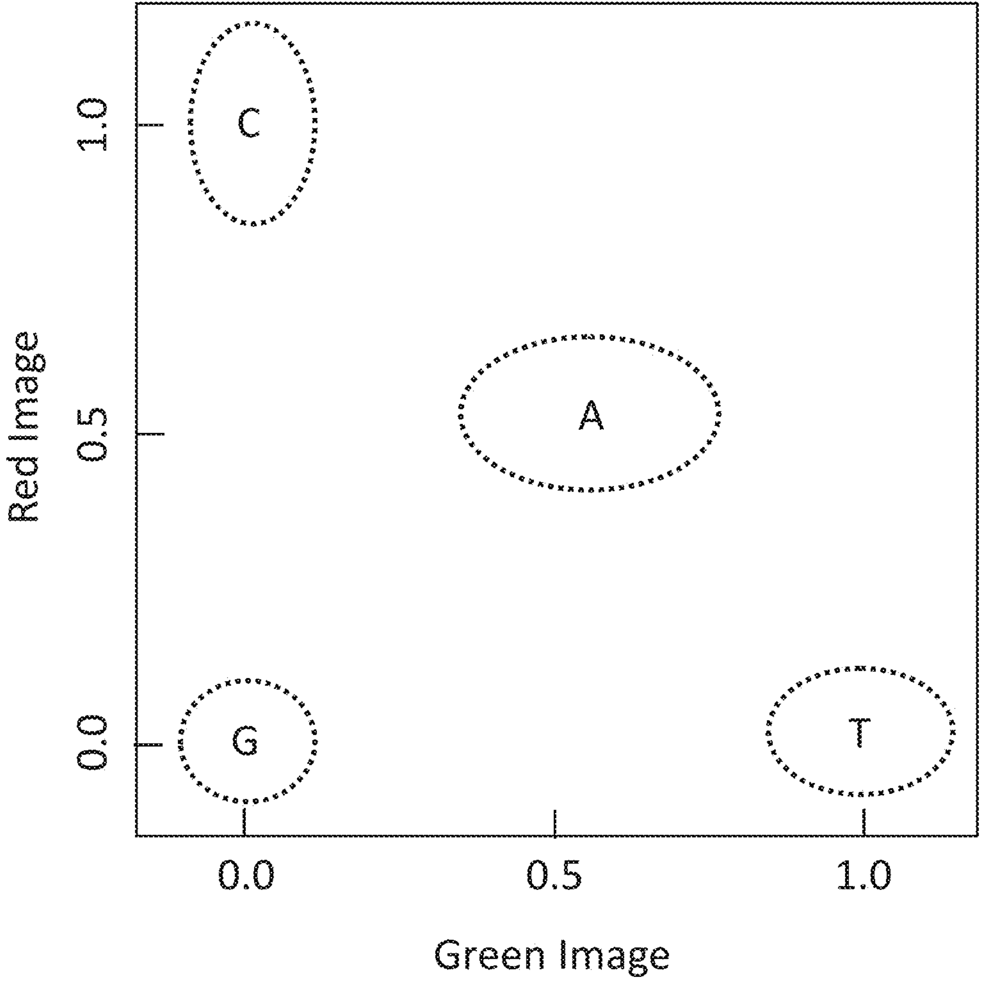
FIG. 3 is an exemplary fluorescence signal intensity distribution of a decoding cycle.

To illustrate, in one example, a two color chemistry commonly used in some modern nucleic acid sequencers has a two-color/four-state chemistry (2C4S). As illustrated in FIG. 3, the stoichiometric ratios used are T: [0, 1], C: [1, 0], A: [1, 1], G: [0, 0] to show a two-dimensional fluorescence signal intensity vector distribution for a single decoding cycle image. In this example, a base is associated with each cluster of fluorescence signal intensities and each cluster is defined by its stoichiometry vector. By using a single unified framework for barcode design and decoding cycle design, different schemes of decoding may be contrasted and harmonized. The single unified framework also lends itself to a unified software architecture that is operable to simulate the decoding systems as well as generate barcode designs and implement barcode error correction.

Dense Decoding

As used herein, the term "dense decoding" generally refers to a special case where all decoding cycles satisfy the property $\hat{\mathcal{A}}_i = \hat{\mathcal{A}}$ for all i (i.e., where all letters are detected in each decoding cycle, and where the relative proportion of all letters is identical, $$F_{dilution} = \frac{1}{N}).$$

Based on this definition, the OFF state may be used as one of the letters in a dense decoding process, but its frequency will be identical to other letters in any of the decoding cycles. These assumptions imply that, for a fixed target diversity, dense decoding can be implemented using the shortest barcodes and the fewest number of decoding cycles. However, this may have implications with respect to the unit cost (e.g., for decoding reagents such as the barcode probes used) and run time of the decoding process. A common form of dense decoding occurs when $\hat{\mathcal{A}} = \mathcal{A} = \{A, T, G, C\}$ such as used in commercial DNA sequencers. In this example, each letter corresponds directly to a DNA base and the decoded barcode's sequence is identical to the underlying DNA sequence of the chemical barcode. Each cycle of decoding is configured to detect all four bases. Nucleic acid sequencers that employ this method include sequencers that utilize sequencing by synthesis, sequencing by ligation, and sequencing by hybridization chemistries. In Sequencing by Oligonucleotide Ligation and Detection (SOLiD) and Sequencing with Error reduction by Dynamic Annealing and Ligation (SEDAL) di-nucleotide sequencing, each DNA sequence probe is uniquely associated with a color code. The color code of the decoding barcodes fits the generalized barcode definition described herein. More general versions of decoding may be encapsulated by the general barcode definition where the DNA barcode probe sequences are uniquely associated with segments of a general chemical barcode sequence over a general alphabet, and the decoding process determines this general chemical barcode sequence.

Figure 4:
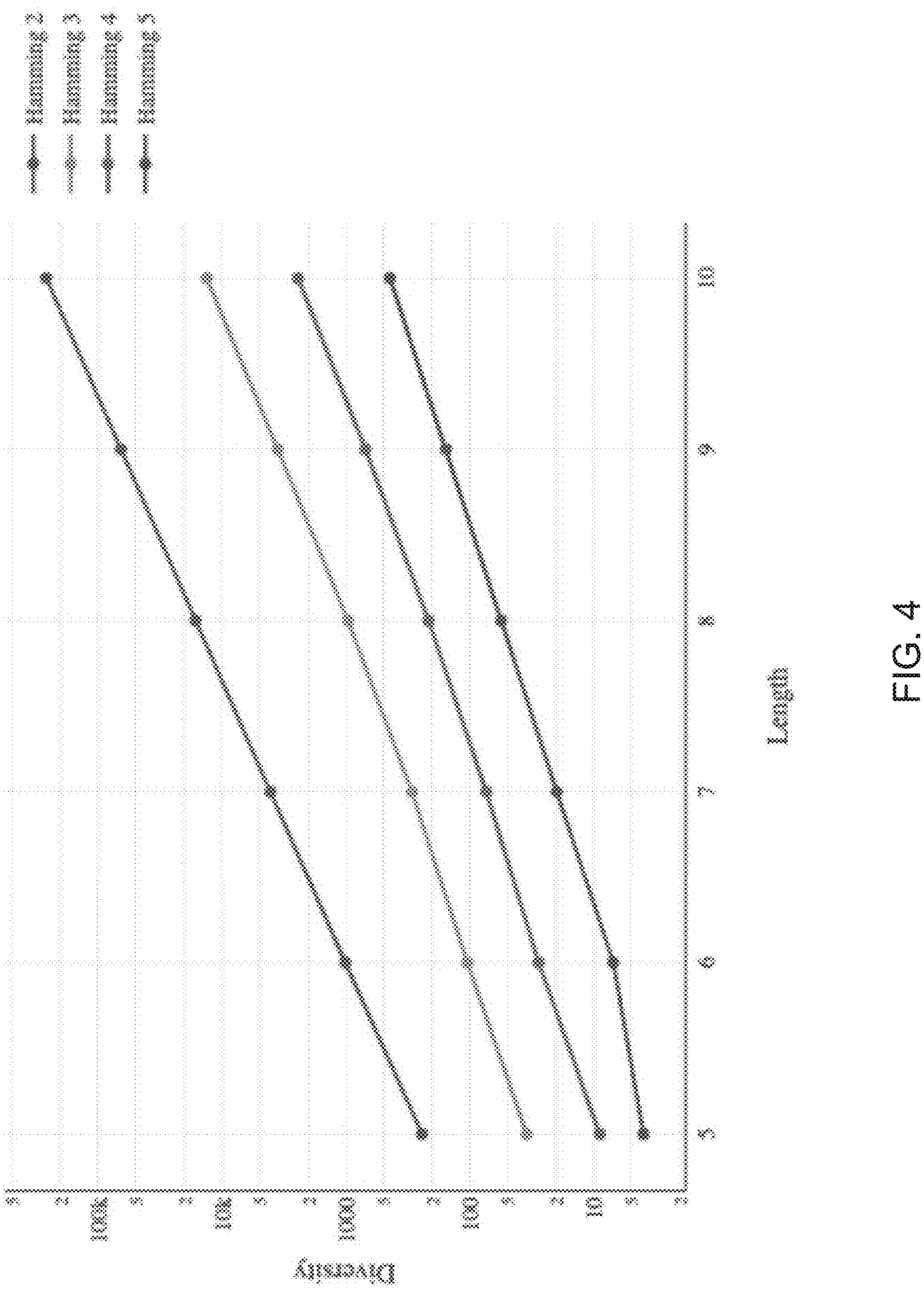
FIG. 4 is a graph illustrating exemplary barcode pools with various minimum pairwise Hamming distances.

FIG. 4 illustrates a maximum diversity D that may be encoded for by barcodes of length L (e.g., ranging from 5 to 10 nucleotides in the case of nucleic acid barcode sequences) and a specified minimum pairwise Hamming distance $H_D$ (e.g., integer values ranging from 2 to 5) which follows the exponential scaling law $D \sim \mathcal{O}(N^{L/k})$ discussed above. The simulated results were obtained using Algorithm 1 for a traditional case of dense decoding using $\mathcal{A} = \{A, T, G, C\}$. In this example, no filters or seed sequences (e.g., predefined sequences of nucleotides used to bind to target gene sequences or gene transcripts) were used, and the starter barcode set was established as $\mathcal{A} \times \ldots \mathcal{A}$, with each decoding cycle capable of detecting all of $\mathcal{A}$ as mandated by the definition of dense decoding. The simulated data is plotted for barcode pools having minimum pairwise Hamming distances $H_D$ of 2 (top trace), 3 (second trace from top), 4 (third trace from top), and 5 (fourth trace from top).

Now, consider barcodes of length 8 and a pairwise Hamming distance $H_D \geq 3$. This barcode set is equal to or less than $|\chi| = 963$ in size. In this simulation, for each barcode in the set, every letter is randomly substituted by a different letter at some probability that captures the per letter substitution error rate when using, e.g., sequencing, for barcode readout. Then, the nearest neighbor error correction algorithm (Algorithm 2) may be used to perform barcode correction, as illustrated in FIGS. 5-7.

Figure 5:
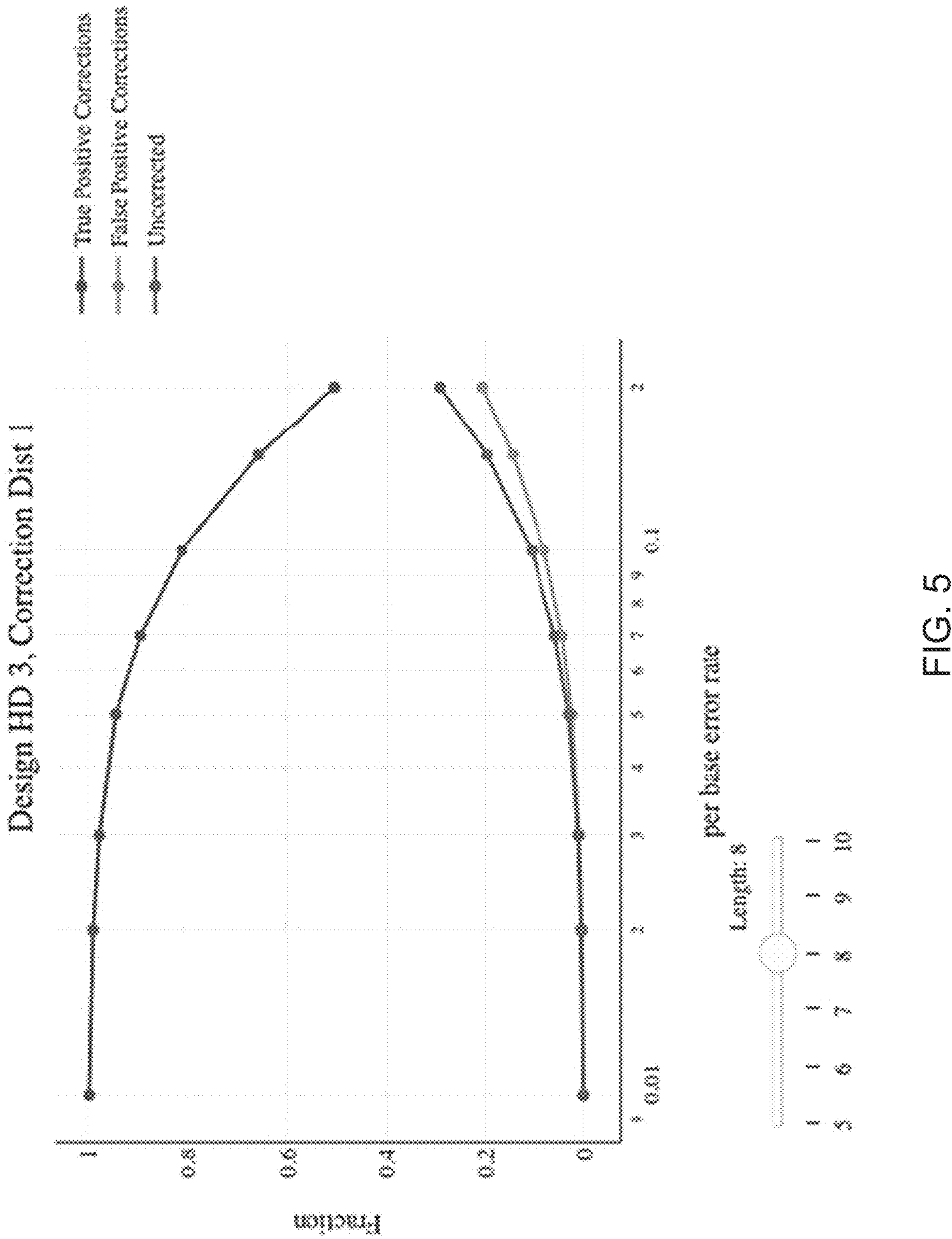
FIG. 5 is a graph illustrating exemplary true positive and false positive error correction rates for correcting single base errors in a set of designed nucleic acid barcodes of length 8 and a minimum pairwise Hamming distances equal to three.
Figure 6:
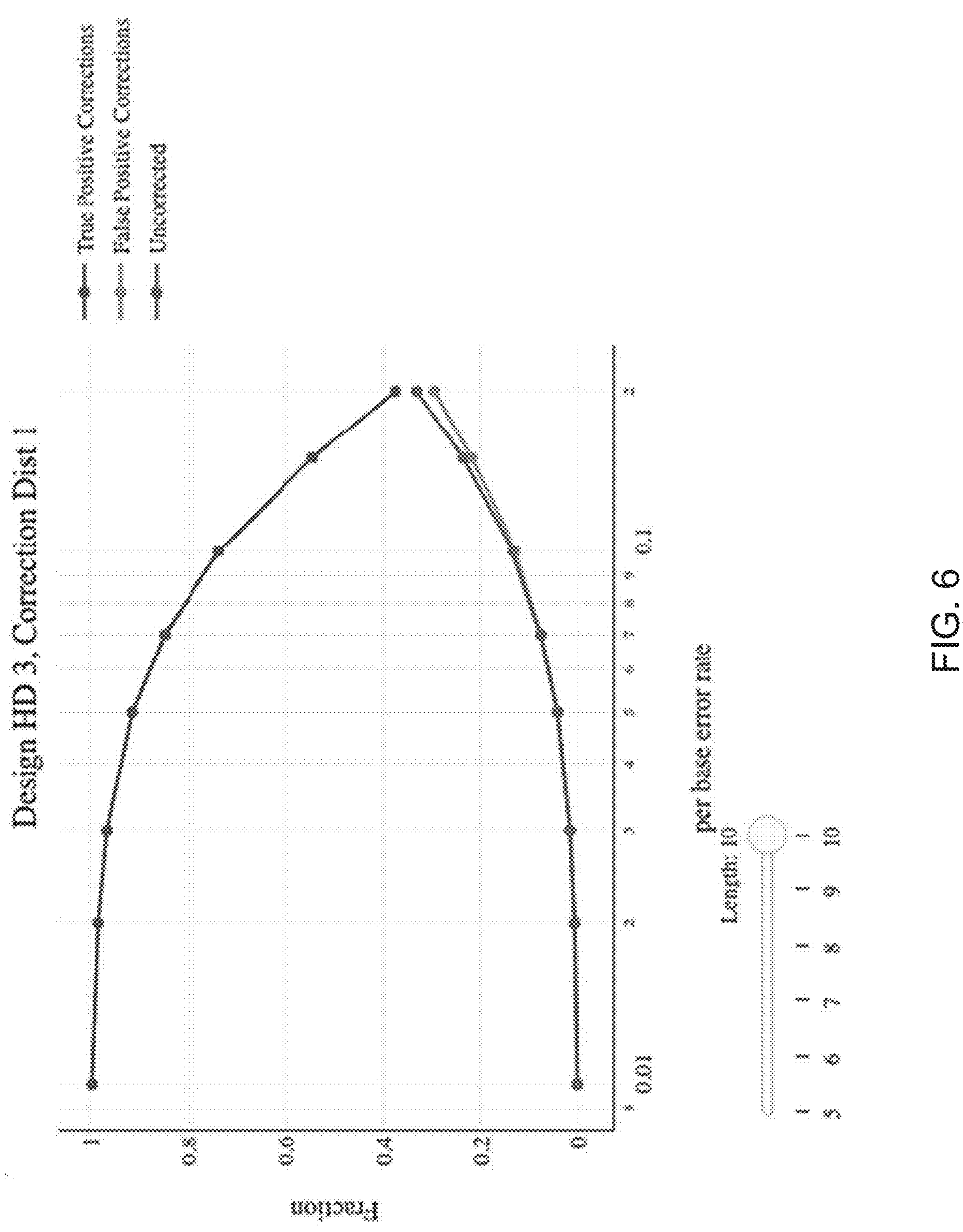
FIG. 6 is a graph illustrating exemplary true positive and false positive error correction rates for correcting single base errors in a set of designed nucleic acid barcodes of length 10 and a minimum pairwise Hamming distances equal to three.

FIG. 5 is a graph illustrating the uncorrected error rate, and true positive and false positive error correction rates for correcting single base errors in sets of designed nucleic acid barcodes of length 8 and a pairwise Hamming distance equal to three. FIG. 6 is a graph illustrating the uncorrected error rate, and exemplary true positive and false positive error correction rates for correcting single base errors in a set of designed nucleic acid barcodes of length 10 and a pairwise Hamming distances equal to three. FIG. 7 is a graph illustrating the uncorrected error rate, and exemplary true positive and false positive error correction rates for correcting two base errors in a set of designed nucleic acid barcodes of length 8 and a pairwise Hamming distances equal to five. In each of FIGS. 5-7, the x-axis is a simulated substitution error rate and the y-axis is a fraction of the simulated set $\mathcal{Y}$. The true positive error correction rate (TPR; upper curve), the false positive error correction rate (FPR; lower curve), and the uncorrected error rate (middle curve) are illustrated with the three curves. As can be seen in these figures, the correction performance decreases as the error rate increases (e.g., TPR drops while FPR and the uncorrected error rate both climb). If the barcode length is increased from 8 to 10, then the performance degrades uniformly for all error rates. This is intuitive because, assuming that the error rate is e, and the number of errors accumulated over L cycles is distributed as Binom(n=L, p=e), the correction algorithm is only capable of correcting up to k errors. So, the theoretical upper bound of the TPR is given by the cumulative distribution function (CDF) of $TPR = Binom\mathbb{P}(n=L, p=e; x \leq k)$. To the leading order, when $e \ll 1$, $TPR = (1-e)^{L-1}(1+(L-1)e) \sim 1 - e^2(L-1)^2$.

Figure 7:
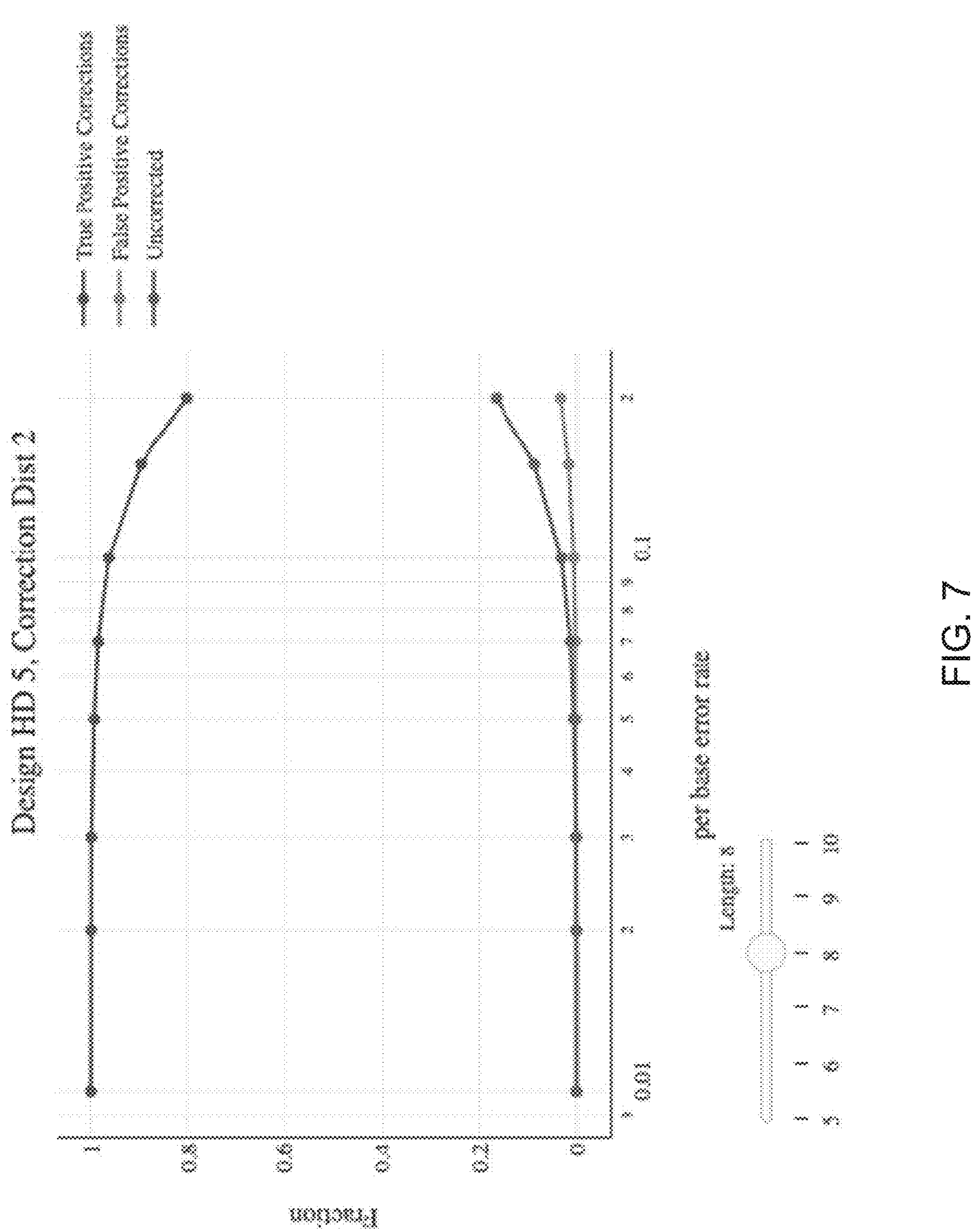
FIG. 7 is a graph illustrating exemplary true positive and false positive error correction rates for correcting two base errors in a set of designed nucleic acid barcodes of length 8 and a minimum pairwise Hamming distances equal to five.

To tolerate a high error rate, k can be increased, as illustrated in FIG. 7. FIG. 7 illustrates a better correction performance than that illustrated in FIG. 5 and FIG. 6. Note that the TPR does not depend on the alphabet size $|\hat{\mathcal{A}}|$, as expected from Binomial distribution theory.

For a fixed barcode alphabet and design objectives for both barcode diversity and TPR, barcodes can be designed for maximum decoding throughput while also enabling highly accurate decoding capabilities. The length L and the separation distance k of the barcodes in edit distance space (e.g., Hamming distance space) may be tuned to correct for the error rate e in a given application. The effects of tuning these parameters are opposite in two quantities, e.g., $L\downarrow, e\downarrow, k\uparrow \Rightarrow TPR\uparrow$ and $L\uparrow, k\downarrow \Rightarrow D\uparrow$. This tuning may be performed carefully to ensure that the barcode length L is as short as possible (e.g., for faster and less complex decoding) while still providing acceptable barcode diversity and error correction guarantees. The complexity of the decoding process is generally hidden behind the single modeling parameter e. Even though the simulation results described here are for a specific case of $\mathcal{A} = \{A, T, G, C\}$, the intuition regarding barcode diversity, TPR, and their trade-offs is extendable to other scenarios.

Sparse Decoding

As used herein, the term "sparse decoding" refers to a decoding process where the designed barcode construction is not that having the shortest possible decoding process. For example, a sparse decoding scenario may correspond to the case where one of the letters of $\hat{\mathcal{A}}_i$ is a proper subset (i.e., not the full set) of the full alphabet A. Alternatively or additionally, a sparse decoding scenario may correspond to the case where OFF letters are used to introduce extra dilution. Sparse decoding allows for the design and decoding of barcodes with more letters than what would be practically detected in any single decoding cycle. In the following examples, sparse decoding may generally refer to the case where OFF letters are used to introduce extra dilution.

Whether or not the OFF letter $\eta$ is used in the decoding process, Algorithm 1 is still applicable to barcode sequences designed with desired edit distance properties (e.g., Hamming distance properties) and error correction guarantees, as described above, once the target letters of each cycle $\hat{\mathcal{A}}_i$ and thus the starter (or candidate) barcodes $\hat{\mathcal{A}}_1 \times \ldots \times \hat{\mathcal{A}}_L$ are determined.

As a non-limiting example of a sparse decoding process, a MERFISH (multiplexed error-robust fluorescence in situ hybridization) scheme comprising 16 cycles of decoding was performed (see, e.g., Chen, et al. (2015) "Spatially Resolved, Highly Multiplexed RNA Profiling in Single Cells", Science 348(6233):aaa6090; see also, e.g., U.S. Pat. No. 11,098,303; U.S. Pat. Pub. 20190264270; and PCT/US2019/065857 (WO2020123742A1) for an exemplary description of the MERFISH probes, encoding schemes, and methodologies), where each decoding cycle comprised use of a one-color two-state-chemistry (1C2S) for detecting a binary alphabet including the OFF letter $\hat{\mathcal{A}}_i=\{\omega, \eta\}$. The decoded barcodes can then be interpreted as binary strings where $\omega$ is the letter corresponding to a spatial feature visible in the single color channel. Each designed barcode sequence may be designed to have $4\omega$ and $12\eta$ (i.e., 16 barcode segments) with a pairwise Hamming distance $H_D \geq 4$. This set of designed barcodes can be used to encode up to D=1000 gene transcripts. To summarize, in this merFISH scheme, designed barcodes may be drawn from starter sequences in $\{\omega, \eta\} \times \ldots \times \{\omega, \eta\}$. The designed barcode sequences X satisfy two conditions: they comprise $4\omega$s; and exhibit a minimum pairwise Hamming distance $H_D \geq 4$. Algorithm 1, as described above, can be used to construct the designed barcode sequences that satisfy the minimum pairwise Hamming distance $H_D \geq 4$ criterion while enforcing the 4 $\omega$s criterion using a prefilter during the iteration of sequence selection or with a post-construction filter.

Other decoding schemes are operable within the disclosed general barcode design and decoding methods while avoiding optical crowding via the use of the OFF letter (e.g., those used in sequential fluorescence in situ hybridization (seqFISH, see, e.g., Lubeck, et al. (2014) "Single-cell in situ RNA profiling by sequential hybridization", Nat Methods. 11(4):360-1. doi: 10.1038/nmeth.2892; and U.S. Pat. No. 10,457,980 for an exemplary description of the seqFISH probes and methodology), seqFISH+ (comprising an expanded barcode color pallete, see, e.g., Eng, et al. (2019) "Transcriptome-scale super-resolved imaging in tissues by RNA seqFISH+", Nature. 568(7751):235-239. doi: 10.1038/s41586-019-1049-y; and U.S. Pat. Pub. 20210017587 for an exemplary description of the seqFISH+ probes and methodology), in situ sequencing (see, e.g., Ke, et al. (2013) "In situ sequencing for RNA analysis in preserved tissue and cells", Nat Methods. 10(9):857-60. doi: 10.1038/nmeth.2563; U.S. Pat. No. 11,021,737; U.S. Pat. Pub. 20200224244; U.S. Pat. Pub. 20210164039; and PCT/EP2020/065090 (WO2020240025A1)), and fluorescence in situ sequencing (FISSEQ) applications (see, e.g., Lee, et al. (2014) "Highly multiplexed subcellular RNA sequencing in situ", Science. 343(6177):1360-3. doi: 10.1126/science.1250212; and U.S. Pat. No. 11,085,072 for an exemplary description of FISSEQ probes and methodologies), etc.).

Assignment of Barcodes to Target Analytes

For in situ applications, dilution of visible barcoded target analytes (e.g., gene sequences or gene transcripts) in any given decoding cycle is an important factor in controlling performance and avoiding optical crowding. For example, some genes may be highly expressed in a particular sample, and detection of barcoded gene transcripts (e.g., barcoded mRNA molecules corresponding to the highly expressed genes) may give rise to optical crowding in one or more decoding cycles, especially if they are co-detected with other highly expressed gene transcripts in the same decoding cycles. Consequently, the encoding of gene transcripts (e.g., the assignment or association of designed barcode sequences to targeted gene transcripts) should be done in a way to reduce optical crowding in any particular decoding cycle and imaging channel.

For example, in one optimization problem, assume the bulk expression levels $E_g$ of each target gene in a model cell of a sample of interest (e.g., an intact tissue sample or section) are known (e.g., via the scientific literature). Then, let the designed list of barcodes be denoted by $B_k$, and let $B_{\pi(g)}$ be the associated barcode for a transcript corresponding to target gene g.

The assignment of barcodes to targets (or the assignment of a series of code words to, e.g., gene transcripts, that may be subsequently decoded into a decoded barcode) may be optimized by defining an objective function and constraints. In this regard, let the optical crowding in decoding cycle i and detection channel l (e.g., the "ON" state) be defined as the total number or concentration of barcoded target molecules visible in the detection channel l at the decoding cycle i in the model cell, which may be denoted by C(i, l). An estimate of the optical crowding can then be defined as $\mathcal{C}(i, l)=\Sigma_g E_g 1\{B_{\Pi(g)}(i)=l\}$. Here, the number of detection channels and ON states is the same. Generally, any other configuration (comprising different numbers of detection channels and ON states) will involve detection of some genes in multiple channels, which is not ideal. Thus, it is generally desirable to reduce any variation in C(i, l) so that each decoding cycle in a given detection channel is similarly crowded.

The first term of the objective function can be defined as $-\mathcal{H}(\mathcal{C}(i, l))$, a negative entropy of the normalized optical crowding. By minimizing this, each decoding cycle in a given detection channel will generally have equal optical crowding. The second term of the objective function may be derived by defining an "isolation score" for each barcode $S_k$. $S_k$ may be calculated as the average edit distance (e.g., the average Hamming distance) for each designed barcode sequence with respect to all of the other designed barcode sequences in the set of designed barcode sequences. Alternative definitions may include, e.g., optical crowding of the local neighborhood (i.e., the number of designed barcode sequences within a neighborhood of a fixed edit distance radius surrounding each designed barcode sequence).

In order to reduce bias in detecting genes having different expression levels, it is generally important to ensure that the designed barcodes assigned to lower expressed genes are isolated as much as possible (i.e., are separated by the largest pairwise edit distances possible). Thus, the second term in the objective function to be minimized may be defined as $\Sigma_g E_g S_{\Pi_g}$. With this in mind, $$\text{objective: } \min_{\Pi}\left(-\mathcal{H}(C(i, l)) + \lambda\sum_{g} E_g S n_g\right),$$

$$\text{subject-to: } C(i, l) \leq T,$$

where λ is the relative weight factor (i.e., an empirically-determined optimization "hyperparameter") between the two terms. The constraint of subject-to: $\mathcal{C}$(i, l)≤T where T is an empirically-determined threshold is to ensure none of the optical crowding factors exceed a fixed limit. T may be determined, for example, using spot detection algorithms run on simulated images. A trade-off occurs as the minimization of the first term may tend to ensure that isolated barcodes (i.e., designed barcodes that are distant in edit distance space) are associated with higher expressed genes so that they are not co-detected in most decoding cycles, while minimization of the second term may tend to ensure that isolated barcodes are associated with lower expressed gene targets. In some instances, the objective function may be minimized using, e.g., a Nelder-Mead method (see, e.g., Nelder, et al. (1965). "A Simplex Method for Function Minimization", Computer Journal 7(4):308-313).

Thus, in some instances, a barcode encoding scheme (or a barcoding module configured to design barcodes and/or implement a barcoding encoding scheme) may rank the target gene transcripts in ascending order of gene expression levels. Then, for each designed barcode sequence, the average pairwise Hamming distance $H_D$ with respect to all other barcodes is calculated, and the designed barcodes are ranked in ascending order based on this average $H_D$. Finally, every target gene transcript may be associated with a designed barcode with the same rank in their sorted lists. This approach ensures that transcripts corresponding to highly expressed genes are generally not co-detected in any given decoding cycle. An algorithm for encoding gene transcripts with designed barcodes based on prior gene expression information and the average $H_D$ is now exemplarily presented in Algorithm 3.

Algorithm 3: Encoding of genes with barcodes based on prior expression information and average $H_D$.

```
Result: Set of eneodings: {(gene, X)|X ∈ χ}
Sort barcodes in χ based on average H_D;
Sort genes based on expression level;
Pair up sorted genes with sorted barcodes.
```

In some instances, expression levels of genes broadly dictate that they need to be associated with designed barcodes (e.g., codewords) as distant from each other as possible in edit distance space. In this regard, it may be advantageous to avoid assigning designed barcodes that are close to each other in edit distance space to different highly expressed gene transcripts that occur in the same spatial neighborhood. For example, two genes may be highly expressed in the same spatial area of, e.g., a tissue sample, if the cell(s) at that location are of the type that highly expresses those genes. So, in some instances, the barcoding algorithms described herein may ultimately be driven by consideration of cell-type as well as gene expression levels. Thus, it may be advantageous to rank gene transcripts based on their expression levels according to cell type, which are generally known a priori for a given sample.

In some instances, an isolation score may be calculated for each designed barcode and used to rank the barcodes. For example, an isolation score may be computed based on, e.g., an average pairwise edit distance (e.g., an average pairwise Hamming distance) from other designed barcodes of a set of designed barcodes, a radius of error correction with respect to other barcodes, as illustrated in FIG. 1, etc. Then, the designed barcodes may be ranked according to their calculated isolation score. Of course, these examples are not intended to be limited to ranking designed barcodes according to just Hamming distances or radiuses of error correction, as other metrics may also be used to rank the barcodes.

If any two gene transcripts corresponding to highly expressed genes are desired to be as distant from each other as possible in terms of their associated barcodes, a different algorithm for designed barcode assignment may be used. For example, a graph theoretic approach may be employed that constructs a fully connected graph of the designed barcodes where the pairwise edit distances (e.g., Hamming distances $H_D$) between any two designed barcodes (or other distance metrics) are the weights on edges between the nodes corresponding to any two designed barcodes. Then, a fully connected graph of the gene transcripts to be barcoded may be constructed where the edges have weights corresponding to, for example, a mean value of the expression levels of the corresponding genes. Then, target gene transcripts may be assigned designed barcodes such that they maximize the total weight of the graph (defined as the sum of the product of the edit distances (e.g., Hamming distance $H_D$) weights and the mean gene expression level weights. This is essentially an embedding of a graph in the discrete edit distance space (e.g., Hamming distance space) onto a one-dimensional gene expression space such that assigned barcode distances are preserved. This may be solved heuristically using the "greedy" Algorithm 4, as follows:

Algorithm 4: Graph based greedy encoding of genes with barcodes based on prior expression information and Hamming distances

```
Result: Set of encodings: {(gene, X)|X ∈ χ}
Generate a list of tuples (X1, X2, w) for any two barcodes X1, X2 with
  a weight w equal to the Hamming distance between them. By
  convention, X1 has lower average H_D of the two;
Generate a list or tuples (g1, g2, e) for any two genes g1, g2 with a
  weight e equal to the mean expression level. By convention, g1 has
  lower expression level of the two;
foreach edge (X1, X2, w) drawn from a reverse-sorted list by weights do
|   if (X1, X2, w) has no barcode assigned so far then
|   | Find the maximum expression level gene pair (g1, g2, e) with no
|   |    previously assigned barcodes;
|   | Assign the higher expression gene g2 to the barcode X2 with
|   |    larger average H_D, and assign gene (g1) to barcode (X1).
|   else
|   | if (X1, X2, w) has exactly one barcode (say) X1 already assigned
|   | so far then
|   | |   Find the maximum expression level gene pair (g1, g2, e)
|   | |      where g1 is the assignment for the barcode X1;
|   | |   Assign g2 to barcode X2.
|   | end
|   end
end
```

This algorithm comprises the steps of generating a list of barcode tuples (i.e., a tuple consisting of any two of the designed barcodes and a weight equal to the edit distance (e.g., the Hamming distance) between them), and also generating a list of gene tuples (i.e., a tuple consisting of any two of the target genes and a weight equal to their mean expression level). The tuple formulation has the advantage over the approach described in Algorithm 3 that it "aligns" a graph of designed barcodes with a graph of target genes such that the edge weights of the graphs are correlated, i.e., more distant barcodes are aligned with highly expressed genes. Algorithm 3 associates the designed barcode and target gene nodes of the graph regardless of the pairwise weights (edges). It should be noted that this algorithm may be configured to alternatively or additionally iterate through gene tuples as well as barcode tuples when assigning designed barcodes to the corresponding gene transcripts.

Decoded Barcode Error Correction

The nearest neighbor barcode error correction algorithm (Algorithm 2) described above provides theoretical guarantees for barcode error correction and reasonable performance. However, real-life decoding methods are not always perfect. It is often difficult to characterize their associated error models, as the decoding methods (and decoding modules configured to implement them) are typically not fully optimized and can exhibit noisy performance during development. In some instances, decoding performance may be limited by physics (e.g., imaging system resolution and other imaging system performance parameters) as well as by limitations of the decoding chemistry employed. Accordingly, better empirical performance guarantees may be rooted in better modeling of the decoding processes.

Figure 8:
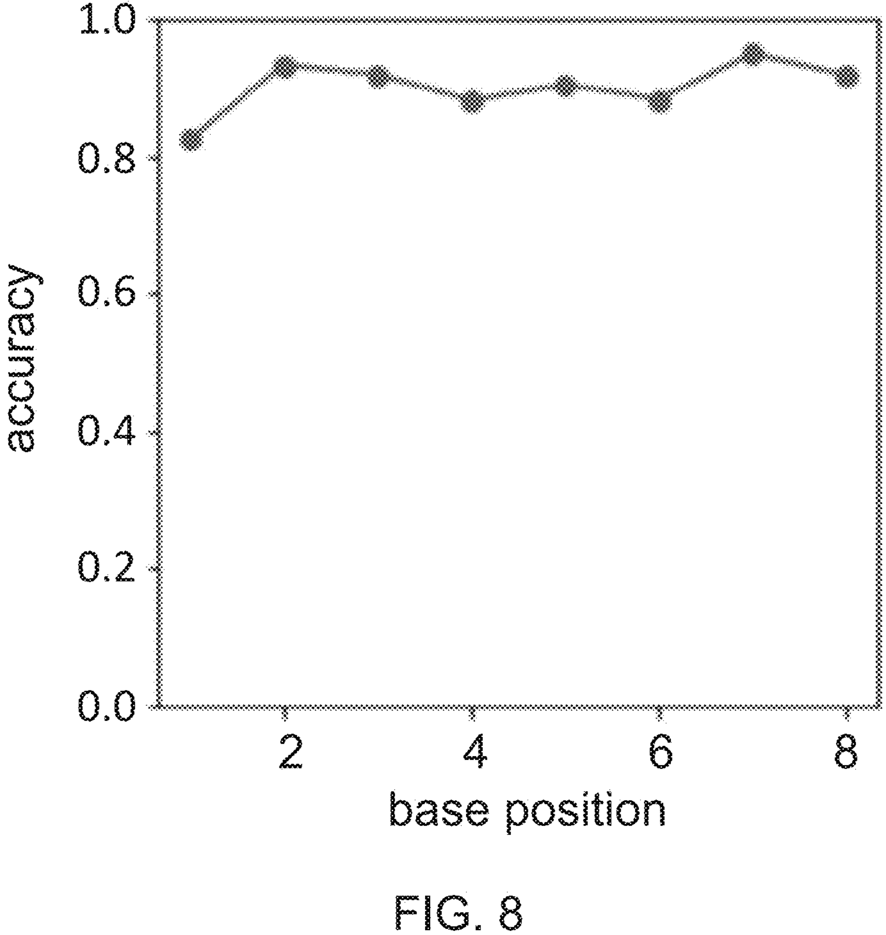
FIG. 8 is a graph of an exemplary decoding accuracy data as a function of base position.

As a non-limiting example of barcode decoding and error rates, FIG. 8 provides a plot of decoding accuracy data over 8 cycles of sequencing from dense nucleotide decoding experiments involving 600 distinct barcodes that are 8 nucleotides long and have a pairwise Hamming distance of $H_D \geq 3$, and that were designed using Algorithm 1 described above. The designed barcodes were attached to 2000 features with known locations on a flow cell surface. They were then decoded via 8 cycles of a three color, four state (3C4S) decoding chemistry. The decoding accuracies for each base position could be evaluated because the ground truth label (i.e., the designed barcode) for each spatial location on the flow cell was controlled as part of the experiment design. A basic state caller algorithm was used to identify the state/letter associated data points in the signal intensity domain (e.g., similar to a basecaller). The decoding accuracies are seen in FIG. 8, where the mean accuracy of decoding was 90.3%, and decoding cycle 1 exhibited the least accurate decoding of all at 82.5%. At such high rates of error, the use of Algorithm 2 for error correction may not provide the best performance guarantees.

In this regard, an improvement to the nearest neighbor error correction algorithm may be implemented. The nearest neighbor correction algorithm of Algorithm 2 works if the query barcode (e.g., a decoded barcode) Y is within an error radius k of a designed barcode X provided that the designed barcode set $\chi$ has a property of a pairwise Hamming distance $H_D \geq 2k+1$. If the query barcode Y is within the empty space between the spheres of correction 11 (FIG. 1), the query barcode Y is generally uncorrectable at large decoding error rates.

Figure 9:
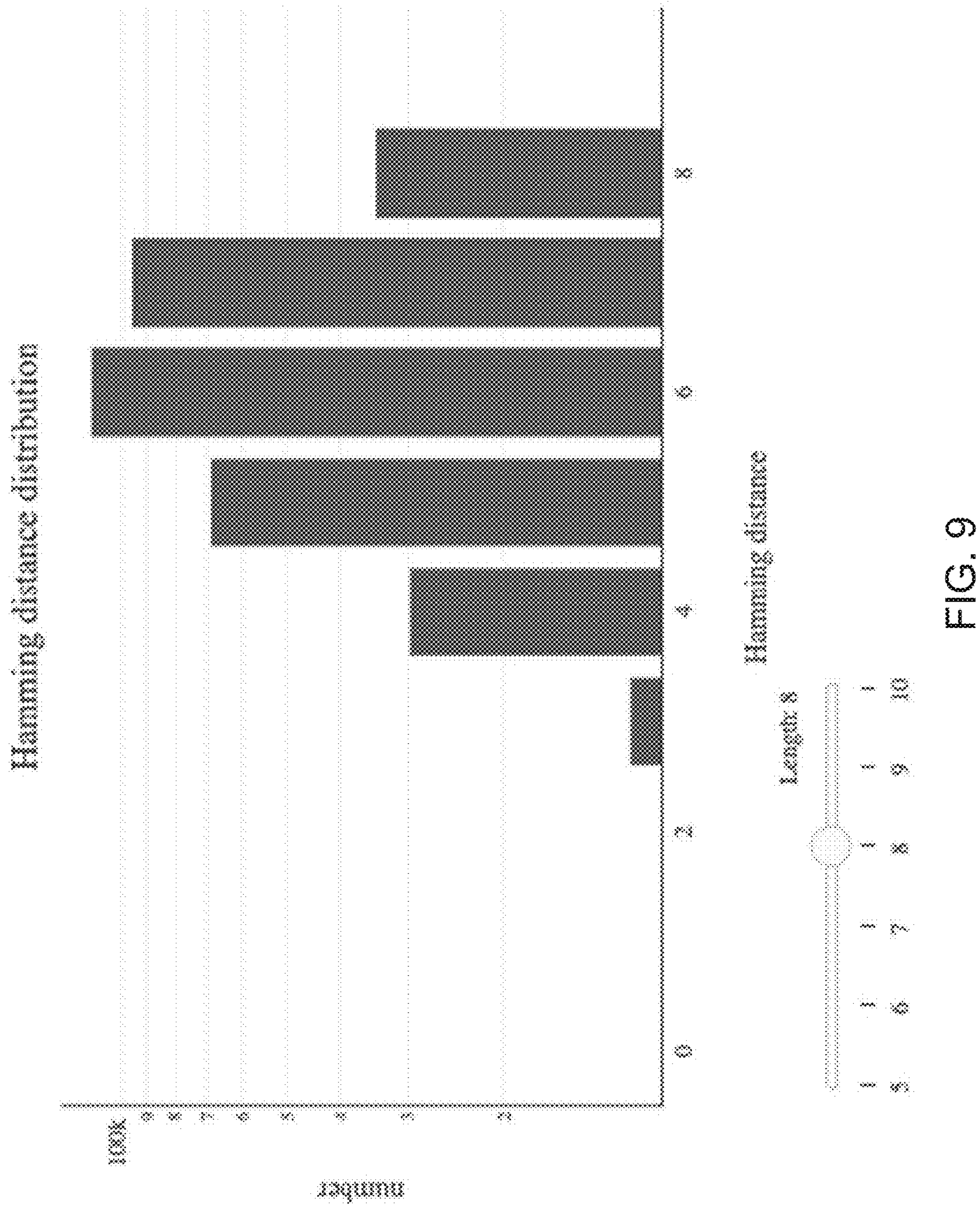
FIG. 9 is a plot of an exemplary distribution of pairwise Hamming distances for barcodes of length 8 with a minimum pairwise Hamming distance equal to three.

FIG. 9 illustrates a distribution of pairwise Hamming distances $H_D$ for the set of 600 algorithmically designed barcodes in this example. As can be seen, most pairwise Hamming distances are much greater than 3. In fact, it is difficult to observe a good "volume" covering of the metric space of the designed barcodes with the spheres of correction 11 having a radius of 1 (e.g., even when maximally filled).

If the designed barcodes are much further apart than a distance of 2k+1 (e.g., on average), the nearest neighbor search radius may be increased. This would allow conversion of some of the uncorrectable query (decoded) barcodes into true positive corrections, with a small fraction of the query (decoded) barcodes being converted into false positive corrections. The following algorithm (Algorithm 5) illustrates an improved nearest neighbor barcode correction, in one exemplary embodiment.

Algorithm 5: Improved Nearest Neighbor Barcode Correction

```
Result: Set of corrected barcode sequences 𝒴'
Initialize empty set of final corrected sequences 𝒴';
Initialize a BKTree storing the available design sequences χ;
foreach barcode Y drawn from thc observed barcodes 𝒴 do
|    Find 𝒵 = neighbors of Y within distance n in χ;
|    if 𝒵 is not empty then
|    |    Rank the neighbors found in 𝒵 by distince to Y;
|    |    Insert the closest neighbor Y' into 𝒴';
|    else
|    |    Insert Y into 𝒴';
|    end
end
```

Figure 10:
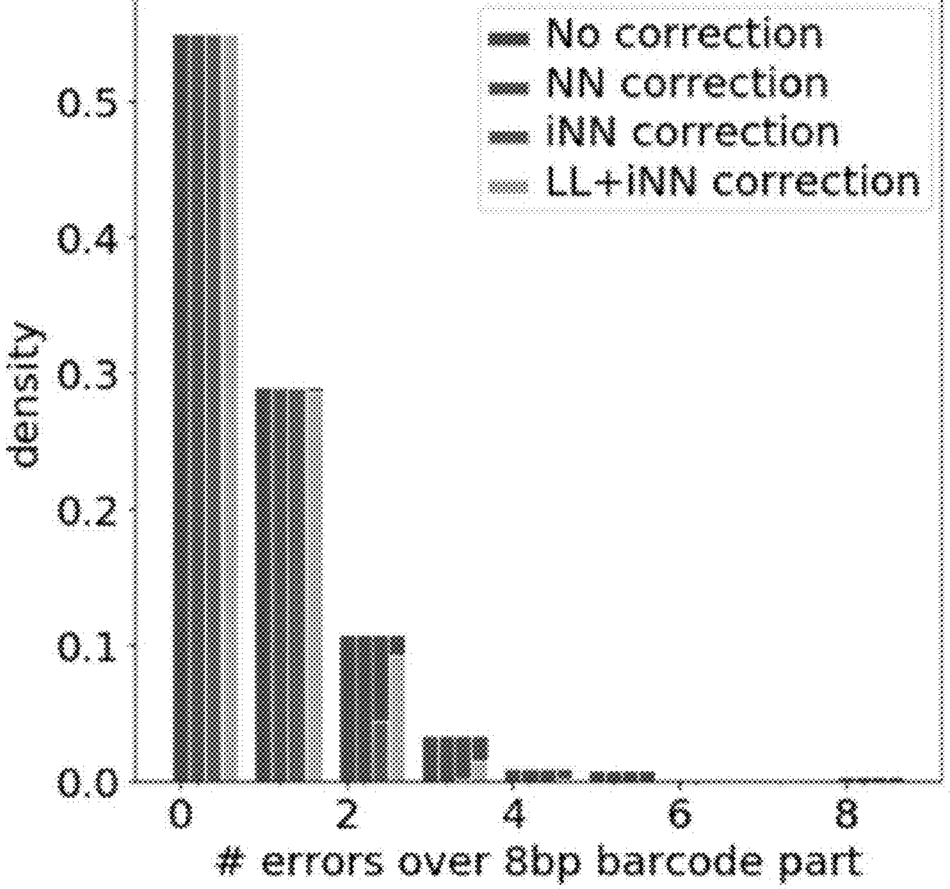
FIG. 10 is a plot of an exemplary distribution of the number of errors corrected per barcode sequence for barcode sequences of length 8 using various exemplary correction algorithms.

The search radius n is a parameter which is empirically set such that the false positive corrections do not dramatically increase. With n≥k, the TPR improves, as illustrated in FIG. 10. In FIG. 10, the blue (left most) bars indicate the distribution of the number of uncorrected errors observed over 8 decoding cycles of a barcode. The per cycle accuracy may be variable, but on average, the number of errors appears to be approximately binomially distributed. Accordingly, the barcodes may be categorized into groups by the numbers of errors made in state calling. The largest group is the "no errors" group. Green (second from left), red (third from left), and orange (right most) bars in each cluster indicate the proportion of the barcodes for each category that were error corrected via various algorithms to a known ground truth label (i.e., a true positive correction). The green bars (second from left) correspond to the data for correction using nearest neighbor algorithm, Algorithm 2. The red bars (third from left) correspond to the data for correction using the improved nearest neighbor correction algorithm, Algorithm 5 (e.g., with a search radius of n=4). As can be seen, even barcodes with two errors are corrected to some extent. However, a higher false positive rate may be incurred at the expense of a lower uncorrected rate.

Other error correction algorithms may be employed to improve true positive corrections for decoded barcodes. For example, state calling involves identifying clusters and signal intensity feature vectors plotted (e.g., as illustrated in FIG. 3 above). As part of the decoding process, "soft" calls may be generated by providing $|\hat{\mathcal{A}}_i| \times L$: probabilities as $\mathbb{P}_{\theta_i}$, (l=letter|$f_i$=feature vector) for each spatial feature of a given decoding cycle i. Here, $\theta_i$ are the cycle-specific model parameters, feature vector $f_i$ at a given spatial feature at cycle i are signal intensity vectors, and $l \in \hat{\mathcal{A}}_i$. With this in mind, a full log likelihood of the decoded sequence may be computed as follows:

$$ll_0(Y;F) = \log \mathbb{P}_{\theta}(Y \mid f) = \sum_{l \leq \iota \leq L} \log \mathbb{P}_{\theta_i}(y_i \mid f_i)$$

Thus, for each spatial feature, a corrected barcode sequence Y may be selected that has the maximum likelihood of explaining the observed signal intensities. The following algorithm, Algorithm 6, illustrates how such error correction may be performed, in one exemplary embodiment:

Algorithm 6: Loglikelihood Barcode Correction

Result: Set of corrected barcode sequences $\mathcal{Y}'$
Initialize empty set of final corrected sequences $\mathcal{Y}'$;
Store a $|\mathcal{A}_i| \times L$ probability table obtained by statecalling for each spatial feature j at cycle i: $\mathbb{P}_{0_i}(l|f_i^j)$ $(l \in \mathcal{A}_i, 1 \leq i \leq L)$;
for barcode $Y^j$ at each spatial feature j do
| Find $Y^{j'} = \arg\max_{\chi \in \chi} ll_0(X; f^j) = \arg\max_{\chi \in \chi} \Sigma_i \log \mathbb{P}_{0_i}(x_i|f_i^j)$;
| Insert $Y_j'$ into $\mathcal{Y}'$;
end This algorithm may be computationally costly as the "arg max" term is performed over an exponentially large set of barcodes χ for every decoded spatial feature. To improve computation speed, another algorithm (Algorithm 7) leverages the efficient nearest neighbor search enabled by BKTree data structures first to find a short list of candidates within χ that could be potential corrections of a decoded barcode sequence Y. Then, the algorithm may select the maximum log likelihood candidate from the shortened list of candidates as follows:

Algorithm 7: Loglikelihood + Improved Nearest Neighbor Barcode Correction

Result: Set of corrected barcode sequences $\mathcal{Y}'$
Initialize empty set of final corrected sequences $\mathcal{Y}'$;
Store a $|\mathcal{A}_i| \times L$ probability table obtained by statecalling for each spatial feature j at cycle i: $\mathbb{P}_{0_i}(l|f_i^j)(l \in \mathcal{A}_i, 1 \leq i \leq L)$;
for barcode $Y^j$ at each spatial feature j do
| Find $\mathcal{Z}$ = neighbors of $Y^j$ within distance n in χ;
| if $\mathcal{Z}$ is not empty then
| | Find
| | $Y^{j'} = \arg\max_{\chi \in z} ll_0(X; f^j) = \arg\max_{\chi \in z} \Sigma_i \log \mathbb{P}_{0_i}(x_i|f_i^j)$;
| | Insert $Y^{j'}$ into $\mathcal{Y}'$;
| else
| | Insert Y into $\mathcal{Y}'$;
| end
end The orange (right most) bars in FIG. 10 correspond to the data for corrections provided by Algorithm 7. This error correction algorithm shows even better performance than the improved nearest neighbor correction algorithm (i.e., Algorithm 5). A significant fraction of decoded barcodes with three or more errors appear to be corrected successfully.

Figure 11:
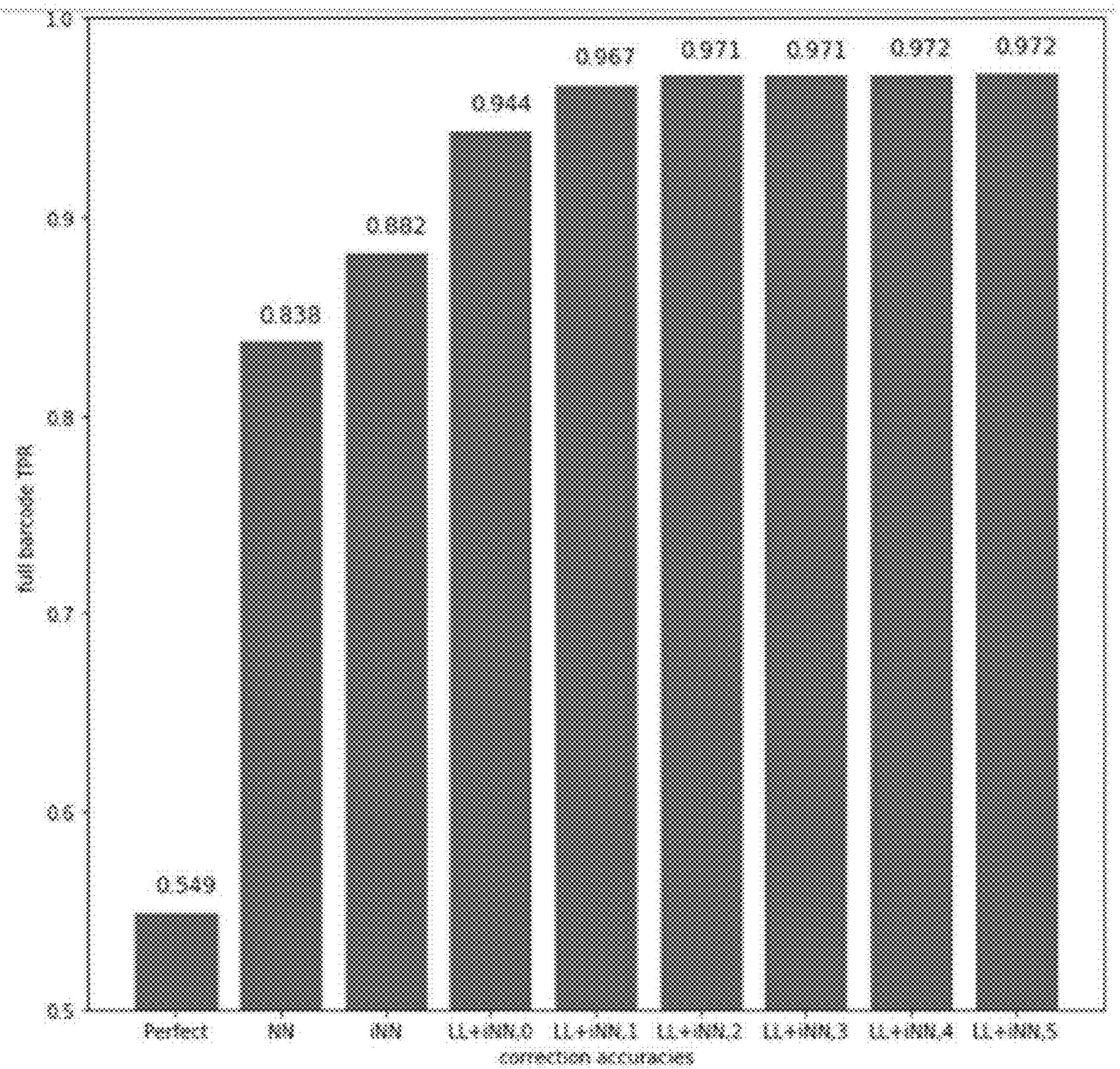
FIG. 11 is a plot showing an exemplary comparison of true positive rates for barcode correction of nucleic acid barcodes of length 8 using the various exemplary correction algorithms described herein.

FIG. 11 illustrates a comparison of TPR achieved for a full eight base barcode correction using the different error correction algorithms described herein. It can be seen that the fraction of uncorrected full-length barcodes that match with their ground truth labels is a mere 55%. This is intuitive as a 90.3% mean accuracy over eight decoding cycles as determined for the example provided above means the fraction of perfectly matching decoded barcodes is around $(0.903)^8$ which equals 45% (e.g., assuming that the errors from different cycles in the decoding process are not correlated). With the nearest neighbor (NN) correction (i.e., Algorithm 2), the TPR improves to 84%. With the improved nearest neighbor (iNN) correction algorithm (Algorithm 5), the TPR is further improved to 88%. However, with the combined log likelihood and improved nearest neighbor (LL+iNN,0) correction algorithm (Algorithm 7), the TPR improves to 94.4%.

Iterative Barcode Error Correction

Decoding methods and modules provide a means for detecting and determining a plurality of barcoded labels distributed over a plurality of spatial features. However, even though a given barcode is derived from a designed list χ of barcodes, a reference ground truth of tuples (e.g., barcode and spatial location) for evaluating the performance of the decoding process is not always available. Discovering this reference ground truth is the ultimate goal of most decoding methods and modules.

The error correction algorithms presented herein lend themselves naturally to the development of a general class of expectation maximization (EM) algorithms. For example, in an expectation step, for each spatial feature the decoding process may be used to determine a "hidden" reference barcode via a maximum likelihood correction of an observed (e.g., state called or decoded) barcode. In the maximization step of the EM algorithm, the decoding process may update the probabilistic state caller model parameters using the estimated reference barcode set as the new decoded barcode calls. Then, the decoding process may iteratively run the expectation and maximization steps to further improve the performance of the state caller and the reference barcode estimates until there is a convergence where, for example, the state calling model parameters do not change significantly from one cycle to the next, or where a maximum number of iterations has been reached.

This may be formalized as follows:

1. Let $\theta=[\theta_1, \ldots, \theta_L]$ be the state calling model parameters across L decoding cycles;
2. Let $$f^j = [f_1^j, \ldots, f_L^j]$$

be the collection of signal intensity data (e.g., fluorescence signal intensities) at each cycle for a spatial feature j; and
3. Let $$z^j = z_1^j \ldots z_L^j \in \chi$$

be the unknown/hidden reference barcode sequence at spatial feature j.

Thus, for a log likelihood correction of the $j^{th}$ sequence (e.g., similar to Algorithm 6), the decoding process may seek to maximize $\log \mathbb{P}_{\theta}(z|f^j)$ over the barcode set χ to obtain a point assignment $z^j$ as the correction. However, because the z values are hidden states of the data, the decoding process should instead maximize $\log \Sigma_{z \in \chi} \mathbb{P}_{\theta}(f^j, z)$, which may be achieved using the above-mentioned EM algorithm as exemplarily implemented in Algorithm 8 as follows:

Algorithm 8: Soft Iterative Log-likelihood Barcode Correction

Result: Set of corrected barcode sequences $\mathcal{Y}'$
Initialize empty set of final corrected sequences $\mathcal{Y}'$;
Store a $|\mathcal{A}_i| \times L$ probability table obtained by statecalling for each spatial feature j: $\mathbb{P}_{\theta'}(l \mid f^{i}, )(l \in \mathcal{A}_i, 1 \le i \le L)$;
Set t = 0; repeat
At iteration i:
E: Calculate the conditional likelihoods, i.e. the probabilities for all $z \in \chi$ given the signal at the feature j:
$Q_j^t(z) = \mathbb{P}_{\theta'}(z \mid f^j) = \Pi_{1 \le i \le L}(z_i \mid f_i^j)\ \forall j$;
M: Update the parameters of statecalling by solving this weighted maximum likelihood:

$$\theta^{t+1} = \text{argmax}_\theta \sum_j \sum_{z \in X} Q_j^t(z) \log \frac{\mathbb{P}_s(j^j, z)}{Q_j^t(z)} =$$

$\text{argmax}_\theta\ \Sigma_j \Sigma_{z \in \chi} Q_j^t(z) \log \mathbb{P}_{\theta'}(z \mid f^j)$;
$i := t + 1$
until convergence: $\|\theta^{t+1} - \theta^t\| < \epsilon$ or $t > T_{max}$;
At convergence, run Log-likelihood correction algorithm 6 with the final $\theta^{T'}$ to get point corrections $Y^{j'}$ for each spatial feature j and collect into $\mathcal{Y}'$;

Although the description of Algorithm 8 indicates that a probability table is stored, in some instances, state-calling probabilities may be provided directly by a probabilistic model (e.g., a random forest model or a neural network) instead of, or in addition to, being stored in a table. Algorithm 8 may be somewhat computationally slow due to the evaluation of the conditional probabilities for an exponentially large set $\chi$ in the expectation step, and because the update of the model parameters in the maximization steps involves maximizing over a summation of the same exponentially large set. To overcome this computational complexity, the decoding method may perform a hard assignment by replacing the conditional likelihood with a point assignment as follows:

$$Q_j^t(z) = 1\{z = \arg\ \max_{2 \in X} \mathbb{P}_{\theta^t}(z \mid f^j)\}.$$

This is generally the same as performing the likelihood-based decoding method of Algorithm 6, further accelerated by the efficient nearest neighbor search utilized in Algorithm 7. Because the probability mass is concentrated on the point correction $z^j$ (effectively assigning $z^j$ as the corrected barcode) the weighted likelihood equation simplifies to $\theta^{t+1} = \arg\ \max_\theta \Sigma_j \log \mathbb{P}_\theta(z^j \mid f^j)$. In this regard, a "hard" iterative log likelihood barcode correction is presented in exemplary Algorithm 9 as follows:

Algorithm 9: Hard Iterative Log-likelihood Barcode Correction

Result: Set of corrected barcode sequences $\mathcal{Y}'$
Initialize empty set of final corrected sequences $\mathcal{Y}'$;
Store a $|\mathcal{A}_i| \times L$ probability table obtained by statecalling for each spatial feature j: $\mathbb{P}_{0_i}(l \mid f_i^j)(l \in \mathcal{A}_i, 1 \le i \le L)$;
Set t = 0; repeat
At iteration t:
E: Calculate the hard point assignment $z^j$ for each spatial feature via Log-likelihood + nearest neighbor correction algorithm 7:
$z^j = \arg\ \max_{z \in \chi} \mathbb{P}_0^{\,i}(z \mid f^j)$;
M: Update the parameters of statecalling by solving this standard maximum likelihood: $\theta^{t+1} = \arg\ \max_\theta \Sigma_j \log \mathbb{P}_0(z^j \mid f^j)$;
$t := t + 1$
until convergence $\|\theta^{t+1} - \theta^t\| < \epsilon$ or $t > T_{max}$;
At convergence, run the E step with the final $\theta^{Tj}$ to get point corrections $Y^{j''}$ for each spatial feature j and collect into $\mathcal{Y}'$;

The performance for this algorithm is illustrated in FIG. 11 with the bars labeled "LL+iNN" indicating correction using the log likelihood plus improved nearest neighbor approach for the $0^{th}$, $1^{st}$, $2^{nd}$, $3^{rd}$, $4^{th}$, and $5^{th}$ iterations, respectively. Convergence occurred with a true positive rate of 97.2%.

Similar to the hard and soft versions of the EM algorithms described above, a truncated iterative log likelihood correction algorithm (Algorithm 10) is also presented herein. Instead of evaluating the conditional likelihoods for all $z \in \chi$ and/or performing point assignments, the truncated iterative log likelihood correction algorithm may evaluate likelihoods for z in the relatively small neighborhood of the sequence $Y_t^j$ called by a state caller at the iteration t. This confines the maximization step to a much smaller neighborhood in edit distance space. And, the $Q_j^t$ values are no longer proper probabilities because they do not sum to 1. This, however, does not present a problem as the weighted likelihood in the maximization step is linear in those conditional probabilities. Algorithm 10 is exemplarily illustrated as follows:

Algorithm 10: Truncated Iterative Log-likelihood Barcode Correction

Figure 12:
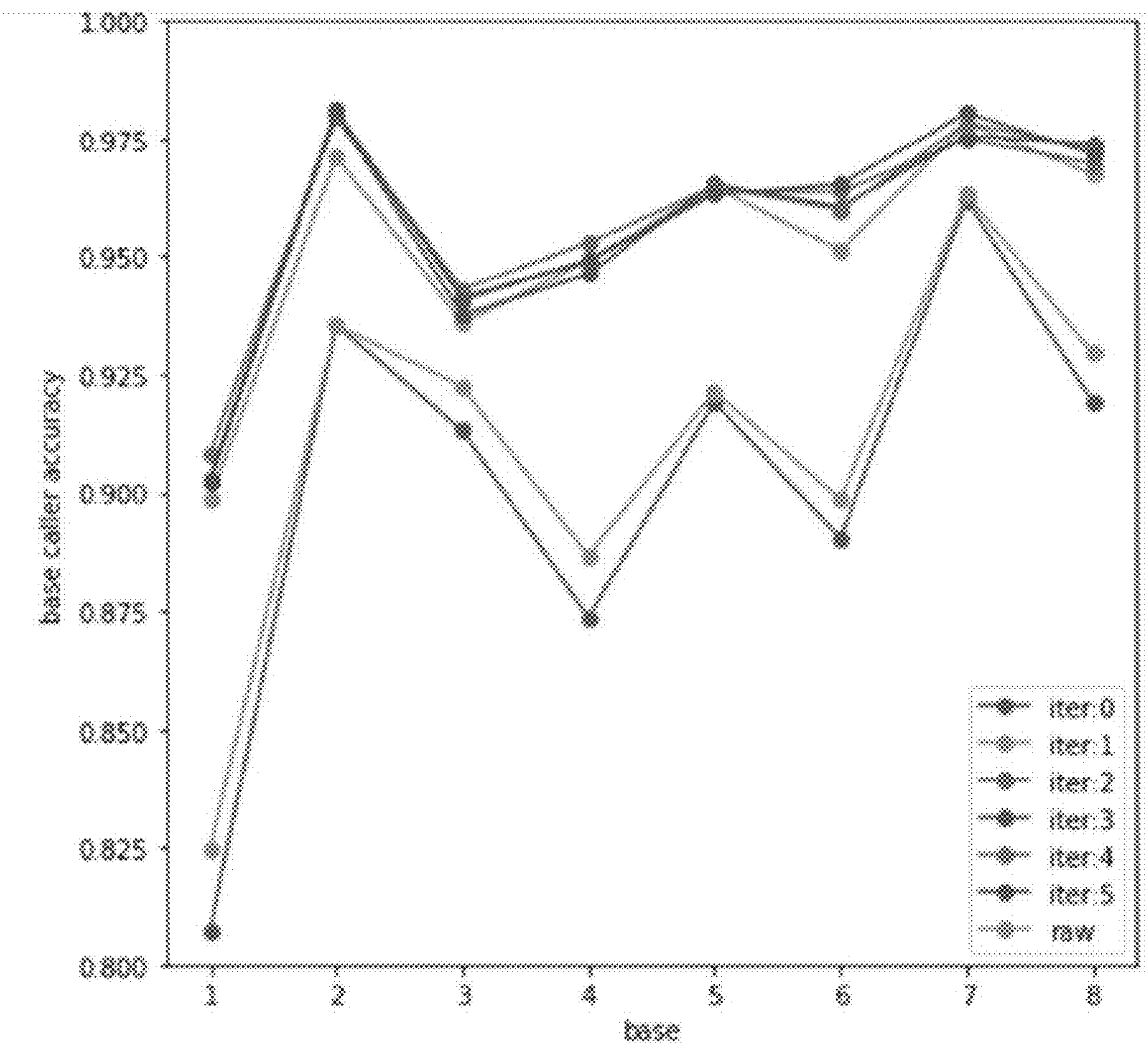
FIG. 12 is a graph illustrating exemplary base calling accuracy for nucleic acid sequencing as a function of base position after tuning the base caller (e.g., a state caller) using an iterative error correction method.

Result: Set of corrected barcode sequences $\mathcal{Y}'$
Initialize empty set of final corrected sequences $\mathcal{Y}'$;
Store a $|\mathcal{A}_i| \times L$ probability table obtained by statecalling for each spatial feature j: $\mathbb{P}_{0_t}(l \mid f_i^j)(l \in \mathcal{A}_i, 1 \le i \le L)$;
Set t = 0; repeat
At iteration t:
E:
Determine the decoded sequence letters at each cycle $1 \le i \le L$ as
$Y_{t,i}^j := \arg\ \max_i \mathbb{P}_{\theta_t}(l \mid f_i^j)$.
Find the neighbor set $\mathcal{Z}^j \subseteq \chi$ of radius n for the full sequence $Y_t^j$.
Evaluate the truncated conditional likelihoods only for $z \in \mathcal{Z}^j$:
$Q_j^t(z) = \mathbb{P}_0^{\,t}(z \mid f^j) = \mathbb{P}_{1 \le i \le L} \mathbb{P}_{\theta_i'}(z_i \mid f_i^j)\ \forall j$;
M:
Update the parameters of statecalling by solving this truncated weighted maximum likelihood:
$\theta^{t+1} = \arg\ \max_\theta \Sigma_j \Sigma_{z \in Z^j} Q_j^t(z) \log \mathbb{P}_0(z \mid f^j)$;
$t := t + 1$
until convergence: $\|\theta^{t+1} - \theta^t\| < \epsilon$ or $t > T_{max}$;
At convergence, run the algorithm 7 with the final $\theta^T{}_j$ to get point corrections $Y^j$ for each spatial feature j and collect into $\mathcal{Y}'$;

At convergence, e.g., when the state calling model parameters do not change significantly from one cycle to the next, or when number of iterations has exceeded a set maximum $t > T_{max}$, a probabilistic state caller $\mathbb{P}_{\theta \tau_f}$ is obtained that has been adaptively tuned to the chemistry and hardware performance of the decoding module configured for that individual decoding run. Every new run may provide a new tune model parameter $\theta^{T_j}$. This probabilistic state caller effectively adapts to variations in chemistry and hardware performance. In general, the decoding cycle accuracy may depend on the decoding module hardware (e.g., optofluidics), biochemistry, and/or algorithmic model complexity. The iterative algorithms disclosed herein (e.g., Algorithms 8-10) may remove or minimize the algorithmic effect on decoding accuracy, as is illustrated in FIG. 12 which provides a graph of exemplary base calling accuracy data for nucleic acid sequencing as a function of base position after tuning the base caller (e.g., a state caller) using the "hard" iterative error correction method. As can be seen in FIG. 12, individual decoding cycle accuracy is improved with each iteration of error correction.

Figure 13:
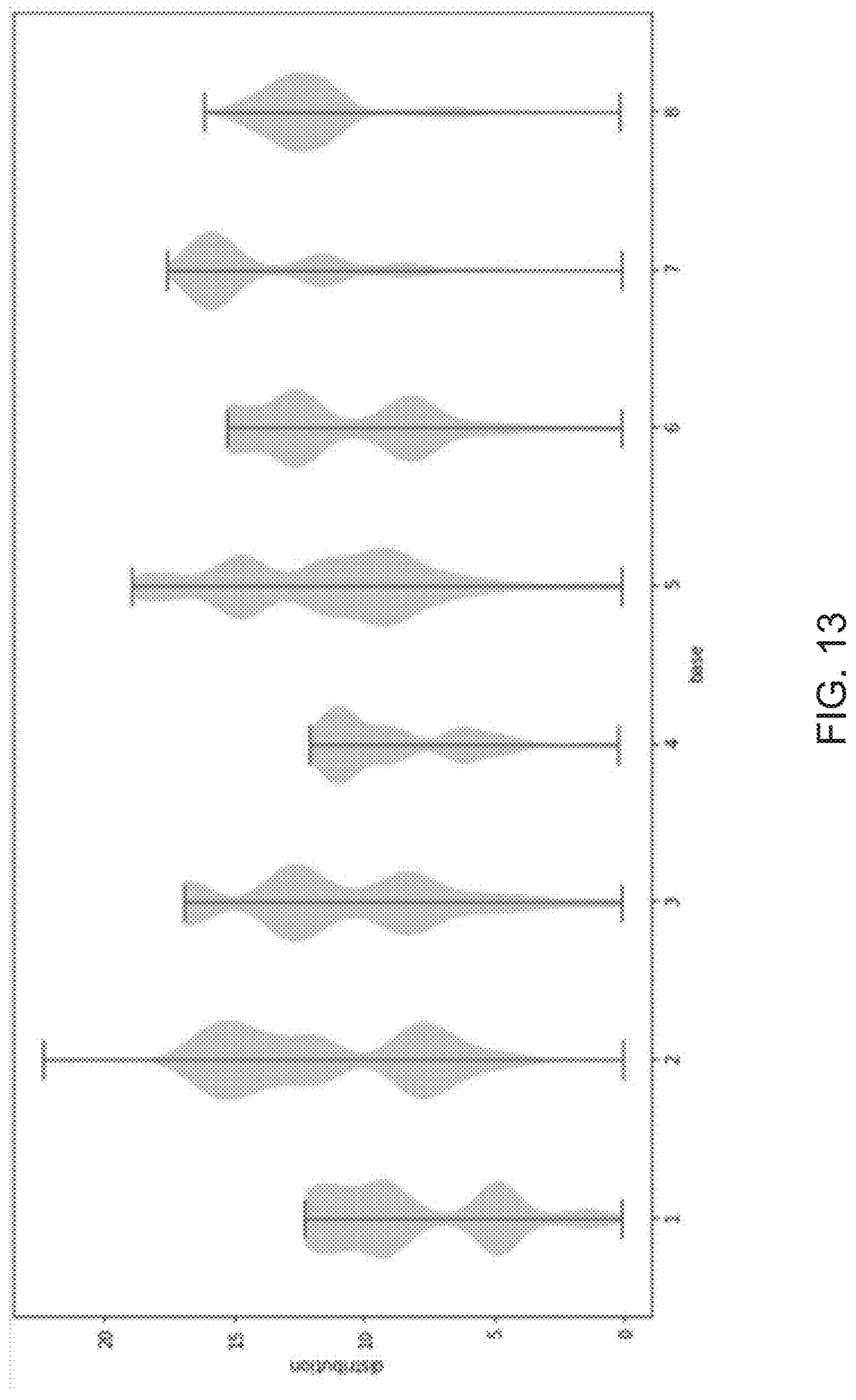
FIG. 13 is a graph of exemplary PHRED quality score distributions from a tuned base caller (e.g., a state caller) for nucleic acid sequencing.

From there, PHRED-like quality scores that signify the confidence in the state calls obtained directly from $\mathbb{P}_{\theta \tau_f}(l \mid f^j)$ may be determined, as illustrated in FIG. 13. For example, PHRED scores may be mathematically defined as $-10 \log_{10}$ $\mathbb{P}$(error), where the error is an incorrect state call and P(error) is the probability of making an incorrect state call. FIG. 13 illustrates the distribution of PHRED quality scores for each decoding cycle (i.e., a position in an 8 nucleotide barcode), where the width of the distribution indicates the frequency of data points occurring at a specified quality score. In this example, the distributions are shifted to higher quality when the tuned state caller accuracy is higher.

Figure 14:
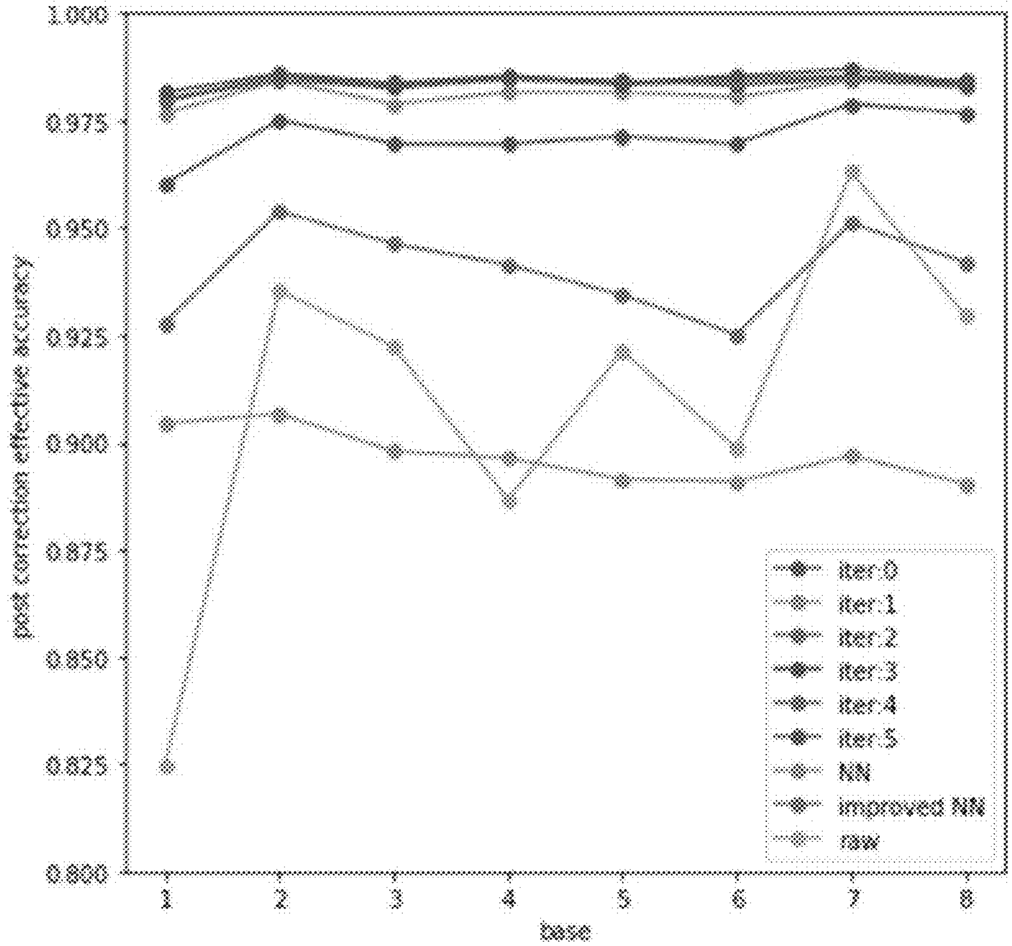
FIG. 14 is a graph illustrating exemplary post-correction decoding accuracy as a function of base position for a tuned base caller (e.g., a state caller).

A decoded barcode sequence set $\mathcal{Y}'$ that corresponds closely to the ground truth reference (or designed) barcode sequences may be obtained for the barcodes at each spatial feature by virtue of the iterative error correction process. This can be seen in FIG. 14 where the corrected barcodes were compared to the known ground truth designed barcodes to extract a per position post-correction decoding accuracy. Starting within 82.5% raw sequencing accuracy, the "hard" iterative error correction method improves the accuracy to 98% for decoding cycle 1. This is not to be confused with the adaptively tuned state caller performance for decoding cycle 1, which is lower (e.g., 90% as illustrated in FIG. 12) as the tuned state caller at convergence may still make errors there was no additional correction applied. This provides a method of evaluating accuracies of decoding processes that are purely attributable to chemistry and hardware performance by comparing the barcode sequences predicted by the tuned state caller and their corrected sequences.

The maximization step of the EM algorithm, in its simplest form, assumes that the feature vector for a spatial feature j is the signal intensity at the feature $f^j$. Other forms of the feature vector can be developed that include, but not limited to, the following additional aspects:

1. Location of a feature, used to model, e.g., large-scale spatial variations (e.g., flow cell edges with weaker signals);
2. Neighborhood signal values, to account for local spatial variation (e.g., bubbles, local autofluorescence, etc.); and
3. Oligo sequence context, to account for decoding chemistry biases.

Model Parameters θ

The probabilistic state calling model that provides $\mathbb{P}_{\theta_i}(l|f_i)$ prior to executing the iterative procedure does not necessarily need to be the same as the model being updated in the maximization step. Accordingly, the t=0 state calling can comprise relatively crude estimates in which the decoding method utilizes rough probabilities before initiating the expectation step. The decoding method comprises updating the new model in the maximization step. This formulation implicitly assumes that the probabilistic model used in the maximization step is a discriminative model (e.g., a classifier). The weighted likelihood maximization procedure is thus akin to training a classifier. The crude state calling step at t=0 thus may be performed by an unsupervised machine learning model, as reference labels (states) are not known. Indeed, Algorithm 9 uses a relatively crude unsupervised state caller to estimate probabilities prior to initiating the iterative procedure. In the EM iterations, the algorithm may employ a random force classifier. However, Algorithm 9 may also be implemented using, for example, artificial neural networks, deep learning models, and/or by Bayesian models to capture other effects, such as oligonucleotide sequence context, barcode probe binding kinetics, fluorophore photobleaching kinetics, and/or image registration algorithm parameters, that may impact the probabilities of detecting a given state at a given location in a given decoding cycle. The EM algorithm could also be regularized with a prior set of model parameters θ. Furthermore, the expectation step may be modified to "mix in" the probabilities from the previous iteration to control the learning rate of machine learning-based EM processes.

Bead Array Decoding

The various barcode design, decoding method, and error correction methods described herein are not intended to be limited to any specific type of barcoding technique. For example, each of the disclosed decoding methods may be implemented for in situ detection applications, spatial array applications, bead array applications, etc. In bead array applications, for example, designed barcode sequences may be constructed combinatorially, with the DNA sequences for each segment or part satisfying some specified Hamming distance criterion. Barcodes attached to beads in the array are basically randomly sampled from a designed barcode set constructed from, for example, $\chi_1 \times \chi_2 \times \chi_3$ for a three-part barcode, where each part of the barcode may be decoded and error corrected using the methods described herein.

Figures 15A, 15B:
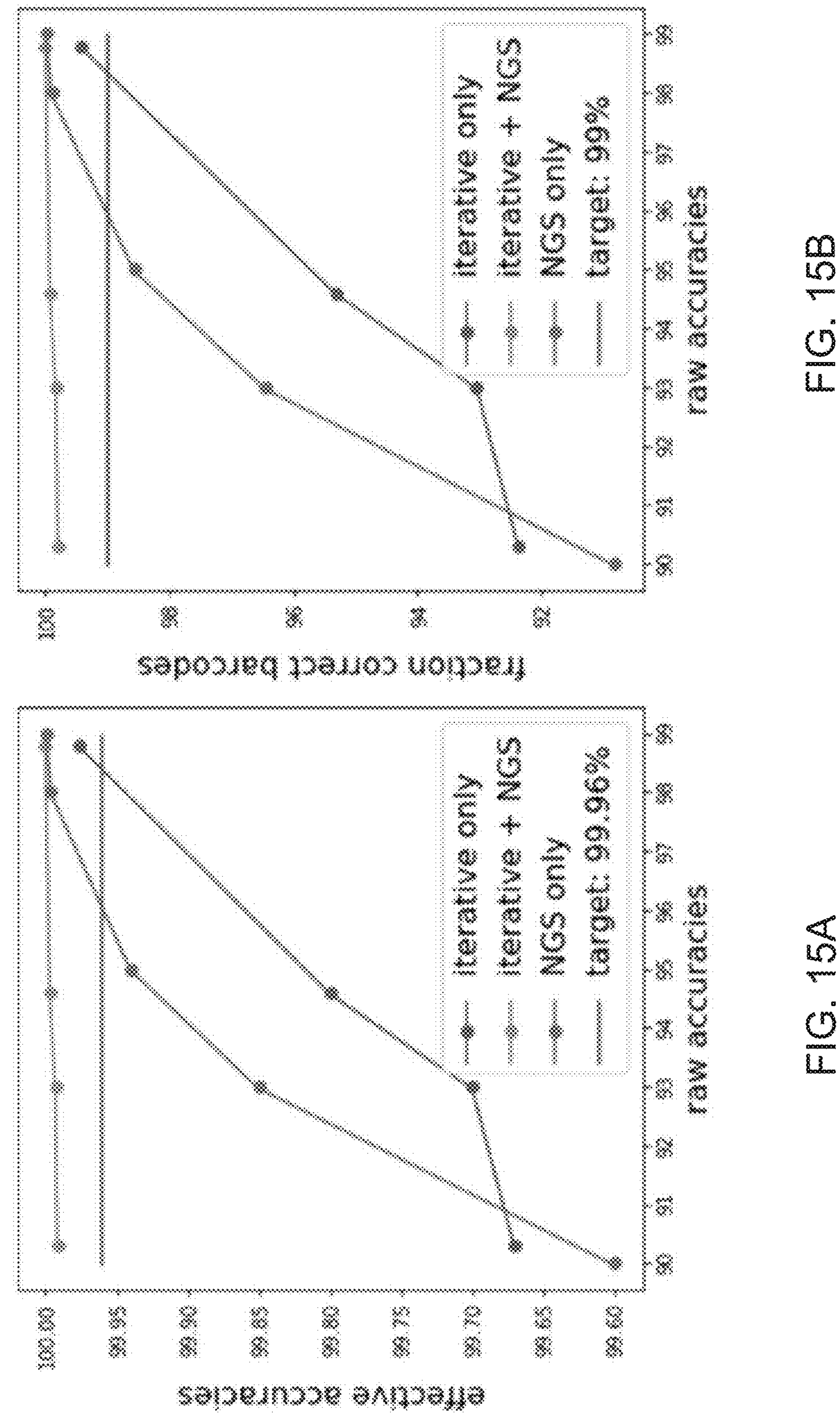
FIG. 15A is a graph illustrating state caller performance (i.e., effective accuracy) obtained using different error correction methods as a function of raw decoding accuracies.
FIG. 15B is a graph illustrating state caller performance (i.e., the fraction of correctly called barcodes) obtained using different error correction methods as a function of raw decoding accuracies.

FIGS. 15A and 15B illustrate plots for iterative log likelihood plus improved nearest neighbor error correction performance (e.g., blue curves) over three-part nucleic acid (A, T, G, C) barcodes for 2,000 barcodes that were 8 nucleotides in length and had a minimum Hamming distance of 3. The x-axes are the raw decoding cycle accuracies for a crude state caller without correction or tuning. Effective single base accuracies post correction are plotted in FIG. 15A, where error correction comprised the use of the iterative error correction algorithm only, the use of next generation sequencing (NGS) only (i.e., to directly determine the actual barcode sequences), or a combination of NGS data and iterative error correction. Barcode correction TPR is plotted in FIG. 15B, where error correction again comprised the use of the iterative error correction algorithm only, next generation sequencing (NGS) only, or a combination of NGS and iterative error correction. As can be seen, even at a raw decoding cycle accuracy as low as 90%, iterative error correction improves the effective accuracy to 99.6%. And, a raw accuracy as low as 96% to 97% is sufficient to obtain improved accuracies of 99.9+ percent. These accuracies, though aided by adaptive/iterative correction, are comparable to modern NGS sequencing accuracies.

The methods described herein may also be applicable to short read sequencers. For example, when developing new short read sequencing chemistry for compatibility with specified sequencing hardware, a chemist may desire to evaluate the chemistry performance and optimize it using various experiment designs. One experiment that is often used includes genome sequencing of a fully known microbial genome. The resulting short read sequences may then be aligned to the known microbial genome with high fidelity, and the accuracy of sequencing may be extracted such that quality scores are calibrated for every repeat of the specific experiment until the chemistry becomes stable. This is often cumbersome and costly.

Accordingly, one short read sequencer embodiment of the disclosed methods may be implemented as follows.

1. Design a set of barcode sequences $\chi$ with pairwise Hamming distance properties of $H_D \geq 2k+1$;
2. Decode the sequences of these barcodes on a flow cell in a sequencing experiment;
3. Perform iterative error correction based on the known set of designed barcodes $\chi$;

4. Evaluate the chemistry and hardware performance based on the PHRED scores and sequencing accuracies obtained using an adaptively trained state caller (e.g., obtained from the iterative correction algorithms above); and
5. Based on the more accurate readout of the chemistry and hardware performance, optimize both aspects (e.g., using a new set of designed barcode sequences $\chi$ in an adaptive sense).

Short read sequencer chemistry can suffer when sequencing homopolymer regions of DNA and/or DNA regions with relatively high guanine-cytosine (GC) content. The sequencer performance can also suffer when one of the four nucleotides is not present at a given base position within all fragments. To overcome these issues, a phi-X control is often introduced (e.g., on-the-fly alignment to the phiX reference sequence may be used to calculate sequencing error rates).

Instead of spiking in a phi-X control, the following sequencer experimental design may not only help minimize all of these failure modes and/or biases, but may also dynamically improve sequencing accuracy for any kind of bias in a sequencing run. Such a short-read sequencer embodiment may be implemented as follows:

1. Design a set of barcode sequences $\chi$ that have appropriate pairwise Hamming distance separation. Pad these barcodes with a known sequence (or something to mark it is a barcode containing fragment);
2. For a sequencing run, introduce these barcode containing fragments instead of phi-X;
3. Run state calling to generate relatively crude probabilities $\mathbb{P}_\theta(l|\vec{f})$ for each sequence in a flow cell;
4. Run iterative error correction (e.g., the hard iterative log-likelihood, soft iterative log-likelihood, or truncated iterative log-likelihood error correction algorithms as described above) on the sequences marked as containing barcodes to obtained the adaptively tuned state caller probabilities $\mathbb{P}_{\theta\tau_f}(l|\vec{f})$; and
5. Predict all other sequences using the tuned state caller. In this regard, the training set, from the point of view of machine learning, is the designed set of barcode sequences $\chi$ and their observed signal intensities. The test set is all other observed signal intensities.

Similarly, this adaptive algorithm may be employed with long read sequencers as long as a custom set of long barcodes $\chi$ can be designed with the desired edit distance properties as described herein. In many long-read sequencers, insertion, deletion, and substitution are principle sources of errors. To deal with these errors, the barcode design should be operable in the Levenshtein distance space or the general edit distance space. The various correction algorithm methods shown and described herein may still be valid, with the difference that the nearest neighbor searches would be in the Levenshtein distance or edit distance space. In some instances, log likelihood decoding may be more complex as the state caller model in long read sequencers typically includes hidden Markov models.

For in situ transcriptomics, barcode decoding is done in up to three dimensions for each decoding cycle. Because of the use of the OFF letter $\eta$ shown and described above to reduce optical crowding in some embodiments, the decoding process can be designed to ensure that no single decoding cycle comprises visualization of all the barcoded target RNA molecules. Accordingly, the target RNA spots detected in each decoding cycle are computationally registered such that, across all decoding cycles, they decode to the known barcodes. This registration can be potentially problematic because of experimental factors such as local tissue deformation and background autofluorescence levels.

Barcode-Assisted Image Registration and Alignment

Also disclosed herein are methods for barcode-assisted image registration, alignment, and stitching (or tiling) to create composite images that may be used to reduce or eliminate problems associated with, for example, the swelling or shrinking of tissue samples for in situ detection and sequencing applications.

The registration problem may be cast as an optimization problem where three-dimensional images and/or point clouds detected in each decoding cycle are aligned across cycles such that a large fraction of the decoded barcode sequences are easily correctable to the designed set of barcodes. Mathematically, registration algorithms involve maximizing a reward function $J(\phi)$ where $\phi$ values are the deformation model parameters. This may be interpreted as a maximum likelihood problem, and one can include the local registration process as part of a state caller model $\mathbb{P}_\theta(l|\vec{f})$ that includes the registration parameters $\phi$ in the model parameters $\theta$. With this, one of the iterative correction algorithms disclosed herein may be used to refine, update, and/or tune all of the algorithmic parameters as captured by $\theta$ and thereby produce higher quality alignments and decoding performance simultaneously.

Exemplary EM Algorithm

The EM algorithm is useful for generally any type of modeling that involves hidden variables and spaces. For example, assume that your data is $\{x^{(i)}: i=1 \ldots N\}$ generated from a probability distribution $\mathbb{P}_\theta(x)$ that has been parameterized by $\theta$. Now, assume that the data has hidden factors $z \in \mathcal{Z}$ that explain the observation x and thus the total probability of an observation is a summation over hidden factors: $\mathbb{P}_\theta(x)=\Sigma_z \mathbb{P}_\theta(x, z)$. The log likelihood can then be expressed as:

$$l(\theta) = \sum_i \log \sum_{z^{(i)} \in \mathcal{Z}} \mathbb{P}_\theta(x^{(i)}, z^{(i)})$$

If $z^{(i)}$ were observed, the log likelihood takes a much simpler form and the estimation of $\theta$ is less complex. Instead of maximizing $l(\theta)$ by setting the partial derivatives to zero, a lower bound to $l(\theta)$ is established as the expectation step. That bound is then maximized repeatedly as part of the maximization step. Accordingly, let $z^{(i)} \sim Q_i(z)$ be the distribution of $z^{(i)}$. Using Jensen's inequality for logarithms, $$\log\left(\sum_k Q(k)b(k)\right) \geq \sum_k Q(k)\log(b(k)) \text{ for } \sum_k Q(k) = 1,\ b(k) > 0.$$

Thus, the lower bound on the log likelihood at a given $\theta$ may be constructed as follows:

$$l(\theta) = \sum_i \log \sum_{z^{(i)} \in \mathcal{Z}} \mathbb{P}_\theta(x^{(i)}, z^{(i)}) = \sum_i \log\left(\sum_{z^{(i)}} Q_i(z^{(i)}) \frac{\mathbb{P}_\theta(x^{(i)}, z^{(i)})}{Q_i(z^{(i)})}\right)$$

-continued $$\geq \sum_i \sum_{s^{(i)}} Q_i(z^{(i)}) \log \frac{\mathbb{P}_\theta(x^{(i)}, z^{(i)})}{Q_i(z^{(i)})}.$$

This is a lower bound for any distribution $Q_i$. The lower bound is an equality at a current θ if b(k) is constant. That is, $Q_i(z^{(i)}) \propto \mathbb{P}_\theta(x^{(i)}, z^{(i)}) \Rightarrow Q_i(z^{(i)}) = \mathbb{P}_\theta(z^{(i)}|x^{(i)})$. With this choice of $Q_i$, the lower bound on the log likelihood remains a lower bound on the maximized log likelihood. Then, this lower bound is maximized with respect to θ to obtain a new estimate, which can then be used to find a new $Q_i$, and so on. Thus, the EM algorithm may be summarized as:

Repeat until convergence:

$$E: Q_i^t(z^{(i)}) = \mathbb{P}_{\theta i}(z^{(i)}, x^{(i)}) \forall i$$

$$M: \theta^{t+1} = \underset{\theta}{\operatorname{argmax}} \sum_i \sum_{z^{(i)}} Q_i^t(z^{(i)}) \log \frac{\mathbb{P}_\theta(x^{(i)}, z^{(i)})}{Q_i^t(z^{(i)})}$$

Usually, the maximization step is computationally difficult and may require approximation methods. When $z^{(j)}$ is known and not hidden, the expectation step becomes unnecessary and the maximization step simply becomes the statement of maximizing the standard log likelihood of $x^{(i)}$ for a given θ.

The log likelihood is improved by the expectation algorithm by picking new estimates of θ. To illustrate, at iteration t+1:

$$l(\theta^{t+1}) \geq \sum_i \sum_{z^{(i)}} Q_i^t(z^{(i)}) \log \frac{\mathbb{P}_{\theta^{t+1}}(x^{(i)}, z^{(i)})}{Q_i^t(z^{(i)})} \ldots \text{by Jensen's inequality}$$

$$\geq \sum_i \sum_{z^{(i)}} Q_i^t(z^{(i)}) \log \frac{\mathbb{P}_\theta(x^{(i)}, z^{(i)})}{Q_i^t(z^{(i)})} \ldots \text{by M-step}$$

$$= \sum_i \log\left(\sum_{z^{(i)}} Q_i^t(z^{(i)}) \frac{\mathbb{P}_\theta(x^{(i)}, z^{(i)})}{Q_i^t(z^{(i)})}\right) \ldots \text{by E-step}$$

$$= l(\theta^t)$$

The EM algorithm can also be viewed as a coordinate ascent on $$J: l(\theta) \geq J(Q, \theta) = \sum_i \sum_{z^{(i)}} Q_i^t(z^{(i)}) \log \frac{\mathbb{P}_\theta(x^{(i)}, z^{(i)})}{Q_i^t(z^{(i)})},$$

where the expectation step maximizes J with respect to Q, and the maximization step maximizes J with respect to θ.

If the model parameters have a prior distribution $\mathbb{P}_\mu(\theta)$, parameterized by hyper parameters μ that are fixed, then instead of the probability $\mathbb{P}_\theta(x)$, the full probability $\mathbb{P}_\theta(x)\mathbb{P}(\theta) = \Sigma_x \mathbb{P}_\theta(x, z)\mathbb{P}(\theta)$ that incorporates the prior needs to be considered. The log likelihood thus has an additional "regularizer" term corresponding to the prior N (i.e., the total number of data points) as follows:

$$l(\theta) = \sum_i \log \sum_{z^{(i)} \in \mathcal{Z}} \mathbb{P}_\theta(x^{(i)}, z^{(i)}) + N \log \mathbb{P}(\theta).$$

The lower bound is now:

$$l(\theta) \geq \sum_i \sum_{z^{(i)}} Q_i(z^{(i)}) \log \frac{\mathbb{P}_\theta(x^{(i)}, z^{(i)})}{Q_i(z^{(i)})} + N \log \mathbb{P}(\theta).$$

The expectation step corresponding to a fixed θ is thus the same as before the expectation step requiring computation of the posterior distribution of the hidden variable. The maximization step is now a weighted map estimate step that incorporates the prior as a regularizer to stabilize the estimate as follows:

$$M: \theta^{t+1} = \underset{\theta}{\operatorname{argmax}} \left[\sum_i \sum_{z^{(i)}} Q_i^t(z^{(i)}) \log \frac{\mathbb{P}_\theta(x^{(i)}, z^{(i)})}{Q_i^t(z^{(i)})} + N \log \mathbb{P}(\theta)\right].$$

Systems for Barcode Design and Decoding

Figure 16:
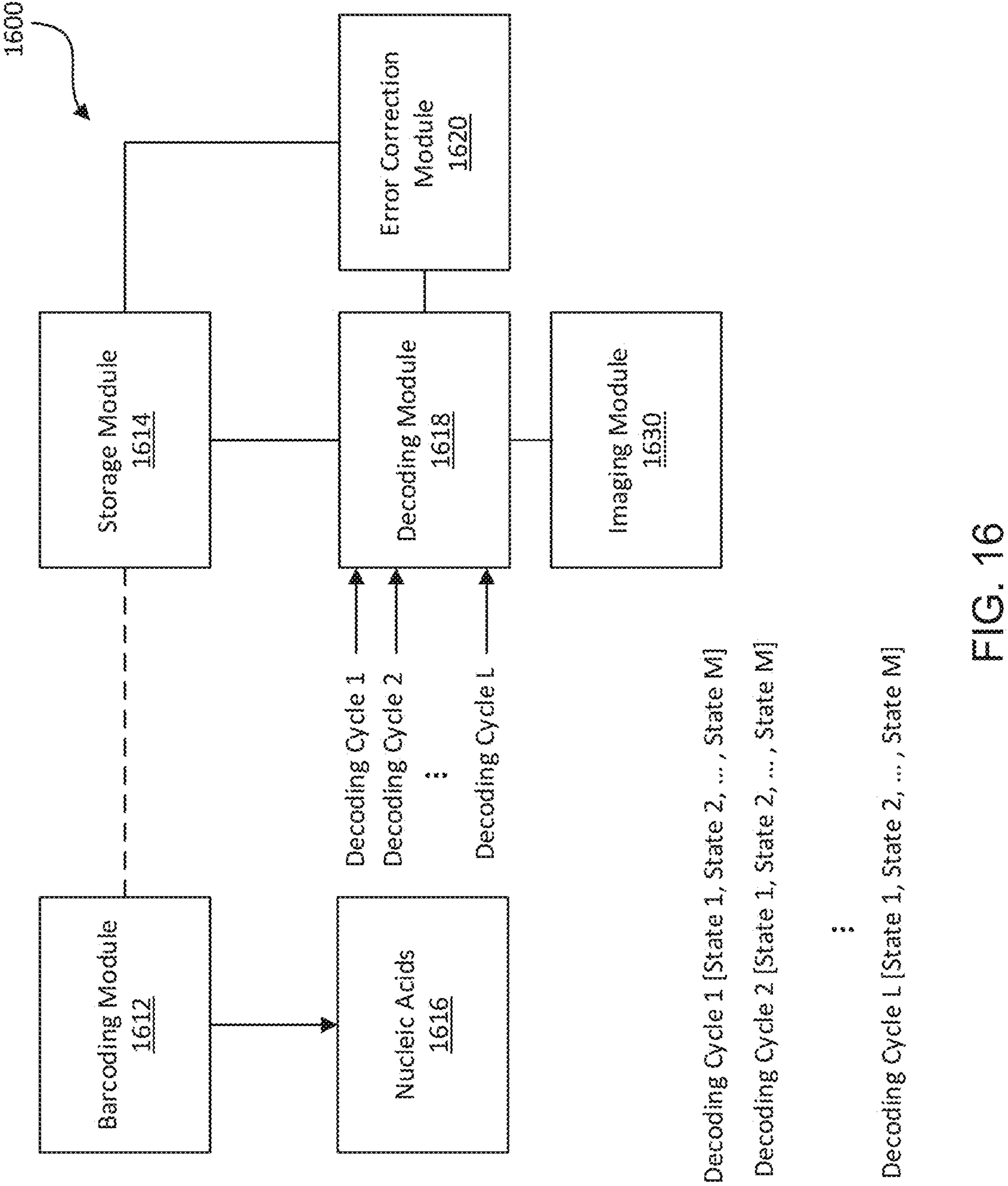
FIG. 16 is a block diagram of an exemplary system 100 for encoding gene sequences or other target entities with barcodes and for decoding the barcoded gene sequences or other target entities.

FIG. 16 is a block diagram of an exemplary system 1600 for designing barcodes to encode gene transcripts and decode barcoded gene transcripts (or for designing barcodes to encode other target analytes and decode barcoded analytes). In some instances, system 1600 may comprise one or more processors, a barcoding module 1612, a storage module 1614, a plurality of target nucleic acids 1616 (or other target analytes), an imaging module 1630, a decoding module 1618, and an error correction module 1620, or any combination thereof. It should also be noted that the system components described herein, such as barcoding module 1612, storage module 1614, imaging module 1630, decoding module 1618, and the error correction module 1620, can take the form of hardware, software, or a combination thereof. In some instances, software may include, but is not limited to, firmware, resident software, microcode, etc.

In some instances, the one or more processors may comprises stand-alone processors or computers that constitute components of system 1600 and function as controllers to control communication between, and to coordinate the activities of, one or more other functional modules of system 1600, e.g., barcoding module 1612, storage module 1614, imaging module 1630, decoding module 1618, and/or error correction module 1620. In some instances, the one or more processors may be integrated with one or more other functional modules of system 1600, e.g., barcoding module 1612, storage module 1614, imaging module 1630, decoding module 1618, and/or error correction module 1620.

In some instances, barcoding module 1612 is operable to design a set of barcodes that meet a set of design criteria for a specific application using any of the barcode design algorithms described herein. In some instances, barcoding module 1612 is operable to select barcodes from a "candidate barcode pool" (e.g., a digital candidate barcode pool stored in storage module 1614) that meet the specified design criteria and thus create a set of designed barcodes. In some instances, barcoding module 1612 is operable to assign individual barcodes from a set of designed barcodes to individual target analytes from a set of target analytes, e.g., target nucleic acid molecules 1616 (such as target gene transcripts or mRNA molecules). In some instances, the barcoding module 1612 is operable to assign individual barcodes from a set of designed barcodes to individual target analytes from a set of target analytes by calculating, e.g., an edit distance metric, rank ordering the designed barcodes according to the calculated edit distance metric, rank ordering the target analytes according to, e.g., corresponding gene expression levels, and assigning designed barcodes to target analytes according to their ranks. In some instances, the assigned barcodes may then be incorporated into, e.g., a set of barcoded target capture probes and/or barcoded target detection probes as described elsewhere herein. In some instances, barcoding module 1612 is operable to control a manufacturing process used to synthesize the designed barcodes (e.g., through control of an automated nucleic acid synthesizer or automated peptide synthesizer). In some instances, barcoding module 1612 is further operable to control a manufacturing process used to produce arrays (e.g., through control of an automated liquid dispensing, liquid spotting system, or synthesizer to cause the attachment of barcodes from a set of designed barcodes to, e.g., features of a spatial array, or the beads of a bead array). In some instances, the barcoding module 1612 is further operable to design a decoding process that matched to a specific set of designed barcodes.

In some instances, storage module 1614 is operable to store a list of candidate barcodes, e.g., using a metric tree data structure that enables efficient search capabilities. In some instances, storage module 1614 is operable to store a set of designed barcodes, e.g., using a metric tree data structure that enables efficient search capabilities. In some instances, storage module 1614 is operable to store a probabilistic model (or a representation thereof, such as a probability table) that provides probabilities for detecting a given barcode sequence, or segment (code word) thereof, at a given location in a given decoding cycle based on a set of detected signals (e.g., fluorescence signals).

In some instances, imaging module 1630 is operable to generate an image (e.g., an image of a tissue specimen, spatial array, bead array, sequencing flow cell, and the like) for each cycle of a decoding process used to detect and decode barcodes (or to detect and decode target analyte sequences, such as mRNA sequences). In some instances, imaging module 1630 is further operable to register the images from a plurality of decoding cycles to locations of one or more of the detected and decoded barcode sequences (or detected and decoded target analyte sequences) in the images, and to align the images based on the registration. In some instances, imaging module 1630 is operable to generate an image tile for each decoding cycle, identify at least a subset of the detected and decoded barcode sequences (or detected and decoded target analyte sequences) in one image tile that correspond to detected and decoded barcode sequences in an overlapping region of another image tile, and stitch the image tiles together based on the identified subset of the detected and decoded barcode sequences.

Figure 17:
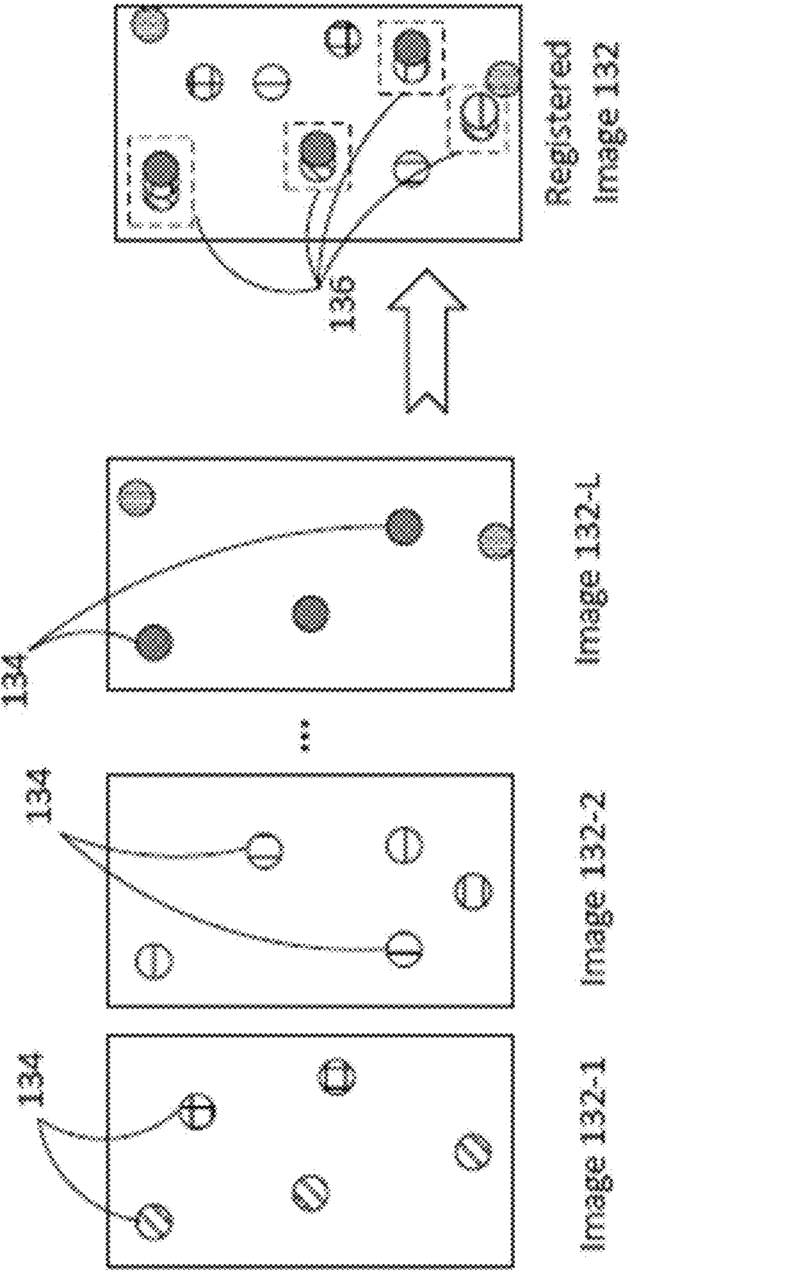
FIG. 17 illustrates an exemplary process for registering a plurality of images to locations of detected barcode sequences in the images.

For example, in some instances, the system 1600 includes an imaging module 1630 that is operable to generate an image for each decoding cycle. As illustrated in FIG. 17, during each decoding cycle i, the imaging module 1630 may generate an image 132-*i* that indicates the locations of labeled barcode probes detected during the decoding cycle. Once certain barcode sequences have been detected, decoded, and error corrected (e.g., using any of the error correction algorithms described herein), the imaging module 130 may register the series of images 132-1, 132-2, . . . 132-L to the locations of one or more detected barcode sequences 134 in the images 132-1, 132-2, . . . 132-L, and align the images 132-1, 132-2, . . . 132-L based on the registration to generate a registered image tile 132.

To illustrate, different barcode segments 134 are illustrated with different fills (e.g., cross-hatching, dots, etc.) in each of the series of images 132. The imaging module 1630 may first generate the image 132-1 for decoding cycle 1 such that the image 132-1 indicates a location for a plurality of detected barcode segments 134. Then, the imaging module 1630 may generate the image 132-2, and so on, until the last decoding cycle L is complete and the image 132-L has been generated. The imaging module 1630, with the assistance of the error correction module 1620, determines the locations of one or more decoded sequences 136 that have been error corrected and aligns the images 132-1, 132-2, . . . 132-L to those locations to generate a final registered image (i.e., the registered image tile 132).

In some instances, the imaging module 1630 may identify a corrected barcode sequence across a plurality of images 132-1, 132-2, . . . 132-L that has a predetermined minimum quality score or degree of confidence. For example, the corrected barcode sequence selected for image registration may have a confidence level of at least 80%, 90%, 95%, 98%, or 99% as calculated, e.g., from the probability of a corrected barcode sequence arising from one of the known designed barcode sequences. The imaging module 1630 may then align the images 132-1-132-L based on the location of the barcode sequence. The imaging module 1630 may then select another corrected barcode sequence with a predetermined minimum quality score or degree of confidence to realign the images 132-1-132-L, and so on, such that the decoding module 1618 may be utilized to optimize the image registration. In some instances, image registration may be performed based on the locations of one or more corrected barcode sequences that match one or more predetermined barcode sequences. In some instances, image registration may be performed based on the locations of one or more randomly selected corrected barcodes. In some instances, image registration may be performed based on the entire set of corrected barcodes.

In some instances, once image registration is complete for a given field-of-view, a series of image tiles 138-1, 138-2, . . . for different fields-of-view may be used to construct a composite or panoramic image (e.g., by stitching together adjacent image tiles) that identifies the locations of a plurality of barcoded spatial features across, e.g., a flow cell surface or spatial array substrate. However, the individual image tiles 138-1, 138-2, . . . typically do not align perfectly, and overlapping regions of adjacent image tiles may display the same barcoded features.

In some instances, the imaging module 1630 may compensate for alignment and overlap issues for adjacent image tiles by identifying portions of adjacent image tiles, e.g., image tile 138-1 and image tile 138-2, that correspond to one another such that they may be correctly aligned to generate the panoramic image. For example, the decoding module 1618 may detect and decode the sequences of a set of nucleic acid barcode sequences over a plurality of sets of decoding cycles. Each set of decoding cycles corresponds to a unique location or field-of-view of a substrate to which barcoded features are attached. The imaging module 1630, for each set of decoding cycles, may then generate an image 132-*i* for each decoding cycle i and register the images 132-1, 132-2, . . . 132-L from a given set of decoding cycles to locations of at least one of the detected barcode sequences in the series of images. The imaging module 1630 may thus generate an image tile 132 based on the barcode-assisted registration and alignment of images (as illustrated in FIG. 17) for each of the sets of decoding cycles.

Figure 18:
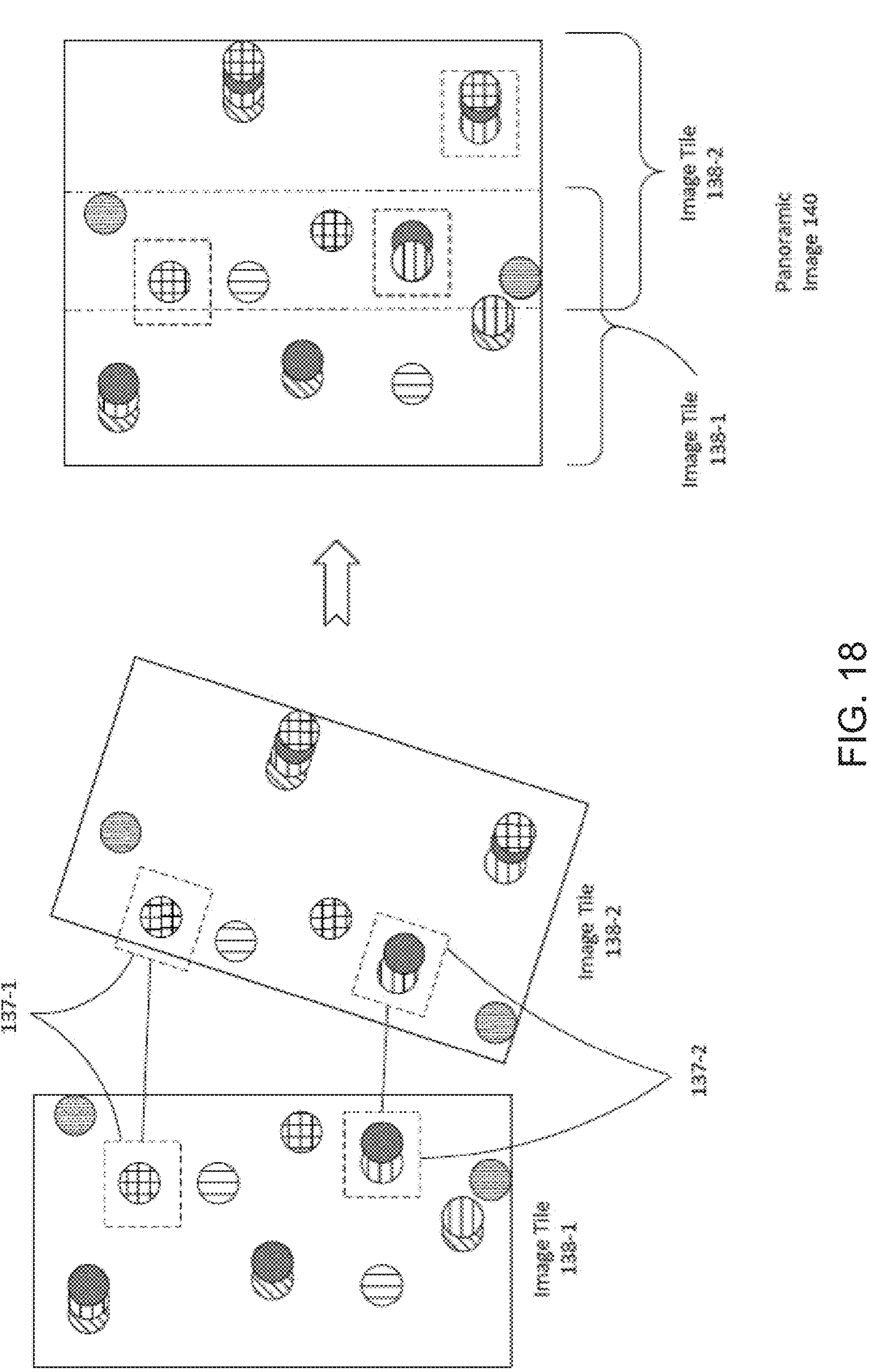
FIG. 18 illustrates an exemplary process for aligning and stitching adjacent image tiles based on the locations of detected barcode sequences in the images.

As illustrated in FIG. 18, the imaging module 1630 may identify locations for a portion of the detected barcode sequences (e.g., 137-1 and 137-2) in one image tile 138-1 that corresponds to a same portion of the detected barcode sequences (e.g., 137-1 and 137-2) in an adjacent image tile 138-2. The imaging module 1630 may then use the locations identified for the detected barcode sequences 137-1 and 137-2 in the image tiles 138-1 and 138-2 to align and stitch the image tiles 138-1 and 138-2 together. That is, the imaging module 1630 may align the adjacent image tiles 138-1 and 138-2, remove an overlapping portion of one of the image tiles, and stitch the image tiles 138-1 and 138-2 together to generate the panoramic image 140.

In some instances, the imaging module 1630 may perform the image alignment and stitching operation via a least squares optimization of the identified barcodes 137-1 and 137-2. For example, the imaging module 1630 may find a rigid transform (e.g., comprising a rotation R and/or a translation t) using unique barcodes in the overlap margins of the image tiles 138-1 and 138-2. This generally requires solving a linear algebra system of equations via least squares as follows: (image tile 138-2 coordinates)=R*(image tile 138-1 coordinates)+t, subject to the constraint that the dot product matrix $R^TR=I$ (the identity matrix). In some instances, the imaging module 1630 may find a non-rigid transform (e.g., comprising a scale change, a shear, stretching in one or more dimensions, or any combination thereof) using unique barcodes in the overlap margins of the image tiles 138-1 and 138-2.

In some instances, the imaging module 1630 may align the image tiles 138-1 and 138-2 based on a random sample consensus (RANSAC) approach by using random samplings of points (i.e., barcoded features) in image tile margins to reduce the number of duplicate barcodes selected for use in alignment and to generate multiple candidate transforms. The imaging module 1630 may also use a large plurality of corresponding barcodes detected in adjacent image tiles to perform a point set registration (e.g., a Coherent Point Drift, or "CPD", algorithm) to generate candidate transforms. Then, the imaging module 1630 may collect the generated transforms and determine which transform yields the most accurate image alignment (i.e., generates the highest alignment frequency (e.g., density) in the parameter space). The transformation selected in this case is rigid and can serve as starting point for determining local non-rigid stitching algorithms. In some instances, a non-rigid transformation may be determined using, e.g., a radial basis function, B-spline method, wavelet method, free form deformation (FFD) model, or any combination thereof. In some instances, a rigid or non-rigid transformation may comprise a two-dimensional transformation. In some instances, a rigid or non-rigid transformation may comprise a three-dimensional transformation.

It should be noted that FIG. 18 illustrates a simplified example of the image stitching operation. Typically, the imaging module 1630 may generate hundreds if not thousands of image tiles 138 that must be aligned and stitched. It should also be noted that these methods are not limited to use with barcode error correction based solely on Hamming distances, as other error correction techniques shown and described herein may also be used. For example, in some instances, the storage module 1614 may store a table of probabilities (or a probabilistic model that generates the probabilities) for a given barcode segment (code word) to be detected at a given location in a given cycle of the decoding process, and error correction module 1620 may correct the detected and decoded barcodes by replacing one or more of the decoded barcodes with a corresponding designed barcode that has a maximum likelihood as computed from a probability distribution (e.g., as computed from a log likelihood or negative log likelihood of the probability distribution (i.e., the probabilities compiled in the table or generated by the probabilistic model)), as shown and described above. In some instances, the methods for barcode-assisted image registration, alignment, and stitching described herein may be used either alone or in combination with conventional fiducials, e.g., features or objects placed in the field of view of the imaging module that appear in the images and may be used as points of reference. Examples of conventional fiducials include, but are not limited to, features etched or printed on a substrate surface, a bead or other visible objects (e.g., DAPI (4',6-diamidino-2-phenylindole) stained cell nuclei), etc.

In some instances, decoding module 1618 is operable to read out barcode sequences using optical microscopy-based imaging, electronic ion sensing, and/or other modalities of sensing. In some instances, for example, decoding module 1618 is operable to associate a color channel in an imaging module or system with a labeled barcode probe used to detect and decode a barcode sequence, or segment thereof (e.g., a letter or state), and to generate a series of decoding cycles for detecting and decoding a plurality of barcode sequences, as illustrated in FIG. 16.

In some instances, error correction module 1620 is operable to operable to identify and correct errors in decoded barcode sequences by replacing one or more of the decoded barcode sequences with a corresponding designed barcode that has a closest edit distance (e.g., a Hamming distance) to the decoded barcode sequence.

In some instances, error correction module 1620 is operable to identify and correct errors in the decoded barcode sequences by replacing one or more of the decoded barcode sequences with a corresponding designed barcode sequence that has a maximum likelihood as computed from the log likelihood (or negative log likelihood) of a probability distribution generated by a probabilistic model that provides probabilities for detecting a given barcode sequence, or segment (code word) thereof, at a given location in a given decoding cycle based on a set of detected signals (e.g., fluorescence signals) associated with a set of barcode probes used to detect the barcode sequences.

In some instances, error correction module 1620 is operable to identify and correct errors in decoded barcode sequences by replacing one or more of the decoded barcode sequences with a corresponding designed barcode sequence that: (i) is within a predetermined pairwise edit distance (e.g., a predetermined pairwise Hamming distance) from the decoded barcode sequence, and (ii) has a maximum likelihood as computed from the log likelihood (or negative log likelihood) for a probability distribution generated by a probabilistic model that provides probabilities for detecting a given barcode sequence, or segment (code word) thereof, at a given location in a given decoding cycle based on a set of detected signals associated with a set of barcode probes used to detect the barcode sequences.

In some instances, error correction module 1620 is operable to, for each decoded barcode sequence and until convergence, repeatedly: correct one or more decoded barcode sequences by replacement with one of the stored designed barcodes that has a maximum likelihood as computed from the log likelihood (or negative log likelihood) of a probability distribution generated by a probabilistic model that provides probabilities for detecting a given barcode sequence, or segment (code word) thereof, at a given location in a given decoding cycle based on a set of detected signals; and update the probabilistic model using the corrected barcode sequences. In some instances, the error correction module 1620 is further operable to, after convergence, correct each previously corrected barcode sequence with one of the designed barcodes that has a maximum likelihood as computed from the log likelihood (or negative log likelihood) of a probability distribution generated by the updated probabilistic model.

In some instances, error correction module 1620 is operable to, for each decoded barcode sequence and until convergence, repeatedly: correct one or more of the decoded barcode sequences with one of the stored designed barcodes that: (i) is within a predetermined pairwise edit distance (e.g., a predetermined pairwise Hamming distance) from the decoded barcode sequence (determined, for example, by rank-ordering the set of designed barcode sequences according to their pairwise edit distance from the detected and decoded barcode sequence), and (ii) has a maximum likelihood as computed from the log likelihood (or negative log likelihood) of a probability distribution generated by a probabilistic model that provides probabilities for detecting a given barcode sequence, or segment (code word) thereof, at a given location in a given decoding cycle based on a set of detected signals; and update the probabilistic model using the corrected barcode sequences. In some instances, the error correction module 1620 is further operable to, after convergence, correct each previously corrected barcode sequence with one of the designed barcodes that: (iii) is within a predetermined pairwise edit distance (e.g., a predetermined pairwise Hamming distance) of the previously corrected barcode sequence, and (iv) has a maximum likelihood as computed from the log likelihood (or negative log likelihood) of a probability distribution generated by the updated probabilistic model.

In some instances, error correction module 1620 is operable to, for each decoded barcode sequence and until convergence, repeatedly: correct one or more decoded barcode sequences by replacement with one of the stored designed barcodes that: (i) is within a predetermined pairwise edit distance (e.g., a predetermined pairwise Hamming distance) from the decoded barcode sequence (determined, for example, by rank-ordering the set of designed barcode sequences according to their pairwise edit distance from the detected and decoded barcode sequence), and (ii) has a maximum likelihood as computed from a truncated log likelihood (or negative truncated log likelihood) for a probability distribution generated by a probabilistic model that provides probabilities for detecting a given barcode sequence, or segment (code word) thereof, at a given location in a given decoding cycle based on a set of detected signals; and update the probabilistic model using the corrected barcode sequences. In some instances, the error correction module is further operable to, after convergence, correct each previously corrected barcode sequence with one of the designed barcodes that: (iii) is within a predetermined pairwise edit distance (e.g., a predetermined pairwise Hamming distance) of the previously corrected barcode sequence, and (iv) has a maximum likelihood as computed from the truncated log likelihood (or negative truncated log likelihood) for a probability distribution generated by the updated probabilistic model.

In some instances, the system 1600 may be configured to reduce false positive barcode corrections for barcodes associate with highly expressed gene transcripts and lower expressed gene transcripts. For example, the system 1600 may include a barcoding module 1612 that is operable to apply designed barcodes from a designed "barcode pool" to a plurality of nucleic acids 1616. In some instances, each assigned barcode is configured to target a portion of a specific target nucleic acid 1616. A decoding module 1618 is operable to generate a plurality of decoding cycles 1 . . . L (where the reference "L" is an integer greater than or equal to "1" and not necessarily equal to any other "L" reference designated herein), with each decoding cycle operable to detect up to "M" states (where the reference "M" is also an integer greater than or equal to "1" and not necessarily equal to any other "M" reference designated herein). The decoding cycles are operable to read-out the barcoded nucleic acids such that the decoding module 1618 may decode the barcoded nucleic acids 1616.

Generally, the number of decoding cycles that the decoding module 1618 generates is determined by the length of the barcodes being decoded. For example, with a barcode design comprising eight nucleotides, the decoding module 1618 may generate at least eight decoding cycles. The decoding cycles may be configured in such a way as to detect one or more nucleotides in each decoding cycle, as described above. Once the decoding cycles are complete, each of the nucleotides associated with a barcode is detected and the sequence of nucleotides is decoded.

A storage module 1614 may include a list of the designed barcodes selected from a candidate barcode pool and used to barcode the nucleic acids 1616. The decoding module 1618 may use this list of designed barcodes to develop decoding cycles to ensure that the barcodes are detected and thus decoded, as shown and described above.

After decoding is complete, the sequence of nucleotides may be read out and processed by an error correction module 1620. For example, the decoding module 1618 may be used to decode a plurality of barcoded nucleic acids 1616. It is possible that the one or more barcode sequences were read out incorrectly (e.g., due to noise in the decoding process). Thus, the error correction module 1620 may use the list of designed barcodes stored in the storage module 1614 to select a corrected barcode sequence using any of the correction algorithms described hereinabove.

In some embodiments, the barcoding module 1612 may assign designed barcode sequences to gene transcripts based on their corresponding gene expression levels. For example, each designed barcode may be assigned to, or configured to target, one of a plurality of gene transcripts of a sample. The barcoding module 1612 may rank the designed barcodes according to pairwise Hamming distances (or other pairwise edit distance) between the barcodes (e.g., by computing an average Hamming distance of each designed barcode relative to the other designed barcodes, and ranking the designed barcodes by their average Hamming distances). Alternatively, the barcoding module 1612 may compute isolation scores for the barcodes to rank the barcodes as described above. The barcoding module 1612 may also rank the gene transcripts of the sample according to expression levels of the corresponding genes. Then, the barcoding module 1612 may assign each gene transcript to one of the designed barcodes according to the same ranks, and direct the encoding of at least one of the gene transcripts (or a probe designed to target the gene transcript) with its assigned barcode. One example of this process is illustrated in Algorithm 3 above.

Alternatively or additionally, the barcoding module 1612 may generate tuples of the barcodes. Each tuple of barcodes may include, for example, a pairwise Hamming distance or a computed isolation score for the two barcodes used to form the tuple. The barcoding module 1612 may also generate tuples of genes or analytes to be encoded with the barcodes. Each tuple of genes may include, for example, a mean expression level of the genes in the tuple. The barcoding module 1612 may identify a first tuple of genes having a largest mean expression level of the genes used to form the tuple, and assign the identified first tuple of genes (or corresponding gene transcripts in the case that mRNA molecules are the target analytes) to a first tuple of designed barcodes based on the Hamming distance or isolation score of the first barcode tuple. From there, the barcoding module 1612 may direct encoding of at least one of the genes (or corresponding gene transcripts) of the first tuple of genes with its assigned barcode. Generally, a first barcode of a barcode tuple has a larger average Hamming distance or larger isolation score to remaining barcodes than a second barcode of the barcode tuple, and a first gene of a gene tuple has a larger expression level than a second gene of the gene tuple. In this regard, a first gene of a first gene tuple may be assigned to a first barcode of the first barcode tuple, and the second gene of the first gene tuple may be assigned to the second barcode of the first barcode tuple.

In identifying the first gene tuple and assigning the identified first gene tuple, the barcoding module 1612 may determine that the first designed barcode tuple has no barcodes assigned to any of the tuples of genes. Alternatively or additionally, the barcoding module 1612 may select the first tuple of designed barcodes from the tuples of barcodes according to a reverse rank order of pairwise Hamming distances or isolation scores for the barcodes in each tuple of barcodes when identifying the first tuple of genes and assigning barcodes to the identified first tuple of genes. Alternatively or additionally, the barcoding module 1612 may determine that one of the designed barcodes of the first tuple of barcodes is assigned to one of the plurality of genes or gene transcripts. In this regard, the barcoding module 1612 may identify another tuple of genes having the one gene and the largest mean expression level of the genes used to form the tuple, and assign the other gene of the other tuple of genes to the other of the barcodes of the first tuple of designed barcodes when identifying the first tuple of genes and assigning the identified first tuple of genes. One example of this process is illustrated in Algorithm 4 above.

Processes for Barcode Design and Decoding

Figure 19:
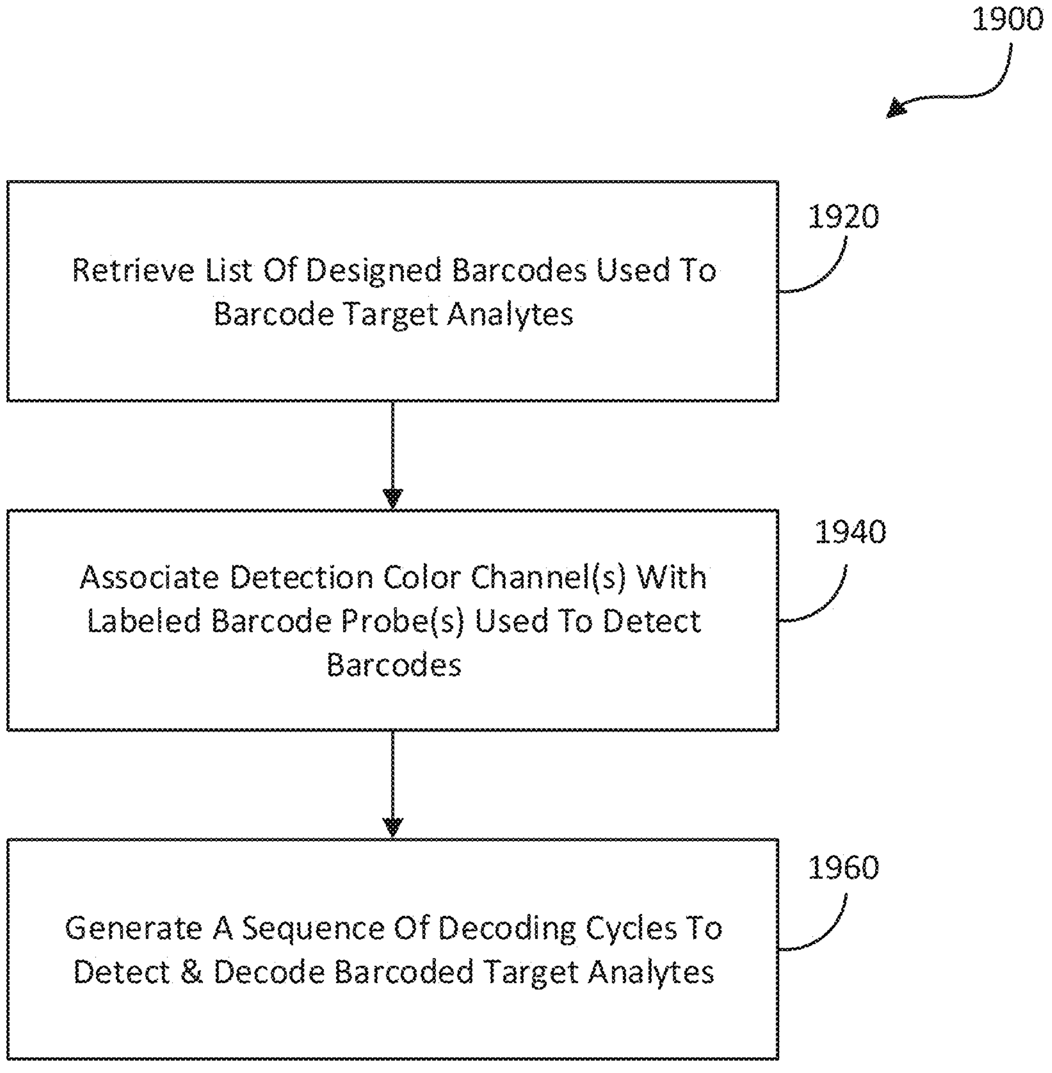
FIG. 19 provides a flowchart of an exemplary process for generating a decoding scheme that is tailored for a set of designed nucleic acid barcodes.

FIG. 19 is a flowchart of an exemplary process 1900 that may be performed by the system of FIG. 16. In some instances, a processor (either configured within the decoding module 1618 or configured with a separate processing system) is operable to retrieve a list of designed barcodes used to barcode, e.g., a plurality of nucleic acids 1616, in process step 1920. The decoding module 1618 may associate color channels with the labeled barcode probes used to detect a sequence of nucleotides (or barcode segment) of the barcoded nucleic acids (e.g., based on the chemistry of the barcode probes used to identify the barcode segment sequences) in process step 1940. Then, the decoding module 1618 may generate a sequence of decoding cycles to detect the designed barcode sequences, in process step 1960. Generally, each decoding cycle comprises detection of a plurality of states operable to identify at least one nucleotide (or a barcode segment comprising a plurality of nucleotides) associated with the designed barcodes.

Figure 20:
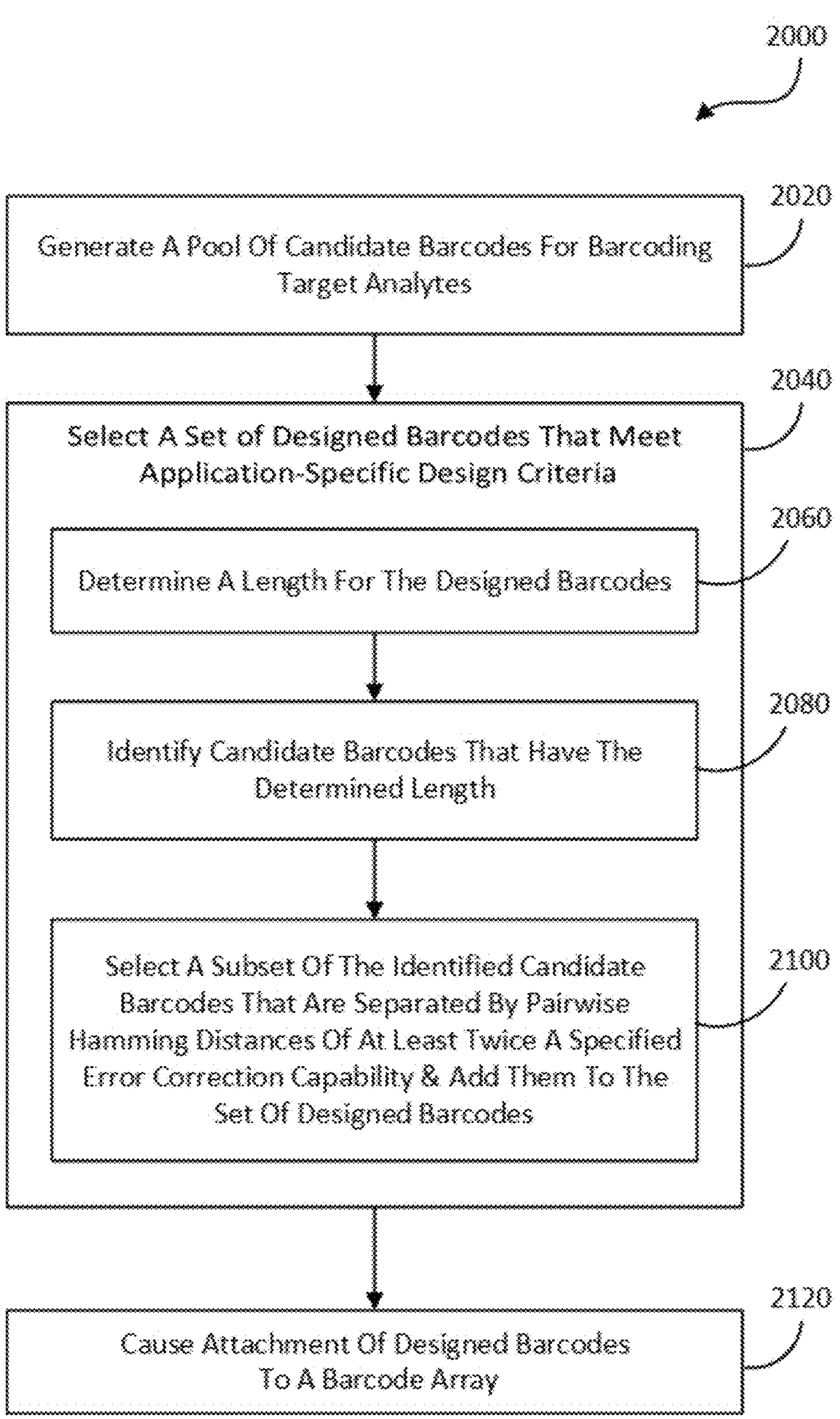
FIG. 20 provides a flowchart of an exemplary process for generating a set of designed nucleic acid barcodes that meet a specified set of design criteria to enable efficient error correction of barcode sequences.

FIG. 20 is a flowchart of an exemplary process 2000 that may be performed by the system of FIG. 16. In some instances, in process step 2020 barcoding module 1612 (or a processor therein) is operable to generate a pool of candidate barcodes (or segments thereof) to be associated with a plurality of target analytes, e.g., nucleic acid molecules 1616, that are to be detected. Then, in process step 2040, the processor may select a set of designed barcodes from the candidate barcode pool that satisfy a specified set of design criteria. For example, in selecting the designed barcodes, the processor may first determine a required length for the designed barcode sequences (e.g., to ensure that the set of designed barcodes has a specified diversity, or specified total number of unique barcode sequences) in the process step 2060. The processor may then select designed barcode sequences from the candidate barcode pool that have the determined length in process step 2080. The processor may then further select designed barcodes that have, e.g., a pairwise Hamming distances of more than two times an error correction capability (as described above, and illustrated in FIG. 1), in process step 2100. In some instances, barcoding module 1612 (or the processor within) is further operable to cause or control the attachment of the designed barcodes to, e.g., a spatial barcode array, in process step 2120. The barcoding module 1612 (or the processor within) may also direct the decoding module 1618 to generate a number of decoding cycles 1 . . . L that equals the length of the designed barcodes. In some instances, the decoding module 1618 may include an “OFF” letter or element in one or more of the decoding cycles as part of the decoding process design, as shown and described elsewhere herein, thereby effectively extending a length of the designed barcodes to enhance error correction capabilities.

Figure 21:
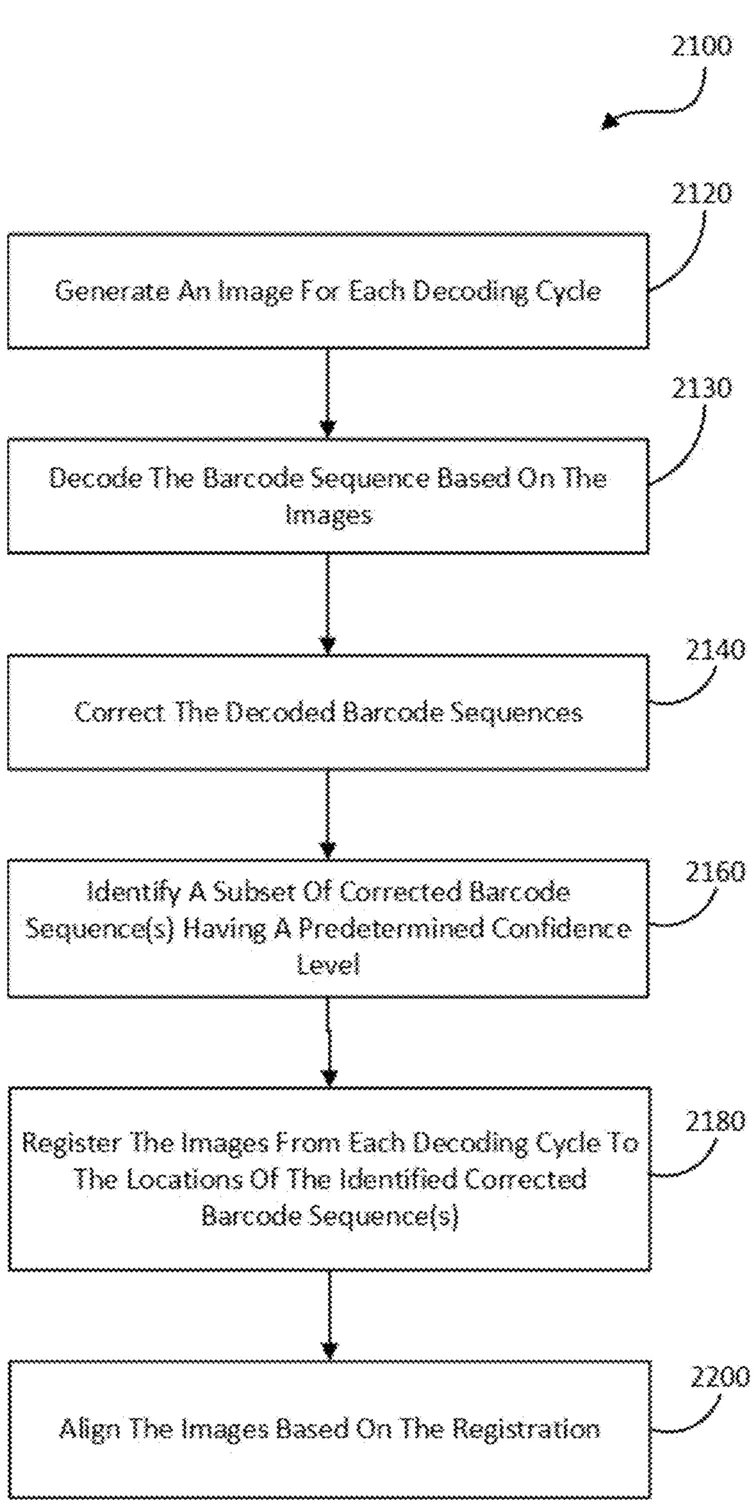
FIG. 21 provides a flowchart of an exemplary process for registering a plurality of images using the locations of detected barcode sequences in the images.

FIG. 21 is a flowchart of an exemplary process 2100 that may be performed by the system 1600 of FIG. 16. In some instances, the decoding module 1618 detects and decodes barcode sequences over a plurality of decoding cycles in step 2130, based on images generated by imaging module 1630 for each decoding cycle in process step 2120. The error correction module 1620 may then corrects the detected and decoded barcode sequences, in process step 2140, and identifies one (or more) of the detected barcode sequences having a predetermined minimum quality score or degree of confidence in process step 2160. For example, the corrected barcode sequence selected for image registration may have a confidence level of at least 80%, 90%, 95%, 98%, or 99% as calculated, e.g., from the probability of a corrected barcode sequence arising from one of the known designed barcode sequences. Imaging module 1630 may then register the series of images (e.g., images 132-1, 132-2, . . . 132-L as illustrated in FIG. 17) to the locations of the identified/detected barcode sequence in the images in process step 2180. The imaging module 1630 then aligns the images 132-1, 132-2, . . . 132-L based on the registration, in process step 2200 to produce a registered image (e.g., registered image 132 as shown in FIG. 17).

Figure 22:
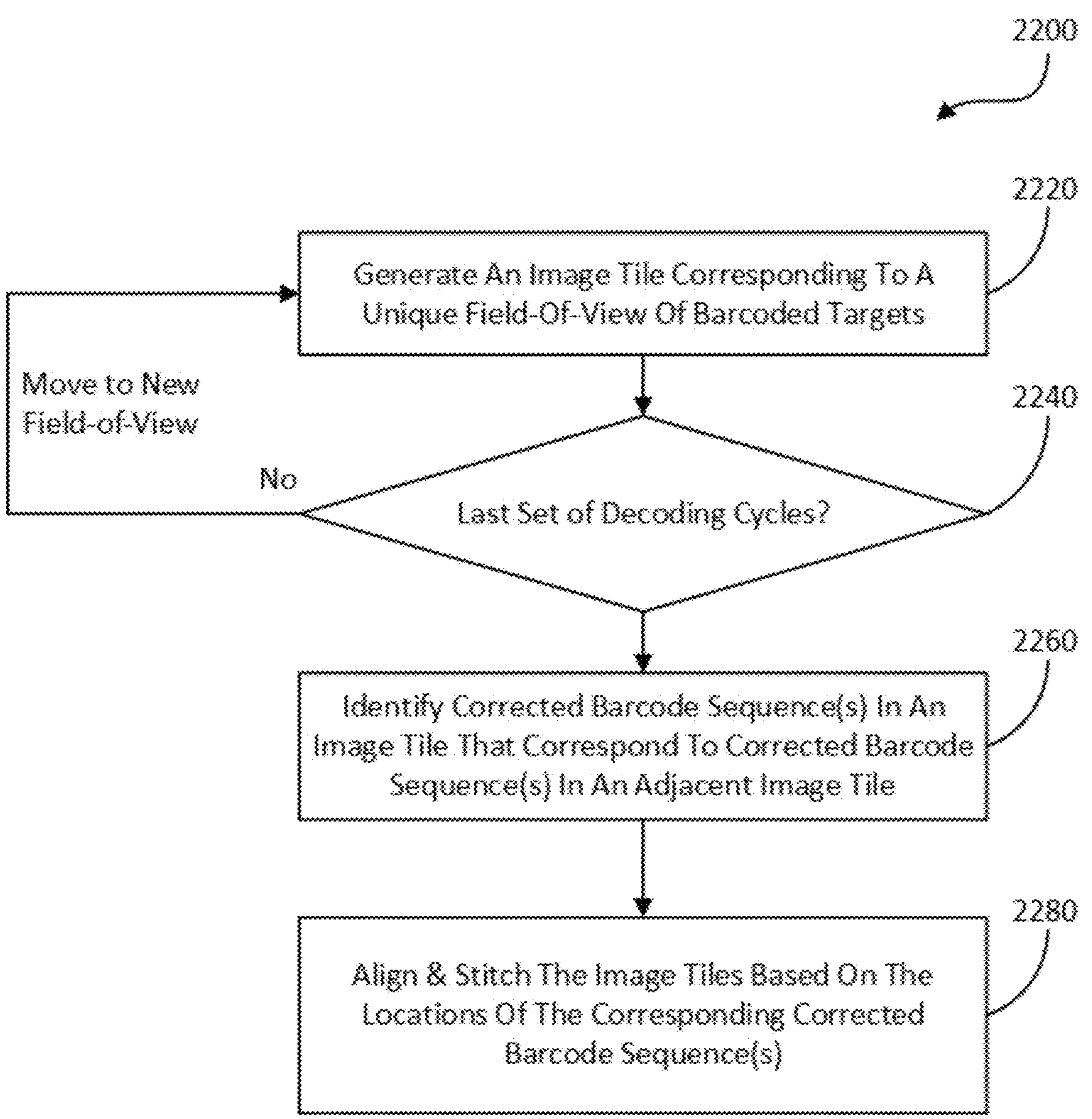
FIG. 22 provides a flowchart of an exemplary process for aligning and stitching adjacent image tiles based on the locations of detected barcode sequences in the images.

FIG. 22 is a flowchart of an exemplary process 2200 that may be performed by the system 1600 of FIG. 16. In some instances, the decoding module 1618 detects barcode sequences over a plurality of decoding cycles based on images for each of a plurality of locations (or fields-of-view) generated by imaging module 1630, which may then be used to generate an image tile for each set of decoding cycles (i.e., for each location or field-of-view), in process step 2220. Generally, each set of decoding cycle images corresponds to a unique location of, e.g., barcoded nucleic acids attached to a substrate surface. Once the last image tile of each set of decoding cycle images has been generated (e.g., determined at process step 2240), the imaging module 1630 may identify a portion of the detected barcode sequences in one image tile that correspond to a same portion of the detected barcode sequences in another image tile, in process step 2260. The imaging module 1630 may then align and stitch the adjacent image tiles together based on the identified portions of the detected barcoded sequences, in process step 2280.

Figure 23:
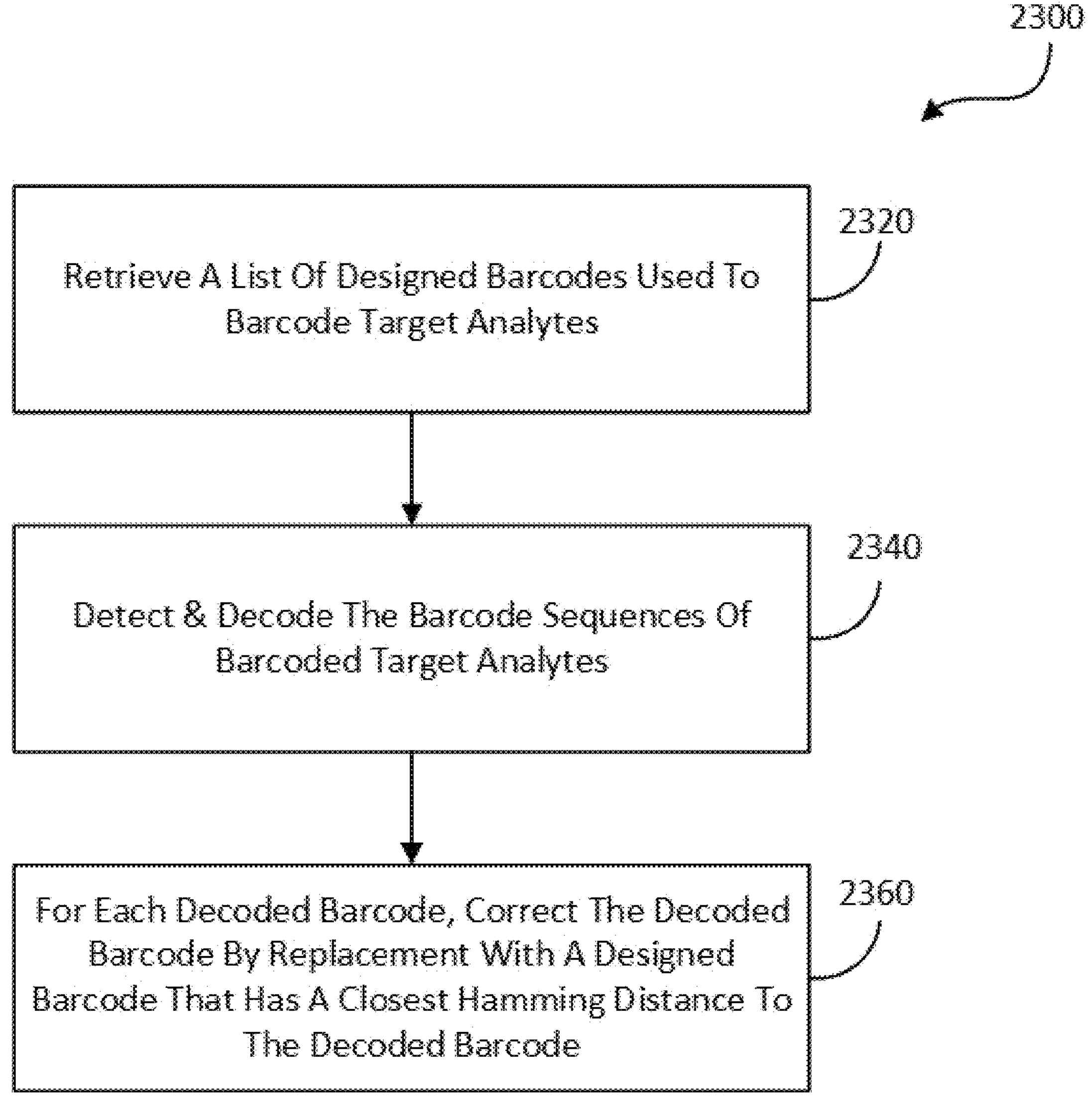
FIG. 23 provides a flowchart of an exemplary process for correcting decoded nucleic acid barcode sequences that comprise errors that is based on edit distance criteria (e.g., Hamming distance criteria).

FIG. 23 is a flowchart of an exemplary error correction process 2300 that may be performed by the system 1600 of FIG. 16. In some instances, the error correction module 1620 retrieves a list designed barcodes used to barcode, e.g., the nucleic acids 1616, in process step 2320. Thus, when the decoding module 1618 detects the barcode sequences of barcoded nucleic acids 16166, in process step 2340, the error correction module 1620 may detect errors and correct each detected and decoded barcode sequence comprising an error by replacement with one of the designed barcodes in the list that has a closest edit distances (e.g., a Hamming distance) to the detected and decode barcode sequence, in process step 2360.

Figure 24:
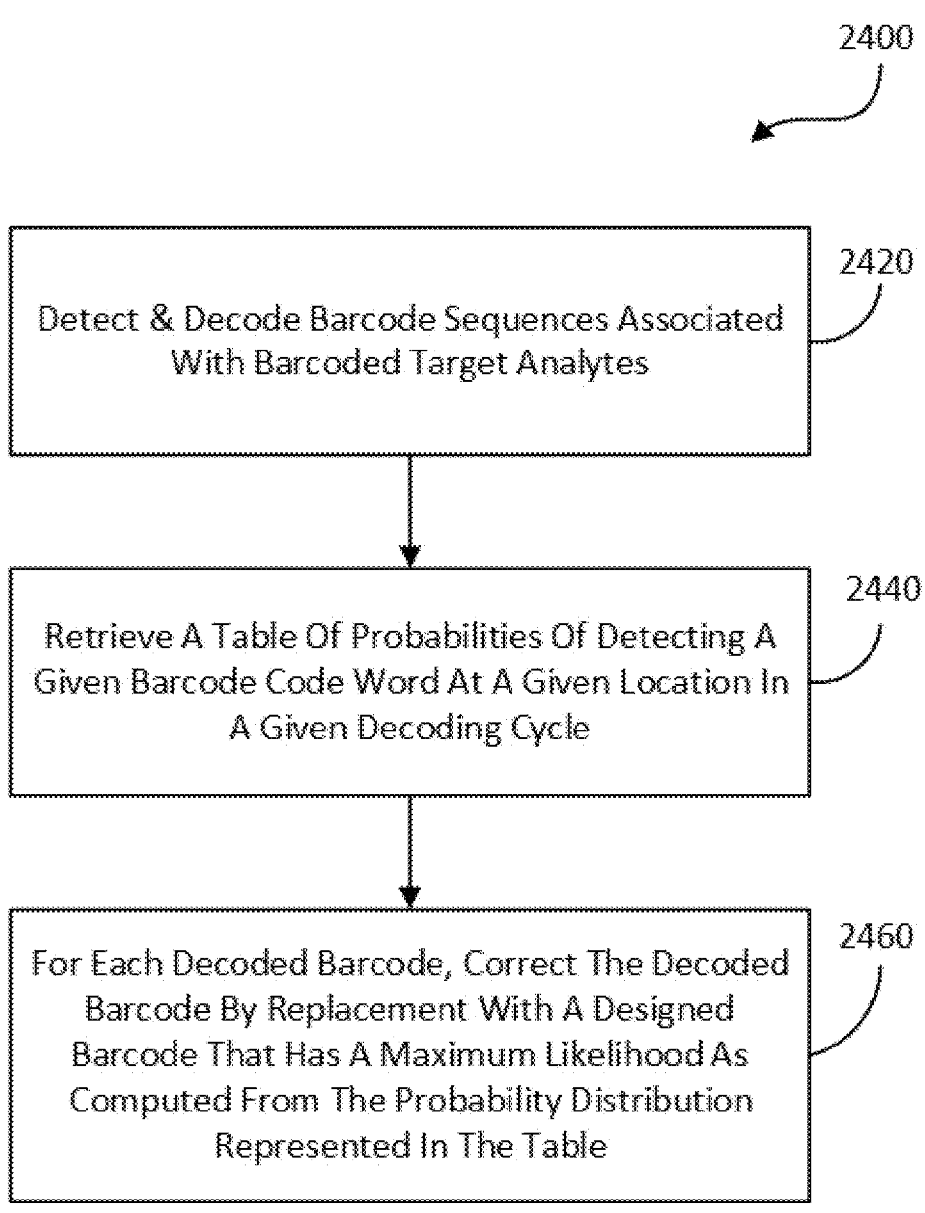
FIG. 24 provides a flowchart of an exemplary process for correcting decoded nucleic acid barcode sequences that comprise errors that is based on the use of a probabilistic model.

FIG. 24 is a flowchart of another exemplary error correction process 2400 that may be performed by the system 1600 of FIG. 16. In some instances, the decoding module 1618 detects and decodes the barcode sequences of, e.g., barcoded nucleic acids 1616, in process step 2420. The error correction module 1620 may then retrieve, e.g., a table of probabilities that a given barcode segment (code word) be detected at a given location in a given decoding cycle, in process step 2240. For each detected and decoded barcode sequence, the error correction module 1620 may then correct the detected barcode sequences comprising an error by replacement with one of the barcodes in a list of designed barcodes that has a maximum likelihood as computed from the probability distribution represented by the table of probabilities (e.g., by maximizing the log likelihood or minimizing the negative log likelihood of the probability distribution), in process step 2460.

Figure 25:
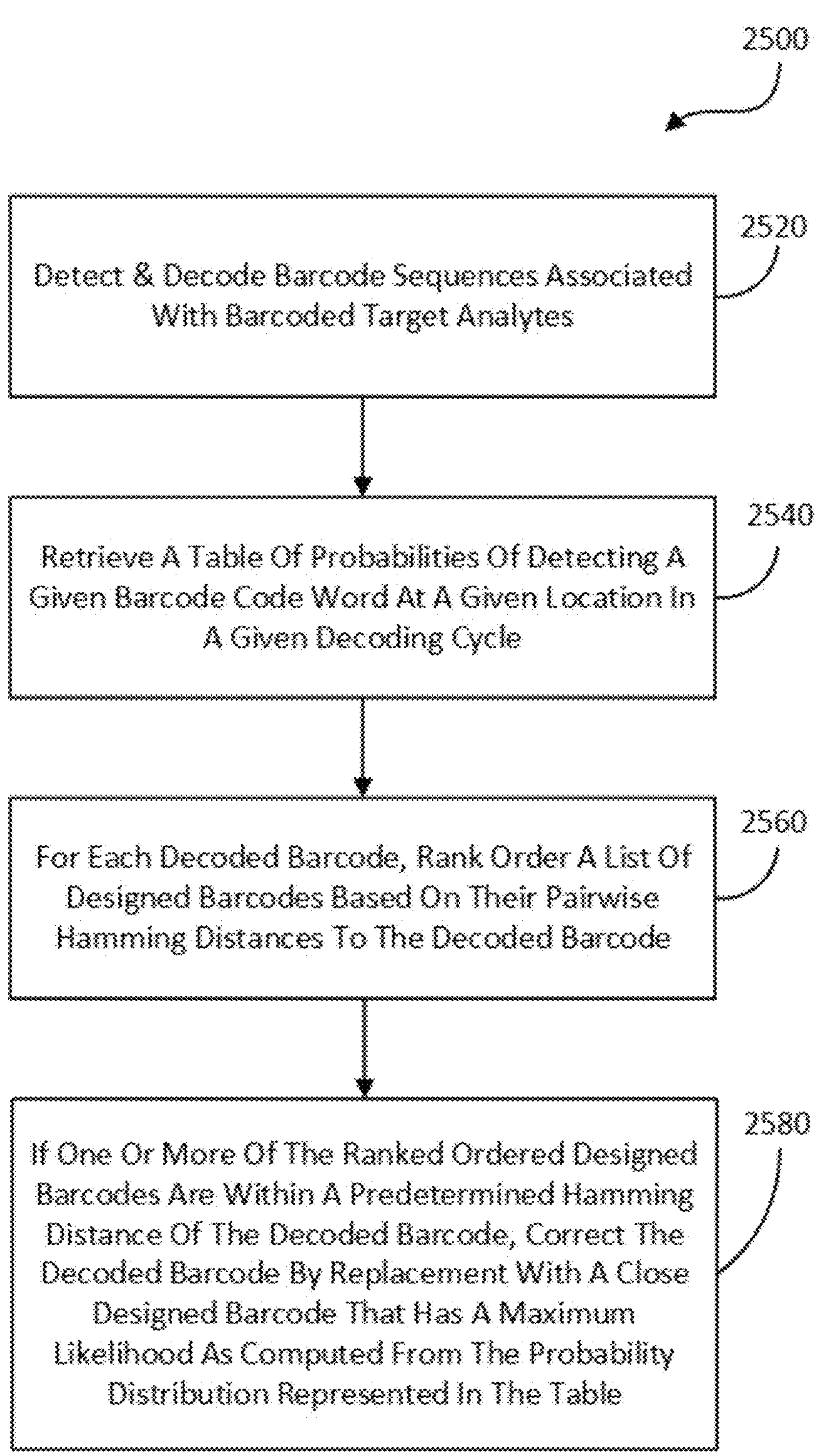
FIG. 25 provides a flowchart of an exemplary process for correcting decoded barcode sequences that comprise errors that is based on the use of a combination of edit distance criteria and a probabilistic model.

FIG. 25 is a flowchart of another exemplary error correction process 2500 that may be performed by the system 1600 of FIG. 16. In some instances, the decoding module 1618 detects and decodes barcode sequences of, e.g., a set of barcoded nucleic acids 1616, in process step 2520. The error correction module 1620 may then retrieve, e.g., a table of probabilities that a given barcode segment (code word) be detected at a given location in a given decoding cycle, in process step 2540. For each detected and decoded barcode sequence, the error correction module 1620 may then rank a list of known designed barcodes based on, e.g., their pairwise Hamming distances to the detected barcode sequence, in process step 2560. If one or more of the ranked list of designed barcodes are within a predetermined Hamming distance of the detected barcode sequence (e.g., within a Hamming distance of 3, 4, 5, or more than 5), the error correction module 1620 may correct the detected barcode sequence with one of the designed barcodes from the ranked list that is within the predetermined Hamming distance and that has a maximum likelihood as computed from the probability distribution represented by the table of probabilities (e.g., by maximizing the log likelihood or minimizing the negative log likelihood of the probability distribution), in process step 2580.

Figure 26:
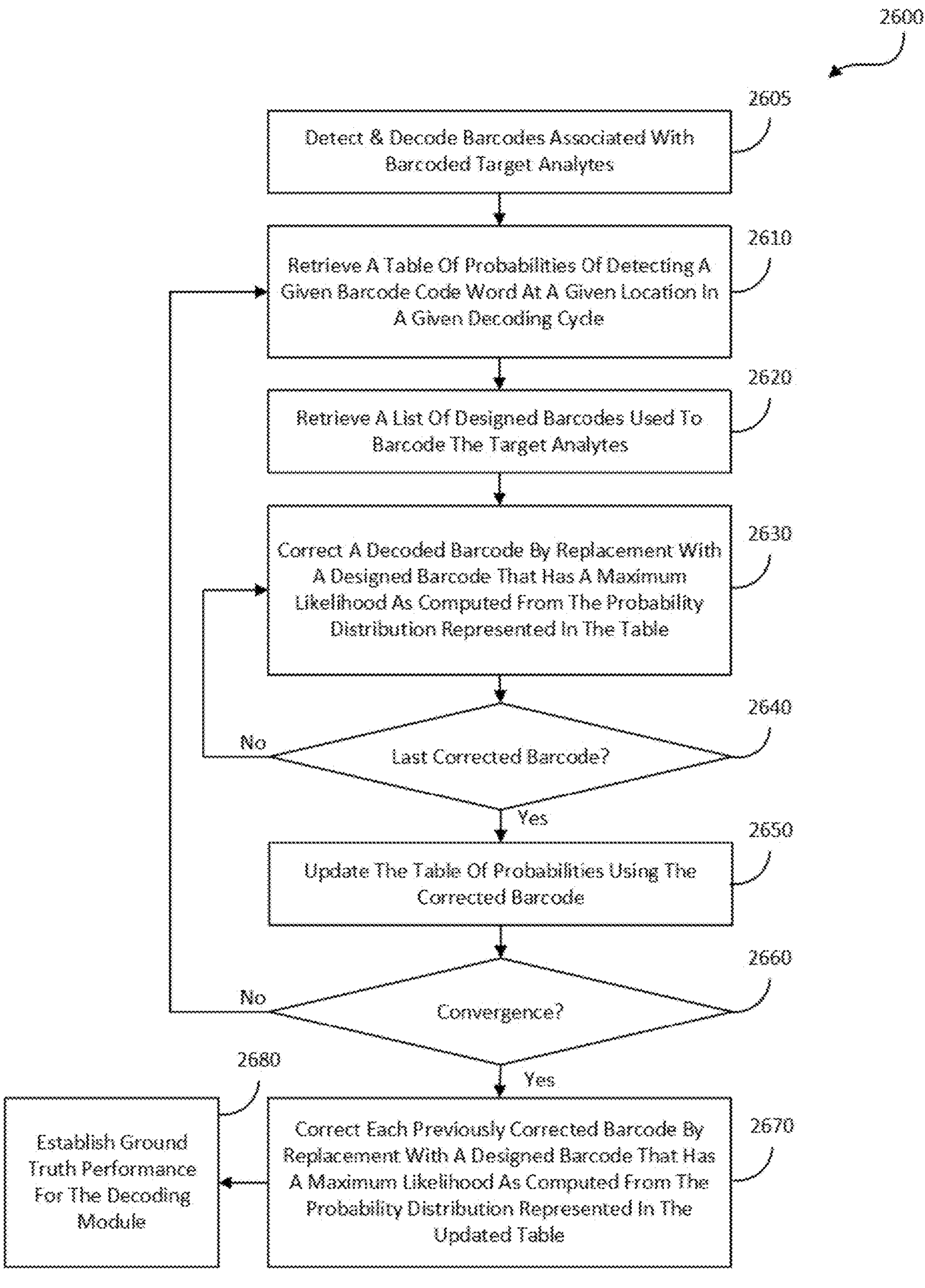
FIG. 26 provides a flowchart of an exemplary iterative process for correcting decoded barcode sequences that comprise errors that is based on the use of a probabilistic model.

FIG. 26 is a flowchart of an exemplary error correction process 2600 (e.g., corresponding to the soft iterative log likelihood correction of Algorithm 8 above) that may be performed by the system 1600 of FIG. 16. In some instances, the decoding module 1618 may detect and decode barcode sequences for a plurality of barcoded target analyte molecules, e.g., nucleic acid molecules 1616, in process step 2605. The error correction module 1620 may then retrieve, e.g., a table of probabilities that a given barcode segment (code word) will be detected at a given location in a given decoding cycle, in process step 2610. The error correction module 1620 may also retrieve, from the storage module 1614, a list of designed barcodes used to barcode the nucleic acid molecules 1616, in process step 2620.

For each of the detected and decoded barcode sequences, the error correction module 120 may iteratively correct the detected barcode sequence by replacement with one of the designed barcodes that has a maximum likelihood computed from the probability distribution represented by, e.g., a table of probabilities, as described above, in process step 2630. The error correction module 1620 may then determine if all decoded barcodes have been corrected in step 2640, and if so, update the table of probabilities using the corrected barcode sequences, in process step 2650.

Once each of the detected and decoded barcode sequences has been corrected (as determined in process step 2640) and the table of probabilities has been updated in process step 2650, the error correction module 1620 may determine whether the iterative error correction process 2600 has converged on a fully corrected set of barcodes, in process step 2660. As described above, determining whether or not convergence has been reached may include reaching a predetermined number of repetitions, determining whether the table of probabilities remains substantially unchanged from one iteration to the next, determining whether a substantial number of repeatedly corrected barcode sequences remains unchanged from a previous correction, or the like. If the process 2600 has not converged, then the error correction module 1620 may loop to process step 2610 to continue correcting the detected and decoded barcode sequences. If the process 1600 has converged, each previously corrected barcode sequence may optionally be corrected a final time by replacement with one of the designed barcodes from the retrieved list that has a maximum likelihood computed from the probability distribution represented by the updated table of probabilities (e.g., by maximizing the log likelihood or minimizing the negative log likelihood of the probability distribution), in process step 2670, and used to establish a ground truth determination of the performance of the decoding module 1618, in process step 2680, e.g., by comparing the final corrected barcode sequence calls computed using the updated probabilities to the corrected barcode sequences generated at convergence.

Figure 27:
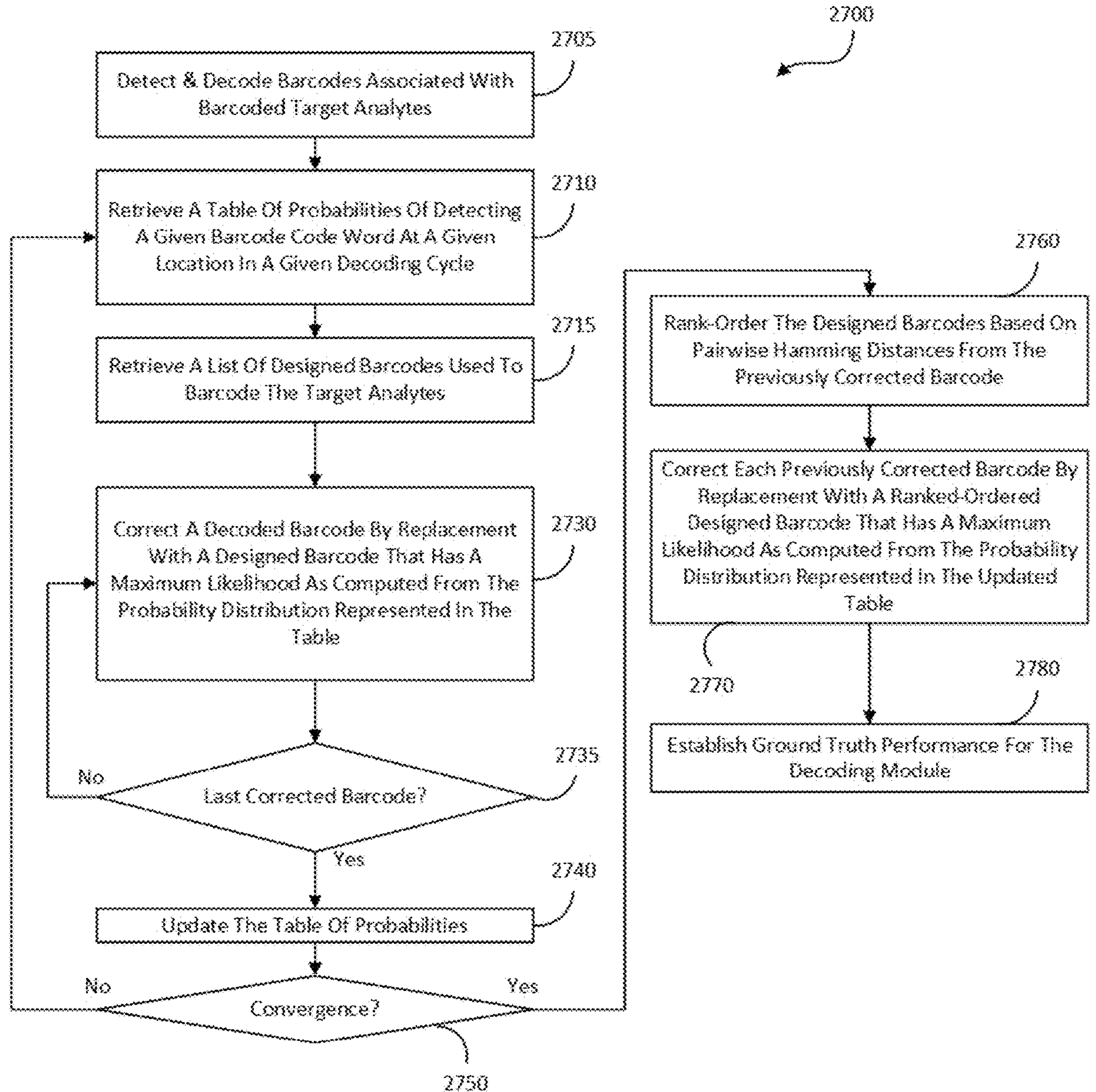
FIG. 27 provides a flowchart of an exemplary iterative process for correcting decoded barcode sequences that comprise errors that is based on the use of a combination of edit distance criteria and a probabilistic model.

FIG. 27 is a flowchart of another exemplary error correction process 2700 (e.g., corresponding to the hard iterative log likelihood correction of Algorithm 9 above) that may be performed by the system 1600 of FIG. 16. In some instances, the decoding module 1618 again detects and decodes barcode sequences in process step 2705. The error correction module 1620 may again retrieve a table of probabilities, in process step 2710, and a list of the known designed barcodes, in process step 2715.

The error correction module 1620 may then iteratively correct each of the detected and decoded barcode sequences by replacement with one of the designed barcodes that has a maximum likelihood as computed from the probability distribution represented by the table probabilities (e.g., by maximizing the log likelihood or minimizing the negative log likelihood of the probability distribution), in process step 2730. The error correction module 1620 then determines if all decoded barcodes have been corrected in process step 2735, and if so, updates the table of probabilities, in process step 2740. The error correction process is repeated until convergence is reached in process step 2750. Again, a determination of convergence may include reaching a predetermined number of repetitions, determining whether the table of probabilities remains substantially unchanged from one iteration to the next, determining whether a substantial number of repeatedly corrected barcode sequences remains unchanged from a previous correction, or the like.

Once the process 2700 converges on a fully corrected barcode set, the error correction module 1620 may, for each detected sequence, perform a final ranking of the designed barcodes based on their pairwise Hamming distances to a previously corrected barcode sequence, in process step 2760. As a final correction step, the error correction module 1620 may correct each previously corrected barcode sequence by replacement with a designed barcode from the ranked list that has a maximum likelihood as computed from the probability distribution represented by the table of probabilities (e.g., by maximizing the log likelihood or minimizing the negative log likelihood of the probability distribution), in process step 2720, and use the corrected barcodes to establish a ground truth determination of the performance of the decoding module 1618, in process step 2780.

Figure 28:
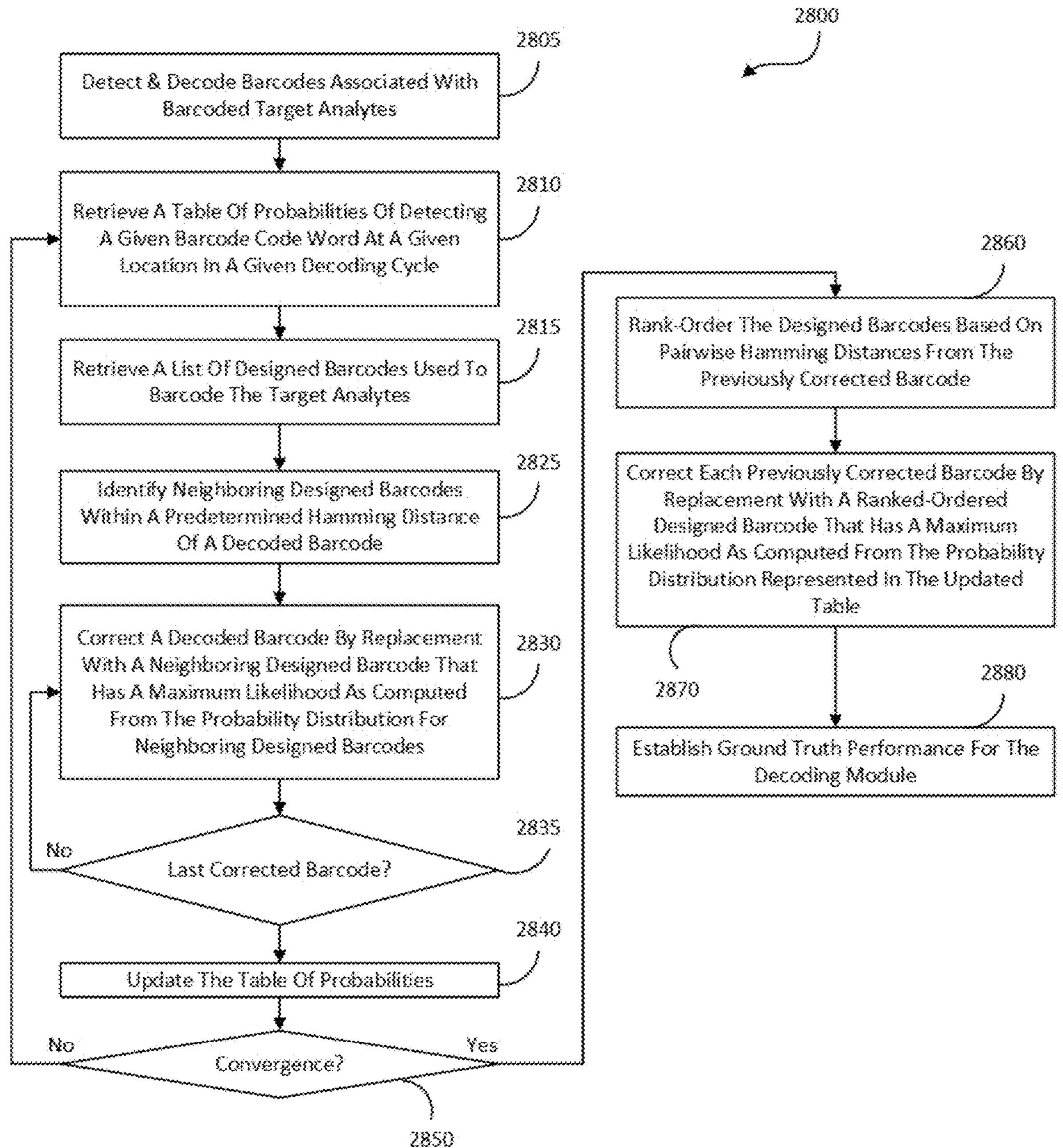
FIG. 28 provides a flowchart of an exemplary iterative process for correcting decoded barcode sequences that comprise errors that is based on the use of a combination of edit distance criteria to identify a set of nearest neighbor designed barcodes and a probabilistic model.

FIG. 28 is a flowchart of another exemplary error correction process 2800 (e.g., corresponding to the truncated iterative log likelihood correction of Algorithm 10 above) that may be performed by the system 1600 of FIG. 16. In some instances, the decoding module 1618 again detects and decodes barcode sequences in process step 2805. The error correction module 1620 may again retrieve a table of probabilities, in process step 2810, and retrieve a list of the known designed barcodes, in process step 2815.

The error correction module 1620 may then, and for each detected and decoded barcode sequence, identify neighboring designed barcodes that lie within a predetermined Hamming distance of the detected barcode sequence (e.g., within a Hamming distance of 3, 4, 5, or more than 5), in process step 2825, and correct the decoded barcode sequence by replacement with a designed barcode sequence that satisfies the specified Hamming distance criterion and that has a maximum likelihood as computed for the set of neighboring designed barcodes from the probability distribution represented by the table of probabilities (e.g., by maximizing the log likelihood or minimizing the negative log likelihood of the probability distribution), in process step 2830. The process 2800 may then comprise determining if all of the detected and decoded barcodes have been corrected in process step 2835, and if so, may then update the table of probabilities, in process step 2840. The error correction module 1620 may iteratively perform the process steps 2810-2850 until convergence is reached in process step 2850.

Once the error correction process has reached convergence, the error correction module 1620 may perform a final correction by, e.g., ranking the designed barcodes based on their pairwise Hamming distances to the previously corrected barcode sequence, in process step 2860, and then correct each previously corrected barcode sequence by replacement with a designed barcode from the ranked list of designed barcodes that has a maximum likelihood as computed from the probability distribution represented by the table probabilities, in process step 2870. The error correction module 1620 thus may also establish a ground truth determination of the performance for the decoding module 1618, in process step 2880, based on that final set of corrected barcodes.

In some instances, any of the decoding and error correction methods described herein may be applied to applications (e.g., in situ detection and/or in situ sequencing applications) in which target analyte sequences (e.g., target mRNA sequence) are directly detected rather than detecting barcodes associated with the target analytes. In these instances, the decoding process comprises the use of one or more target detection probes (each configured to bind or hybridize to one or more segments of the target analyte sequences), and yields a series of images that enable detection of one or more detection probes in each decoding cycle. The detection probes may thus be thought of as corresponding to or identifying code words, and the decoding process is used to determine the series of code words (decoded barcodes sequences) that function as proxies for the detected target analyte sequences. The disclosed decoding and error correction methods are operable to identify and correct errors in the "decoded barcode sequences" by replacing one or more of the decoded barcode sequences (i.e., proxies for the actual target analyte sequences) with a corresponding known proxy (series of code words) for a target analyte sequence that has, e.g., a closest edit distance (e.g., a closest Hamming distance) to the "decoded barcode sequence" and/or that has a maximum likelihood as calculated from a probability distribution that provides probabilities for detecting a given target detection probe (corresponding to a code word) at a given location in a given decoding cycle.

Figure 29:
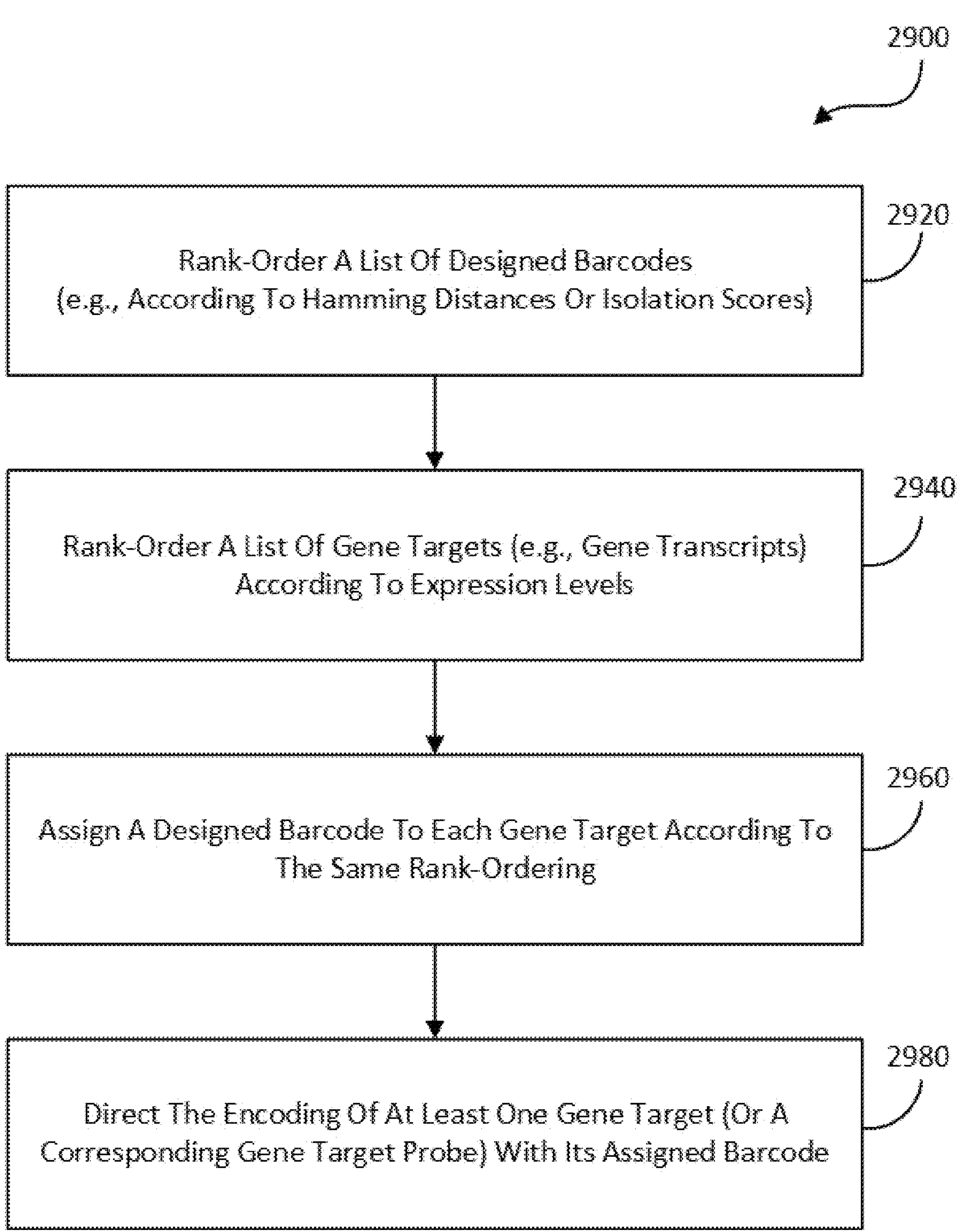
FIG. 29 provides a flowchart of an exemplary process for assigning designed barcodes to gene sequences or gene transcripts based on edit distance (e.g., Hamming distance) and gene expression level criteria.

FIG. 29 is a flowchart of an exemplary process 2900 (e.g., corresponding to Algorithm 3 described above) that may be performed by the system 1600 of FIG. 16. In some instances, the barcoding module 1612 may rank the designed barcodes, in process step 2920. For example, the barcoding module 1612 may rank each designed barcode by computing an average edit distance (e.g., an average Hamming distance) for each barcode relative to the other designed barcodes in the designed barcode pool. Alternatively, the barcoding module 1612 may compute an isolation score to rank the designed bar codes (e.g., based on a radius of error correction with respect to other designed barcodes, as illustrated in FIG. 1).

The barcoding module 1612 may also rank the genes of the sample according to the expression levels of the genes, in process step 2940. Then, the barcoding module 1612 may assign each target gene transcript corresponding to the ranked list of genes to one of the designed barcodes according to the same ranks, in process step 2960, and direct the encoding of at least one of the gene transcripts probes used for detection with its assigned barcode, in process step 2980.

Figure 30:
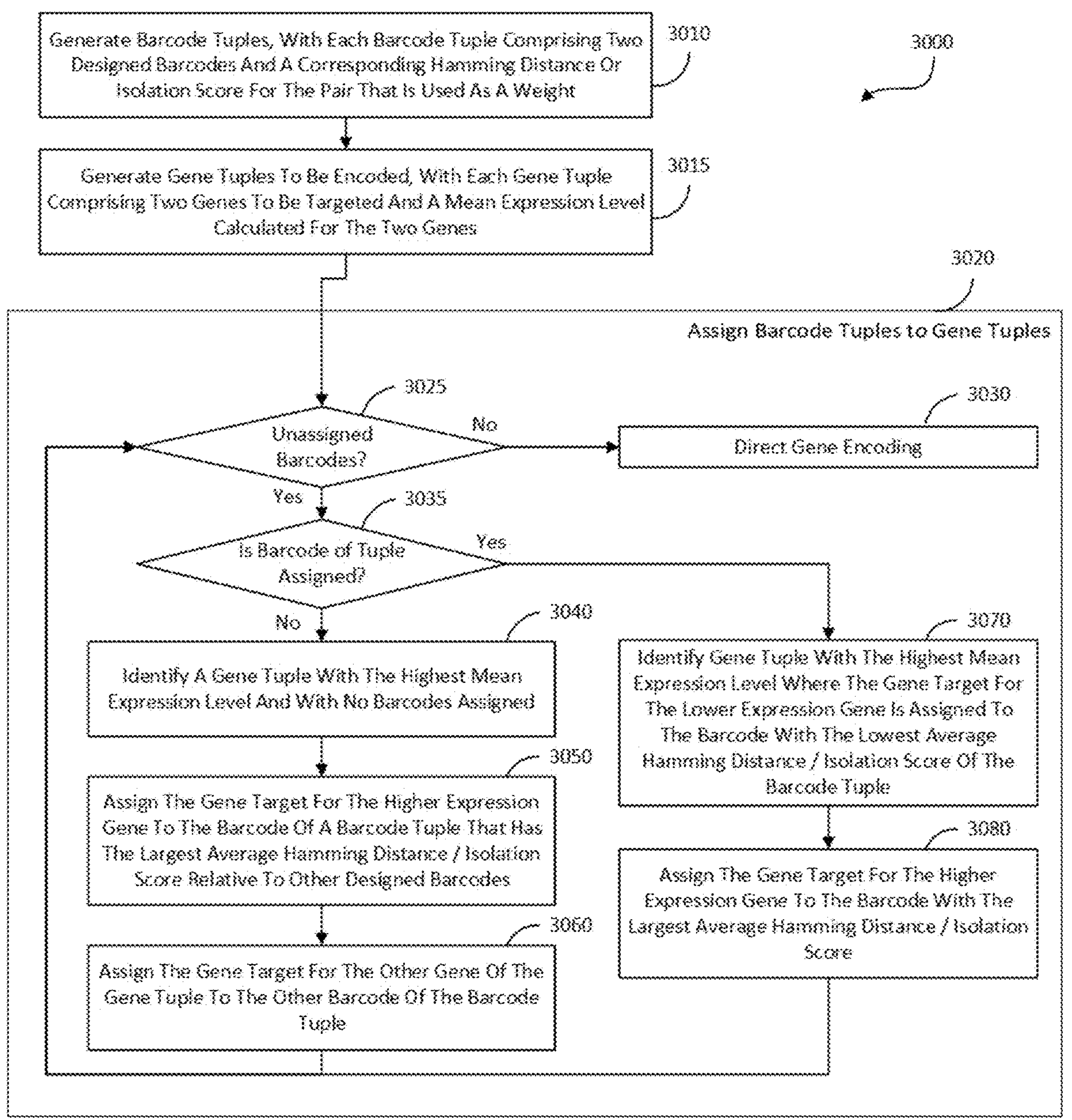
FIG. 30 provides a flowchart of an exemplary process for assigning designed barcodes to gene sequences or gene transcripts based on sets of barcode tuples and gene sequence (or gene transcript) tuples.

FIG. 30 is a flowchart of another exemplary process 3000 (e.g., corresponding to Algorithm 4 as described above) that may be performed by the system 160000 of FIG. 16. In some instances, the barcoding module 1612 generates designed barcode tuples for each of the designed barcodes, in process step 3010. Each designed barcode tuple comprises, e.g., a Hamming distance or a computed isolation score between the two designed barcodes used to form the tuple that is used as a weight for the designed barcode tuple. Each designed barcode may be used in multiple designed barcode tuples. The first designed barcode of each designed barcode tuple is generally configured to have the lower average Hamming distance or lower computed isolation score relative to the remaining designed barcodes in the barcode pool as compared to that for the second designed barcode of the designed barcode tuple.

The barcoding module 1612 may also generate gene tuples for each of the gene targets (e.g., gene sequences or gene transcripts) to be encoded, in process step 3015. Each gene tuple comprises a mean expression level used as a weight for the gene tuple. Similar to case for the designed barcodes, each gene target may be used in multiple gene tuples. The first gene of each gene tuple has the lower gene expression level of the two genes used to form the gene tuple.

The barcoding module 1612 then begins assigning designed barcode tuples to gene tuples, in process step 3020. In doing so, the barcoding module 1612 may reverse sort the list of designed barcode tuples according to their tuple weights and then determine whether any designed barcodes are unassigned, in process step 3025. If so, the barcoding module 1612 selects the next designed barcode tuple and determines whether any of the designed barcodes in the designed barcode tuple are assigned to a gene target, in process step 3035. If not, the barcoding module 1612 may identify a gene tuple with the highest mean expression level, in process step 3040. In this regard, barcoding module 1612 may assign the higher expression gene target of the gene tuple to the designed barcode with the largest average Hamming distance or largest computed isolation score in the designed barcode tuple, in process step 3050. The barcoding module 1612 may also assign the other gene of the gene tuple to the other designed barcode of the designed barcode tuple, in process step 3060. The barcoding module 1612 may then return to process step 3025 to determine whether there are any unassigned designed barcodes remaining.

Assuming that some designed barcodes remain unassigned, the barcoding module 1612 may select the next designed barcode tuple and again determine whether a designed barcode of the designed barcode tuple is assigned, in process step 3035. If so, the barcoding module 1612 may identify the gene tuples with the highest gene expression level where the lower expression gene of the gene tuple is assigned to the designed barcode with the lowest average Hamming distance or the lowest computed isolation score of the designed barcode tuple, in process step 3070. The barcoding module 161212 may then assign the higher expression gene of the gene tuple to the designed barcode with the largest average Hamming distance or the largest computed isolation score of the designed barcode tuple, in process step 3080. The barcoding module 1612 may then return to process step 3025 to determine whether there are any unassigned designed barcodes remaining. If not, the barcoding module 1612 may direct encoding of the gene targets, in process step 3030.

Computing Systems

Figure 31:
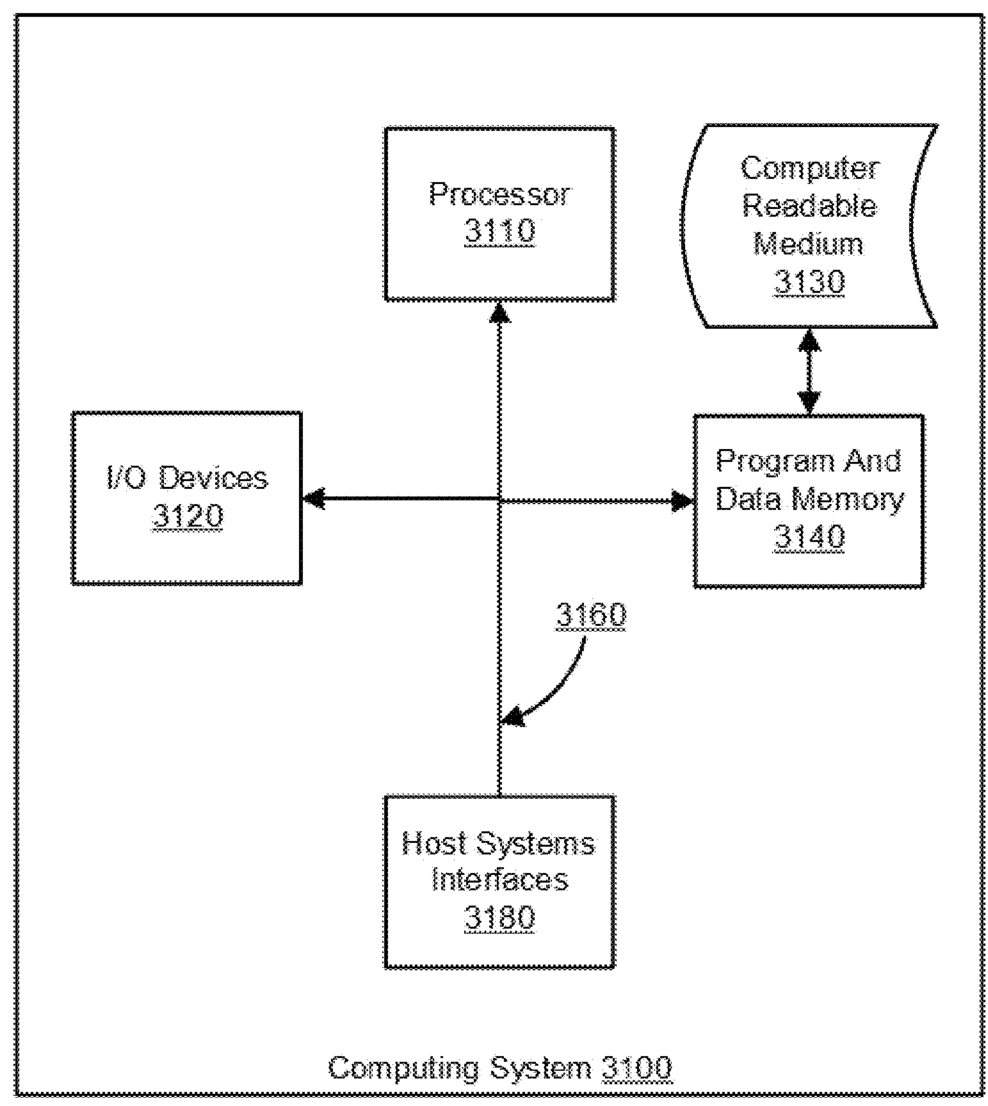
FIG. 31 illustrates a computing system in which a computer readable medium may provide instructions for performing methods disclosed herein.

FIG. 31 illustrates a computing system 3100 in which a computer readable medium 3130 may provide instructions for performing any of the methods and processes disclosed herein. Furthermore, some aspects of the embodiments herein can take the form of a computer program product accessible from the computer readable medium 3130 to provide program code for use by or in connection with a computer or any instruction execution system. For the purposes of this description, the computer readable medium 3130 can be any apparatus that can tangibly store the program code for use by or in connection with the instruction execution system, apparatus, or device, including the computing system 3100.

The computer readable medium 3130 can be any tangible electronic, magnetic, optical, electromagnetic, infrared, or semiconductor system (or apparatus or device). Some examples of a computer readable medium 306 include solid state memories, magnetic tapes, removable computer diskettes, random access memories (RAM), read-only memories (ROM), magnetic disks, and optical disks. Some examples of optical disks include read only compact disks (CD-ROM), read/write compact disks (CD-R/W), and digital versatile disks (DVD).

The computing system 3100 can include one or more processors 3110 coupled directly or indirectly to memory 3140 through a system bus 3160. The memory 3140 can include local memory employed during actual execution of the program code, bulk storage, and/or cache memories, which provide temporary storage of at least some of the program code in order to reduce the number of times the code is retrieved from bulk storage during execution.

Input/output (I/O) devices 3120 (including but not limited to keyboards, displays, pointing devices, I/O interfaces, etc.) can be coupled to the computing system 3100 either directly or through intervening I/O controllers. Network adapters may also be coupled to the computing system 3100 to enable the computing system 3100 to couple to other data processing systems, such as through host systems interfaces 3180, printers, and/or or storage devices through intervening private or public networks. Modems, cable modems, and Ethernet cards are just a few examples of network adapter types.

Example 1: In Situ Detection of Target Gene Transcripts

Target gene transcripts are assigned a codeword (e.g., a designed barcode described herein) in a sparse decoding process. In some instances, target gene transcripts are assigned a designed barcode based upon differential gene expression levels as described elsewhere herein. Probes (such as padlock probes) comprising a target binding region and a unique nucleic acid barcode sequence (chemical barcode) associated with a particular target are utilized to detect target gene transcripts. In some instances, chemical barcodes are a designed barcode sequence as described elsewhere herein. Probes are hybridized to a biological sample (e.g., a tissue section on a solid substrate) to allow probes to bind with the target gene transcripts. Any number of optional processing steps can be performed either pre- or post-probe hybridization (e.g., fixation, permeabilization, washes, hydrogel embedding, probe ligation, amplification, such as rolling circle amplification, etc.). Probes that bound to the target (or an amplified or processed product thereof) are then detected in a decoding process using, e.g., fluorescently labeled probes in a plurality of detection cycles (e.g., series of imaging cycles) to detect a plurality of features and generate a decoded barcode. In some instances, the adaptive error correction methodologies described herein are utilized to generate a corrected barcode. In some instances, the image registration and stitching methodologies described herein are utilized to adjust the registration of one or more images of the series of images and align the locations of the features to generate a decoded barcode. In some instances, the adaptive error correction and image registration and stitching methodologies described herein are utilized to adjust the registration of one or more images of the series of images and align the locations of the features to generate the corrected barcode. Decoded and/or corrected barcodes are then utilized to identify the target gene transcripts in the biological sample.

It should be understood from the foregoing that, while particular implementations of the disclosed methods, devices, and systems have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A computer-implemented method comprising:

obtaining an image for each decoding cycle of a plurality of decoding cycles to obtain a series of images;

registering the series of images;

detecting, in each image of the series of images, one or more locations of one or more respective barcode probe sequences of a plurality of barcode probes sequences, wherein the one or more respective barcode probe sequences are hybridized or bound to one or more target oligonucleotide sequences, or segments thereof;

decoding a plurality of target oligonucleotide sequences based on which decoding cycle and for which locations in one or more images of the series of images the one or more barcode probe sequences of the plurality are detected to obtain a plurality of decoded target oligonucleotide sequences;

identifying, based on the decoding of the plurality of target oligonucleotide sequences, a subset of the plurality of decoded target oligonucleotide sequences having (a) a decoding quality above a decoding quality threshold or (b) up to a predetermined degree of correction;

adjusting the registration of the series of images to improve alignments of the locations of the subset of the plurality of decoded target oligonucleotide sequences; and re-decoding the plurality of target oligonucleotide sequences based on the adjusted registration of the series of images.

2. The computer-implemented method of claim 1, wherein the target oligonucleotide sequences comprise target analyte sequences.

3. The computer-implemented method of claim 2, wherein the target analyte sequences comprise messenger ribonucleic acid (mRNA) sequences.

4. The computer-implemented method of claim 1, wherein the target oligonucleotide sequences comprise target barcode sequences associated with target analytes.

5. The computer-implemented method of claim 1, further comprising applying an error correction method to the plurality of decoded target oligonucleotide sequences prior to identifying the subset of the plurality of decoded target oligonucleotide sequences.

6. The computer-implemented method of claim 5, wherein the error correction method comprises replacement of one or more of the plurality of decoded target oligonucleotide sequences with a known target oligonucleotide sequence that is within a specified pairwise edit distance of the decoded target oligonucleotide sequence.

7. The computer-implemented method of claim 6, wherein the specified pairwise edit distance comprises a specified pairwise Hamming distance of less than two times a specified error correction capability.

8. The computer-implemented method of claim 5, wherein the error correction method comprises replacement of one or more of the plurality of decoded target oligonucleotide sequences with a known target oligonucleotide sequence that has a maximum likelihood as computed from a probability distribution that provides probabilities for detecting a given barcode probe sequence at a given location in a given decoding cycle.

9. The computer-implemented method of claim 5, wherein the error correction method comprises replacement of one or more of the plurality of decoded target oligonucleotide sequences with a known target oligonucleotide sequence that is within a specified pairwise edit distance of the decoded target oligonucleotide sequence, and that has a maximum likelihood as computed from a probability distribution that provides probabilities for detecting a given barcode probe sequence at a given location in a given decoding cycle.

10. The computer-implemented method of claim 9, wherein the specified pairwise edit distance comprises a specified pairwise Hamming distance of less than two times a specified error correction capability.

11. The computer-implemented method of claim 1, wherein the method comprises an iterative adjustment of the registration of the series of images to correct errors in the subset of the plurality of decoded target oligonucleotide sequences.

12. The computer-implemented method of claim 11, wherein the iterative adjustment is repeated until an improvement in a number of corrected target oligonucleotide sequences in the plurality of decoded target oligonucleotide sequences from one iteration to the next is less than a specified threshold.

13. The computer-implemented method of claim 1, wherein adjusting the registration of one or more images further comprises using detected locations for one or more fiducials in addition to the subset of decoded target oligonucleotide sequences.

14. The method of claim 1, wherein the degree of correction is a pairwise edit distance.

15. A system comprising:

one or more processors;

memory operably coupled to the one or more processors; and one or more programs stored in the memory that, when executed by the one or more processors, cause the system to execute a method comprising:

obtaining an image for each decoding cycle of a plurality of decoding cycles to obtain a series of images;

registering the series of images;

detecting, in each image of the series of images, one or more locations of one or more respective barcode probe sequences of a plurality of barcode probes sequences, wherein the one or more respective barcode probe sequences are hybridized or bound to one or more target oligonucleotide sequences or segments thereof;

decoding a plurality of target oligonucleotide sequences based on which decoding cycle and for which locations in one or more images of the series of images the one or more barcode probe sequences of the plurality are detected to obtain a plurality of decoded target oligonucleotide sequences;

identifying, based on the decoding of the plurality of target oligonucleotide sequences, a subset of the plurality of decoded target oligonucleotide sequences having (a) a decoding quality above a decoding quality threshold or (b) up to a predetermined degree of correction;

adjusting the registration of the series of images to improve alignments of the locations of the subset of the plurality of decoded target oligonucleotide sequences; and re-decoding the plurality of target oligonucleotide sequences based on the adjusted registration of the series of images.

16. The system of claim 15, wherein the degree of correction is a pairwise edit distance.

17. The system of claim 15, wherein the target oligonucleotide sequences comprise target analyte sequences.

18. The system of claim 17, wherein the target analyte sequences comprise messenger ribonucleic acid (mRNA) sequences.

19. The system of claim 15, wherein the target oligonucleotide sequences comprise target barcode sequences associated with target analytes.

20. The system of claim 15, wherein the method further comprises applying an error correction method to the plurality of decoded target oligonucleotide sequences prior to identifying the subset of the plurality of decoded target oligonucleotide sequence s.

21. The system of claim 15, wherein the method comprises an iterative adjustment of the registration of the series of images to correct errors in the subset of the plurality of decoded target oligonucleotide sequences.

22. The system of claim 21, wherein the iterative adjustment is repeated until an improvement in a number of corrected target oligonucleotide sequences in the plurality of decoded target oligonucleotide sequences from one iteration to the next is less than a specified threshold.

23. The system of claim 21, wherein the error correction method comprises replacement of one or more of the plurality of decoded target oligonucleotide sequences with a known target oligonucleotide sequence that is within a specified pairwise edit distance of the decoded target oligonucleotide sequence.

24. The system of claim 23, wherein the specified pairwise edit distance comprises a specified pairwise Hamming distance of less than two times a specified error correction capability.

25. The system of claim 21, wherein the error correction method comprises replacement of one or more of the plurality of decoded target oligonucleotide sequences with a known target oligonucleotide sequence that has a maximum likelihood as computed from a probability distribution that provides probabilities for detecting a given barcode probe sequence at a given location in a given decoding cycle.

26. The system of claim 21, wherein the error correction method comprises replacement of one or more of the plurality of decoded target oligonucleotide sequences with a known target oligonucleotide sequence that is within a specified pairwise edit distance of the decoded target oligonucleotide sequence, and that has a maximum likelihood as computed from a probability distribution that provides probabilities for detecting a given barcode probe sequence at a given location in a given decoding cycle.

27. The system of claim 26, wherein the specified pairwise edit distance comprises a specified pairwise Hamming distance of less than two times a specified error correction capability.

28. The system of claim 15, wherein adjusting the registration of one or more images further comprises using detected locations for one or more fiducials in addition to the subset of decoded target oligonucleotide sequences.

* * * * *